United States Patent
Griswold et al.

(10) Patent No.: US 10,358,636 B2
(45) Date of Patent: Jul. 23, 2019

(54) DEIMMUNIZED LYSOSTAPHIN AND METHODS OF USE

(71) Applicants: TRUSTEES OF DARTMOUTH COLLEGE, Hanover, NH (US); STEALTH BIOLOGICS, LLC, Lyme, NH (US)

(72) Inventors: Karl E. Griswold, Lyme, NH (US); Chris Bailey-Kellogg, Stratford, VT (US); Yoonjoo Choi, Gyeonggi-do (KR); Kristina Blazanovic, Crkvina (BA); Hongliang Zhao, Hanover, NH (US); Deeptak Verma, Wilder, VT (US)

(73) Assignees: STEALTH BIOLOGICS, LLC, Lyme, NH (US); TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/310,917

(22) PCT Filed: May 14, 2015

(86) PCT No.: PCT/US2015/030765
§ 371 (c)(1),
(2) Date: Nov. 14, 2016

(87) PCT Pub. No.: WO2015/175774
PCT Pub. Date: Nov. 19, 2015

(65) Prior Publication Data
US 2017/0145398 A1    May 25, 2017

Related U.S. Application Data

(60) Provisional application No. 61/993,056, filed on May 14, 2014, provisional application No. 62/003,256, filed on May 27, 2014, provisional application No. 62/115,326, filed on Feb. 12, 2015, provisional application No. 62/155,079, filed on Apr. 30, 2015.

(51) Int. Cl.
| | | |
|---|---|---|
| *C12N 9/52* | (2006.01) | |
| *A61K 31/18* | (2006.01) | |
| *A61K 31/47* | (2006.01) | |
| *A61K 38/00* | (2006.01) | |
| *A61K 38/48* | (2006.01) | |
| *A61K 45/06* | (2006.01) | |
| *A61K 31/397* | (2006.01) | |
| *A61K 31/519* | (2006.01) | |
| *A61K 31/545* | (2006.01) | |
| *A61K 31/7036* | (2006.01) | |
| *A61K 31/7048* | (2006.01) | |

(52) U.S. Cl.
CPC ............... *C12N 9/52* (2013.01); *A61K 31/18* (2013.01); *A61K 31/397* (2013.01); *A61K 31/47* (2013.01); *A61K 31/519* (2013.01); *A61K 31/545* (2013.01); *A61K 31/7036* (2013.01); *A61K 31/7048* (2013.01); *A61K 38/48* (2013.01); *A61K 38/4886* (2013.01); *A61K 45/06* (2013.01); *C12Y 304/24075* (2013.01); *A61K 38/00* (2013.01)

(58) Field of Classification Search
None
See application file for complete search history.

(56) References Cited

U.S. PATENT DOCUMENTS

| | | |
|---|---|---|
| 4,424,311 A | 1/1984 | Nagaoka et al. |
| 4,931,390 A | 6/1990 | Recsei |
| 5,446,090 A | 8/1995 | Harris |
| 5,672,662 A | 9/1997 | Harris et al. |
| 5,739,208 A | 4/1998 | Harris |
| 5,900,461 A | 5/1999 | Harris |
| 5,932,462 A | 8/1999 | Harris et al. |
| 5,990,237 A | 11/1999 | Bentley et al. |
| 6,028,051 A | 2/2000 | Climo et al. |
| 6,214,966 B1 | 4/2001 | Harris |
| 6,348,558 B1 | 2/2002 | Harris et al. |
| 6,362,254 B2 | 3/2002 | Harris et al. |
| 6,362,276 B1 | 3/2002 | Harris et al. |
| 6,432,397 B1 | 8/2002 | Harris |
| 6,437,025 B1 | 8/2002 | Harris et al. |
| 6,448,369 B1 | 9/2002 | Bentley et al. |
| 6,515,100 B2 | 2/2003 | Harris |
| 6,541,543 B2 | 4/2003 | Harris et al. |
| 6,569,830 B1 | 5/2003 | Climo et al. |
| 6,610,281 B2 | 8/2003 | Harris |

(Continued)

FOREIGN PATENT DOCUMENTS

| | | |
|---|---|---|
| WO | 1998/052976 A1 | 11/1998 |
| WO | 2000/034317 A2 | 6/2000 |

(Continued)

OTHER PUBLICATIONS

Design and analysis of immune-evading enzymes for ADEPT therapy Protein Engineering, Design & Selection vol. 25 No. 10 pp. 613-623, 2012, Published online Aug. 16, 2012.*

Hongliang Zhao, Gene and Protein Sequence Optimization for High-Level Production of Fully Active and Aglycosylated Lysostaphin in Pichia pastoris.*

Lu et al. (Feb. 4, 2013) "Hydrogen/Deuterium Exchange Mass Spectrometry and Site-Directed Disulfide Cross-Linking Suggest an Important Dynamic Interface between the Two Lysostaphin Domains," Antimicrob. Agents Chemother. 57:1872-1881.

McCaldon et al. (1988) "Oligopeptide biases in protein sequences and their use in predicting protein coding regions in nucleotide sequences," Proteins: Structure, Function and Bioinformatics. 4:99-122.

(Continued)

*Primary Examiner* — Kagnew H Gebreyesus
(74) *Attorney, Agent, or Firm* — Brian C. Trinque; Michael Spellberg; Lathrop Gage LLP

(57) ABSTRACT

Compositions comprising deimmunized lysostaphin and methods of using the same, e.g., to treat microbial infection in or on a subject, are provided.

34 Claims, 11 Drawing Sheets

Specification includes a Sequence Listing.

(56) References Cited

U.S. PATENT DOCUMENTS

| | | | |
|---|---|---|---|
| 6,664,331 | B2 | 12/2003 | Harris et al. |
| 6,737,505 | B2 | 5/2004 | Bentley et al. |
| 6,828,401 | B2 | 12/2004 | Nho et al. |
| 6,864,327 | B2 | 3/2005 | Bentley et al. |
| 6,864,350 | B2 | 3/2005 | Harris |
| 6,894,025 | B2 | 5/2005 | Harris |
| 7,078,377 | B1 | 7/2006 | Climo et al. |
| 7,091,332 | B1 | 8/2006 | Bramley et al. |
| 8,202,516 | B2 * | 6/2012 | Padmanabhan ...... C12N 9/2462 424/94.61 |
| 2003/0211995 | A1 | 11/2003 | Kokai-Kun et al. |
| 2003/0215433 | A1 | 11/2003 | Kokai-Kun et al. |
| 2004/0180386 | A1 | 9/2004 | Carr |
| 2004/0192581 | A1 | 9/2004 | Walsh et al. |
| 2005/0118159 | A1 | 6/2005 | Stinson et al. |
| 2008/0095756 | A1 | 4/2008 | Stinson et al. |
| 2017/0318817 | A1 * | 11/2017 | Padmanabhan ...... C12N 9/2462 |

FOREIGN PATENT DOCUMENTS

| | | | |
|---|---|---|---|
| WO | 2002/002630 | A2 | 1/2002 |
| WO | 2003/031581 | A2 | 4/2003 |
| WO | 2003/082148 | A1 | 10/2003 |
| WO | 2008/105826 | A2 | 9/2008 |

OTHER PUBLICATIONS

Meyer et al. (2008) "An emerging star for therapeutic and catalytic protein production," BioProc. Internat. 6:10-21.

Mierau et al. (2005) "Industrial-scale production and purification of a heterologous protein in Lactococcus lactis using the nisin-controlled gene expression system NICE: the case of lysostaphin," Microb. Cell Fact. 4:15. pp. 1-9.

Moise et al. (Sep. 17, 2013) "Immunization with cross-conserved H1N1 influenza CD4+ T-cell epitopes lowers viral burden in HLA DR3 transgenic mice," Humm. Vaccin. Immunother. 9:2060-2068.

Niesen et al. (2007) "The use of differential scanning fluorimetry to detect ligand interactions that promote protein stability," Nat. Protocols 2:2212-2221.

Odintsov et al. (2004) "Latent LytM at 1.3A resolution," J. Mol. Biol. 335:775-785.

Parker et al. (Feb. 2013) "Structure-guided deimmunization of therapeutic proteins," J. Computation. Biol. 20:152-165.

Patel et al. (2004) "Antistaphylococcal activity of WCK 771, a tricyclic fluoroquinolone, in animal infection models," Antimicrob. Agents Chemother. 48:4754-4761.

Pearlman et al. (1995) "AMBER, a package of computer programs for applying molecular mechanics, normal mode analysis, molecular dynamics and free energy calculations to simulate the structural and energetic properties of molecules," Comput. Phys. Commun. 91:1-41.

Placencia et al. (2009) "Treatment of Methicillin-Resistant *Staphylococcus aureus* in Neonatal Mice: Lysostaphin Versus Vancomycin" Ped. Res. 65:420-424.

Rohl et al. (2004) "Protein structure prediction using Rosetta," Methods Enzymol. 383:66-91.

Romano et al. (2006) "Outbreak of community-acquired methicillin-resistant *Staphylococcus aureus* skin infections among a collegiate football team," J. Athl. Train. 41:141-145.

Rost (1999) "Twilight zone of protein sequence alignments," Prot. Eng. Design Select. 12:85-94.

Salvat et al. (Mar. 25, 2014) "A high throughput MHC II binding assay for quantitative analysis of peptide epitopes," J. Vis. Exp. 85:e51308. pp. 1-11.

Schaffner et al. (1967) "Lysostaphin: an enzymatic approach to staphylococcal disease. II. In vivo studies," Yale J. Biol. Med. 39:230-244.

Schindler et al. (1964) "Lysostaphin: A New Bacteriolytic Agent for the Staphylococcus," Proc. Natl. Acad. Sci. USA 51:414-421.

Schuhardt et al. (1964) "Lysostaphin therapy in mice infected with *Staphylococcus aureus*," J. Bacteriol. 88:815-816.

Sharma et al. (2006) "Cytoplasmic expression of mature glycylglycine endopeptidase lysostaphin with an amino terminal hexa-histidine in a soluble and catalytically active form in *Escherichia coli*," Prot. Exp. Purif. 45:206-215.

Shekhar (2008) "Pichia power: India's biotech industry puts unconventional yeast to work," Chem. Biol. 15:201-202.

Shen et al. (2006) "Statistical potential for assessment and prediction of protein structures," Protein Sci. 15:2507-2524.

Singh et al. (2001) "ProPred: prediction of HLA-DR binding sites," Bioinformatics 17:1236-1237.

Southwood et al. (1998) "Several common HLA-DR types share largely overlapping peptide binding repertoires," J. Immunol. 160:3363-3373.

Still et al. (1990) "Semianalytical treatment of salvation for molecular mechanics and dynamics," J. Am. Chem. Soc. 112:6127-6129.

Szweda et al. (2005) "New effective sources of the Staphylococcus simulans lysostaphin," J. Biotechnol. 117:203-213.

Tangri et al. (2005) "Rationally Engineered Therapeutic Proteins with Reduced Immunogenicity," J. Immunol. 174:3187-3196.

Tonomura et al. (2008) "Antigen-specific human T-cell responses and T cell—dependent production of human antibodies in a humanized mouse model," Blood. 111:4293-4296.

Vogl et al. (Dec. 2013) "New opportunities by synthetic biology for biopharmaceutical production in Pichia pastoris," Curr. Opin. Biotechnol. 24:1094-1101.

Walsh (2010) "Biopharmaceutical benchmarks 2010," Nature Biotechnol. 28:917-924.

Walsh et al. (2003) "Improved pharmacokinetics and reduced antibody reactivity of lysostaphin conjugated to polyethylene glycol," Antimicrob. Agents Chemother. 47:554-558.

Watanabe et al. (2009) "The analysis of the functions of human B and T cells in humanized NOD/shi-scid/gammac (null) (NOG) mice (hu-HSC NOG mice)," Inter. Immunol. 21:843-858.

Weber et al. (2009) "T cell epitope: friend or foe? Immunogenicity of biologics in context," Adv. Drug Deliv. Rev. 61:965-976.

Wen et al. (2011) "Applications of differential scanning calorimetry for thermal stability analysis of proteins: Qualification of DSC," J. Pharm. Sci. 101:955-964.

Wu et al. (2004) "High efficiency transformation by electroporation of Pichia pastoris pretreated with lithium acetate and dithiothreitol," Biotechniques 36:152-154.

Zhao et al. (2000) "Synonymous codon usage in Pichia pastor's," Sheng Wu Gong Cheng Xue Bao. 16:308-311.—English Abstract and Figures.

Zhao et al. (Feb. 21, 2014) "Gene and protein sequence optimization for high-level production of fully active and aglycosylated lysostaphin in Pichia pastoris," Appl. Environ. Microbiol. 80:2746-2753.

Zinderman et al. (2004) "Community-acquired methicillin-resistant *Staphylococcus aureus* among military recruits," Emerg. Infect. Dis. 10:941-944.

International Search Report with Written Opinion corresponding International Patent Application No. PCT/US2015/030765, dated Aug. 27, 2015.

Adcock et al. (1998) "Methicillin-resistant *Staphylococcus aureus* in two child care centers," J. Infect. Dis. 178:577-580.

Altschul et al. (1997) "Gapped BLAST and PSI-BLAST: a new generation of protein database search programs," Nucleic Acids Res. 25:3389-3402.

Baba et al. (1996) "Target cell specificity of a bacteriocin molecule: a C-terminal signal directs lysostaphin to the cell wall of *Staphylococcus aureus*," EMBO J. 15:4789-4797.

Baker et al. (2001) "Protein structure prediction and structural genomics," Science. 294:93-96.

Bowie (1990) "Deciphering the message in protein sequences: tolerance to amino acid substitutions," Science. 247:1306-1310.

Brainard et al. (2009) "Induction of robust cellular and humoral virus-specific adaptive immune responses in human immunodeficiency virus-infected humanized BLT mice," J. Virol. 83:7305-21.

Brinks et al. (May 7, 2013) "Preclinical models used for immunogenicity prediction of therapeutic proteins," Pharma. Res. 30:1719-1728.

Chen et al. (2009) "Computational structure-based redesign of enzyme activity," Proc. Natl. Acad. Sci. USA. 106(10):3764-3769 and correction at 106(18):7678.

(56) References Cited

OTHER PUBLICATIONS

Choi et al. (2010) "FREAD revisited: Accurate loop structure prediction using a database search algorithm," Proteins. 78:1431-1440.
Chou et al. (1974) "Prediction of protein conformation," Biochem. 13:222-245.
Climo et al. (1998) "Lysostaphin treatment of experimental methicillin-resistant *Staphylococcus aureus* aortic valve endocarditis," Antimicrob. Agents Chemother. 42:1355-1360.
Cropp et al. (1964) "The In Vitro Effect of Lysostaphin on Clinical Isolates of *Staphylococcus aureus*," Can. J. Microbiol. 10:823-828.
De Groot et al. (2007) "Prediction of immunogenicity for therapeutic proteins: state of the art," Curr. Opin. Drug Discov. Devel. 10(3):332-340.
De Groot et al. (2011) "Immunogenic Consensus Sequence T Helper Epitopes for a Pan-Burkholderia Biodefense Vaccine," Immunome Res. 7:7. pp. 1-10.
De Groot et al. (Nov. 2013) "Beyond Humanization and De-Immunization: Tolerization as a Method for Reducing the Immunogenicity of Biologics," Exp. Rev. Clin. Pharmacol. 6:651-662.
De Kimpe et al. (1995) "The cell wall components peptidoglycan and lipoteichoic acid from *Staphylococcus aureus* act in synergy to cause shock and multiple organ failure," Proc. Natl. Acad. Sci. USA 92:10359-10363.
Depil et al. (2006) "Peptide-binding assays and HLA II transgenic Abeta degrees mice are consistent and complementary tools for identifying HLA II-restricted peptides," Vaccine 24:2225-2229.
Donlan et al. (2002) "Biofilms: survival mechanisms of clinically relevant microorganisms," Clin. Microbiol. Rev. 15:167-193.
Doytchinova et al. (2006) "Class I T-cell epitope prediction: improvements using a combination of proteasome cleavage, TAP affinity, and MHC binding," Mol. Immunol. 43(13):2037-2044.
Fedorov et al. (2003) "Purification and some properties of lysostaphin, a glycylglycine endopeptidase from the culture liquid of Staphylococcus simulans biovar staphylolyticus," Biochemistry (Moscow). 68:50-53.
Fernandez et al. (1999) "Comparison of efficacies of oral levofloxacin and oral ciprofloxacin in a rabbit model of a staphylococcal abscess," Antimicrob. Agent Chemother. 43:667-671.
Firczuk et al. (2005) "Crystal structures of active LytM," J. Mol. Biol. 354:578-590.
Foster (2005) "Immune evasion by staphylococci," Nat. Rev. Microbial. 3:948-958.
Gasser et al. (Feb. 2013) "Pichia pastoris: protein production host and model organism for biomedical research," Future Macrobiol. 8:191-208.
Gisby et al. (2000) "Efficacy of a new cream formulation of mupirocin: comparison with oral and topical agents in experimental skin infections," Antimicrob. Agents Chemother. 44:255-260.
Godin et al. (2005) "A new approach for treatment of deep skin infections by an ethosomal antibiotic preparation: an in vivo study," J. Antimicrob. Chemother. 55:989-994.
Goldberg et al. (1967) "Studies in experimental staphylococcal endocarditis in dogs. VI. Treatment with lysostaphin," Antimicrob. Agents Chemother. 7:45-53.
Gordon et al. (2008) "Pathogenesis of Methicillin-Resistant *Staphylococcus aureus* Infection," Clin. Infect. Dis. 46 (Suppl 5):S350-S359.
Gossen et al. (1992) "Tight control of gene expression in mammalian cells by tetracycline-responsive promoters," Proc. Natl. Acad. Sci. USA 89:5547-5551.
Gossen et al. (1994) "Control of gene activity in higher eukaryotic cells by prokaryotic regulatory elements," Trends Biotech. 12:58-62.
Grigoryan et al. (2006) "Ultra-Fast Evaluation of Protein Energies Directly from Sequence," PLoS Comput. Biol. 2 (6):e63. pp. 0551-0563.
Grigoryan et al. (2009) "Design of protein-interaction specificity gives selective bZIP-binding peptides," Nature. 458:859-864.
Hiramatsu et al. (2001) "The emergence and evolution of methicillin-resistant *Staphylococcus aureus*," Trends Microbiol. 9:486-493.
Hornak et al. (2006) "Comparison of multiple Amber force fields and development of improved protein backbone parameters," Proteins 65:712-725.
Huang et al. (Mar. 27, 2013) "Site-specific N-glycosylation of caprine lysostaphin restricts its bacteriolytic activity toward *Staphylococcus aureus*," Anim Biotechnol. 24(2):129-147.
Ito et al. (1996) "HLA-DR4-Ie chimeric class II transgenic, murine class II-deficient mice are susceptible to experimental allergic encephalomyelitis," J. Exp. Med. 183:2635-2644.
Kazakova et al. (2005) "A clone of methicillin-resistant *Staphylococcus aureus* among professional football players," New Engl. J. Med. 352:468-475.
Kernodle et al. (1994) "Comparative prophylactic efficacies of ciprofloxacin, ofloxacin, cefazolin, and vancomycin in experimental model of staphylococcal wound infection," Antimicrob. Agents Chemother. 38:1325-1330.
Kokai-Kun (2012) "Lysostaphin: A Silver Bullet for Staph," Ch. 10 In; Antimicrobial Drug Discovery: Emerging Strategies. Eds.: Tegos et al. pp. 147-165.
Kokai-Kun et al. (2007) "Lysostaphin as a treatment for systemic *Staphylococcus aureus* infection in a mouse model," J. Antimicrob. Ther. 60:1051-1059.
Kokai-Kun et al. (2009) "Lysostaphin eradicates established *Staphylococcus aureus* biofilms in jugular vein catheterized mice," J. Antimicrob. Ther. 64:94-100.
Koren et al. (2007) "Clinical validation of the 'in silico' prediction of immunogenicity of a human recombinant therapeutic protein," Clin. Immunol. 124:26-32.
Krivov et al. (2009) "Improved prediction of protein side-chain conformations with SCWRL4," Proteins: Struct. Funct. Bioinform. 77:778-795.
Kusuma et al. (2005) "Comparison of four methods for determining lysostaphin susceptibility of various strains of *Staphylococcus aureus*," Antimicrob. Agents Chemother. 49:3256-3263.
Lietha et al.(2001) "Crystal structures of NK1-heparin complexes reveal the basis for NK1 activity and enable engineering of potent agonists of the MET receptor," EMBO J. 20:5543-5555.
Lippow et al. (2007) "Progress in computational protein design," Curr. Opin. Biotechnol. 18:305-311.
Liu et al. (1997) "Removal of endotoxin from recombinant protein preparations," Clin. Biochem. 30:455-463.
Lovell et al. (2000) "The penultimate rotamer library," Proteins. 40:389-408.
Lowy (2003) "Antimicrobial resistance: the example of *Staphylococcus aureus*," J. Clin. Invest. 111:1265-1273.
Lu et al. (2006) "Cell wall-targeting domain of glycylglycine endopeptidase distinguishes among peptidoglycan cross-bridges," J. Biol. Chem. 281:549-558.

* cited by examiner

```
                   10        20        30        40        50        60
                    |         |         |         |         |         |
Flex 8     AATHEHSAQWLGNYKKGYGYGPYPLGINGGMHYGVDFFMNEGTPVKAISSGKIVEAGWSN
Rigid 38   AATHEHSAQWLGNYKKGYGYGPYPLGINGGMHYGVDFFMNEGTPVKAISSGKIVEAGWSN
Rigid 18   AATHEHSAQWLGNYKKGYGYGPYPLGINGGMHYGVDFFMNEGTPVKAISSGKIVEAGWSN
Flex 6     AATHEHSAQWLGNYKKGYGYGPYPLGINGGMHYGVDFFMNEGTPVKAISSGKIVEAGWSN
Flex 31    AATHEHSAQWLGNYKKGYGYGPYPLGINGGMHYGVDFFMNEGTPVKAISSGKIVEAGWSN
Flex 10    AATHEHSAQWLGNYKKGYGYGPYPLGINGGMHYGVDFFMNEGTPVKAISSGKIVEAGWSN
Flex 32    AATHEHSAQWLGNYKKGYGYGPYPLGINGGMHYGVDFFMNEGTPVKAISSGKIVEAGWSN
Rigid 17   AATHEHSAQWLGNYKKGYGYGPYPLGINGGMHYGVDFFMNEGTPVHAISSGKIVEAGWSN
Rigid 37   AATHEHSAQWLGNYKKGYGYGPYPLGINGGMHYGVDFFMNEGTPVHAISSGKIVEAGWSN
Rigid 21   AATHEHSAQWLGNYKKGYGYGPYPLGINGGMHYGVDFFMNEGTPVKAISSGKIVEAGWSN
Rigid 41   AATHEHSAQWLGNYKKGYGYGPYPLGINGGMHYGVDFFMNEGTPVKAISSGKIVEAGWSN
Rigid 23   AATHEHSAQWLGNYKKGYGYGPYPLGINGGMHYGVDFFMNEGTPVKAISSGKIVEAGWSN
Rigid 43   AATHEHSAQWLGNYKKGYGYGPYPLGINGGMHYGVDFFMNEGTPVKAISSGKIVEAGWSN
Rigid 19   AATHEHSAQWLGNYKKGYGYGPYPLGINGGMHYGVDFFMNEGTPVKAISSGKIVEAGWSN
Rigid 39   AATHEHSAQWLGNYKKGYGYGPYPLGINGGMHYGVDFFMNEGTPVKAISSGKIVEAGWSN
Rigid 20   AATHEHSAQWLGNYKKGYGYGPYPLGINGGMHYGVDFFMNEGTPVKAISSGKIVEAGWSN
Rigid 40   AATHEHSAQWLGNYKKGYGYGPYPLGINGGMHYGVDFFMNEGTPVKAISSGKIVEAGWSN
Rigid 22   AATHEHSAQWLGNYKKGYGYGPYPLGINGGMHYGVDFFMNEGTPVKAISSGKIVEAGWSN
Rigid 42   AATHEHSAQWLGNYKKGYGYGPYPLGINGGMHYGVDFFMNEGTPVKAISSGKIVEAGWSN
Flex 5     AATHEHSAQWLGNYKKGYGYGPYPLGINGGMHYGVDFFMNEGTPVKAISSGKIVEAGWSN
Flex 7     AATHEHSAQWLGNYKKGYGYGPYPLGINGGMHYGVDFFMNEGTPVKAISSGKIVEAGWSN
Flex 9     AATHEHSAQWLGNYKKGYGYGPYPLGINGGMHYGVDFFMNEGTPVKAISSGKIVEAGWSN
Flex 3     AATHEHSAQWLNNYKKGYGYGPYPLGINGGMHYGVDFFMNEGTPVKAISSGKIVEAGWSN
Flex 30    AATHEHSAQWLNNYKKGYGYGPYPLGINGGMHYGVDFFMNEGTPVKAISSGKIVEAGWSN
Flex 11    AATHEHSAQWLNHYKKGYGYGPYPLGINGGMHYGVDFFMNEGTPVKAISSGKIVEAGWSN
Flex 33    AATHEHSAQWLNHYKKGYGYGPYPLGINGGMHYGVDFFMNEGTPVKAISSGKIVEAGWSN
Flex 12    AATHEHSAQWLNHYKKGYGYGPYPLGINGGMHYGVDFFMNEGTPVKAISSGKIVEAGWSN
Flex 34    AATHEHSAQWLNHYKKGYGYGPYPLGINGGMHYGVDFFMNEGTPVKAISSGKIVEAGWSN
Flex 2     AATHEHSAQWLNNYKKGYGYGPYPLGINGGMHYGVDFFMNEGTPVKAISSGKIVEAGWSN
Flex 29    AATHEHSAQWLNNYKKGYGYGPYPLGINGGMHYGVDFFMNEGTPVKAISSGKIVEAGWSN
Flex 0     AATHEHSAQWLNNYKKGYGYGPYPLGINGGMHYGVDFFMNEGTPVKAISSGKIVEAGWSN
Flex 1     AATHEHSAQWLNNYKKGYGYGPYPLGINGGMHYGVDFFMNEGTPVHAISSGKIVEAGWSN
Flex 28    AATHEHSAQWLNNYKKGYGYGPYPLGINGGMHYGVDFFMNEGTPVHAISSGKIVEAGWSN
Rigid 24   AATHEHSAQWLNHYKKGYGYGPYPLGINGGMHYGVDFFMNIGTPVHAISSGKIVEAGWSN
Rigid 44   AATHEHSAQWLNHYKKGYGYGPYPLGINGGMHYGVDFFMNIGTPVHAISSGKIVEAGWSN
Rigid 26   AATHEHSAQWLNHYKKGYGYGPYPLGINGGMHYGVDFFMNIGTPVHAISSGKIVEAGWSN
Rigid 46   AATHEHSAQWLNHYKKGYGYGPYPLGINGGMHYGVDFFMNIGTPVHAISSGKIVEAGWSN
Rigid 15   AATHEHSAQWLNNYKKGYGYGPYPLGINGGMHYGVDFFMNIGTPVHAISSGKIVEAGWSN
Rigid 35   AATHEHSAQWLNNYKKGYGYGPYPLGINGGMHYGVDFFMNIGTPVHAISSGKIVEAGWSN
Flex 4     AATHEHSAQWLNNYKKGYGYGPYPLGINGGMHYGVDFFMNIGTPVHAISSGKIVEAGWSN
Rigid 25   AATHEHSAQWLNHYKKGYGYGPYPLGINGGMHYGVDFFMNIGTPVHAISSGKIVEAGWSN
Rigid 45   AATHEHSAQWLNHYKKGYGYGPYPLGINGGMHYGVDFFMNIGTPVHAISSGKIVEAGWSN
Rigid 27   AATHEHSAQWLNHYKKGYGYGPYPLGINGGMHYGVDFFMNIGTPVHAISSGKIVEAGWSN
Rigid 47   AATHEHSAQWLNHYKKGYGYGPYPLGINGGMHYGVDFFMNIGTPVHAISSGKIVEAGWSN
Rigid 16   AATHEHSAQWLNNYKKGYGYGPYPLGINGGMHYGVDFFMNIGTPVHAISSGKIVEAGWSN
Rigid 36   AATHEHSAQWLNNYKKGYGYGPYPLGINGGMHYGVDFFMNIGTPVHAISSGKIVEAGWSN
Flex 13    AATHEHSAQWLNNYKKGYGYGPYPLGINGGMHYGVDFFMNEGTPVKAISSGKIVEAGWSN
Rigid 14   AATHEHSAQWLNNYKKGYGYGPYPLGINGGMHYGVDFFMNEGTPVKAISSGKIVEAGWSN
           **********.:*****************************.****:*************
```

FIG. 1A

```
                    70        80        90       100       110       120
                    |         |         |         |         |         |
Flex 8     YGGGNQIGLIENDGVHRQWYMHMSKYNVKVGDYVEAGQQIGWSGSTGYSTAPHLHFQRMV
Rigid 38   YGGGNQIGLIENDGVHRQWYMHMSKYNVKVGDYVEAGQQIGWSGSTGYSTAPHLHFQRMV
Rigid 18   YGGGNQIGLIENDGVHRQWYMHMSKYNVKVGDYVEAGQQIGWSGSTGYSTAPHLHFQTMV
Flex 6     YGGGNQIGLIENDGVHRQWYMHLSKYNVKVGDYVEAGQQIGWSGSTGYSTAPHLHFQTMV
Flex 31    YGGGNQIGLIENDGVHRQWYMHLSKYNVKVGDYVEAGQQIGWSGSTGYSTAPHLHFQRMV
Flex 10    YGGGNQIGLIENDGVHRQWYMHLSKYNVKVGDHVEAGQQIGWSGSTGYSTAPHLHFQTMV
Flex 32    YGGGNQIGLIENDGVHRQWYMHLSKYNVKVGDHVEAGQQIGWSGSTGYSTAPHLHFQRMV
Rigid 17   YGGGNQIGLIENDGVHRQWYMHMSKYNVKVGDHVEAGQIIGWSGSTGYSTAPHLHFQTMV
Rigid 37   YGGGNQIGLIENDGVHRQWYMHMSKYNVKVGDHVEAGQIIGWSGSTGYSTAPHLHFQRMV
Rigid 21   YGGGNQIGLIENDGVHRQWYMHMSKYNVKVGDHVEAGQIIGWSGSTGYSTAPHLHFQTMV
Rigid 41   YGGGNQIGLIENDGVHRQWYMHMSKYNVKVGDHVEAGQIIGWSGSTGYSTAPHLHFQRMV
Rigid 23   YGGGNQIGLIENDGVHRQWYMHLSKYNVKVGDHVEAGQIIGWSGSTGYSTAPHLHFQTMV
Rigid 43   YGGGNQIGLIENDGVHRQWYMHLSKYNVKVGDHVEAGQIIGWSGSTGYSTAPHLHFQRMV
Rigid 19   YGGGNQIGLIENDGVHRQWYMHMSKYNVKVGDYVEAGQIIGWSGSTGYSTAPHLHFQTMV
Rigid 39   YGGGNQIGLIENDGVHRQWYMHMSKYNVKVGDYVEAGQIIGWSGSTGYSTAPHLHFQRMV
Rigid 20   YGGGNQIGLIENDGVHRQWYMHMSKYNVKVGDYVKAGQIIGWSGSTGYSTAPHLHFQTMV
Rigid 40   YGGGNQIGLIENDGVHRQWYMHMSKYNVKVGDYVKAGQIIGWSGSTGYSTAPHLHFQRMV
Rigid 22   YGGGNQIGLIENDGVHRQWYMHLSKYNVKVGDYVKAGQIIGWSGSTGYSTAPHLHFQTMV
Rigid 42   YGGGNQIGLIENDGVHRQWYMHLSKYNVKVGDYVKAGQIIGWSGSTGYSTAPHLHFQRMV
Flex 5     YGGGNQIGLIENDGVHRQWYMHLSKYNVKVGDYVKAGQQIGWSGSTGYSTAPHLHFQRMV
Flex 7     YGGGNQIGLIENDGVHRQWYMHMSKYNVKVGDYVKAGQQIGWSGSTGYSTAPHLHFQRMV
Flex 9     YGGGNQIGLIENDGVHRQWYMHLSKYNVKVGDYVKAGQIIGWSGSTGYSTAPHLHFQRMV
Flex 3     YGGGNQIGLIENDGVHRQWYMHLSKYNVKVGDHVEAGQQIGWSGSTGYSTAPHLHFQTMV
Flex 30    YGGGNQIGLIENDGVHRQWYMHLSKYNVKVGDHVEAGQQIGWSGSTGYSTAPHLHFQRMV
Flex 11    YGGGNQIGLIENDGVHRQWYMHLSKYNVKVGDYVEAGQQIGWSGSTGYSTAPHLHFQTMV
Flex 33    YGGGNQIGLIENDGVHRQWYMHLSKYNVKVGDYVEAGQQIGWSGSTGYSTAPHLHFQRMV
Flex 12    YGGGNQIGLIENDGVHRQWYMHLSKYNVKVGDHVEAGQQIGWSGSTGYSTAPHLHFQTMV
Flex 34    YGGGNQIGLIENDGVHRQWYMHLSKYNVKVGDHVEAGQQIGWSGSTGYSTAPHLHFQRMV
Flex 2     YGGGNQIGLIENDGVHRQWYMHLSKYNVKVGDYVEAGQQIGWSGSTGYSTAPHLHFQTMV
Flex 29    YGGGNQIGLIENDGVHRQWYMHLSKYNVKVGDYVEAGQQIGWSGSTGYSTAPHLHFQRMV
Flex 0     YGGGNQIGLIENDGVHRQWYMHLSKYNVKVGDYVKAGQQIGWSGSTGYSTAPHLHFQRMV
Flex 1     YGGGNQIGLIENDGVHRQWYMHLSKYNVKVGDYVKAGQIIGWSGSTGYSTAPHLHFQTMV
Flex 28    YGGGNQIGLIENDGVHRQWYMHLSKYNVKVGDYVKAGQIIGWSGSTGYSTAPHLHFQRMV
Rigid 24   YGGGNQIGLIENDGVHRQWYMHMSKYNVKVGDYVKAGQIIGWSGSTGYSTAPHLHFQTMV
Rigid 44   YGGGNQIGLIENDGVHRQWYMHMSKYNVKVGDYVKAGQIIGWSGSTGYSTAPHLHFQRMV
Rigid 26   YGGGNQIGLIENDGVHRQWYMHLSKYNVKVGDYVKAGQIIGWSGSTGYSTAPHLHFQTMV
Rigid 46   YGGGNQIGLIENDGVHRQWYMHLSKYNVKVGDYVKAGQIIGWSGSTGYSTAPHLHFQRMV
Rigid 15   YGGGNQIGLIENDGVHRQWYMHLSKYNVKVGDYVKAGQIIGWSGSTGYSTAPHLHFQTMV
Rigid 35   YGGGNQIGLIENDGVHRQWYMHLSKYNVKVGDYVKAGQIIGWSGSTGYSTAPHLHFQRMV
Flex 4     YGGGNQIGLIENDGVHRQWYMHLSKYNVKVGDYVKAGQQIGWSGSTGYSTAPHLHFQRMV
Rigid 25   YGGGNQIGLIENDGVHRQWYMHMSKYNVKVGDHVEAGQIIGWSGSTGYSTAPHLHFQTMV
Rigid 45   YGGGNQIGLIENDGVHRQWYMHMSKYNVKVGDHVEAGQIIGWSGSTGYSTAPHLHFQRMV
Rigid 27   YGGGNQIGLIENDGVHRQWYMHLSKYNVKVGDHVEAGQIIGWSGSTGYSTAPHLHFQTMV
Rigid 47   YGGGNQIGLIENDGVHRQWYMHLSKYNVKVGDHVEAGQIIGWSGSTGYSTAPHLHFQRMV
Rigid 16   YGGGNQIGLIENDGVHRQWYMHLSKYNVKVGDHVEAGQIIGWSGSTGYSTAPHLHFQTMV
Rigid 36   YGGGNQIGLIENDGVHRQWYMHLSKYNVKVGDHVEAGQIIGWSGSTGYSTAPHLHFQRMV
Flex 13    YGGGNQIGLIENDGVHRQWYMHLSKYNVKVGDYVKAGQIIGWSGSTGYSTAPHLHFQRMV
Rigid 14   YGGGNQIGLIENDGVHRQWYMHLSKYNVKVGDYVKAGQIIGWSGSTGYSTAPHLHFQRMV
           **********************:********:*:*** ***************** **
```

FIG. 1B

```
                 130       140       150       160       170       180
                   |         |         |         |         |         |
Flex 8    GDFGNPTAQDPMPFLKSAGYGKAGGTVTPTPNTGWKTNKYGTLYKSESASFTPNTDIITR
Rigid 38  NDFGNPTAQDPMPFLKSAGYGKAGGTVTPTPNTGWKTNKYGTLYKSESASFTPNTDIITR
Rigid 18  NDFGNPTAQDPMPFLKSAGYGKAGGTVTPTPNTGWKTNKYGTLYKSESASFTPNTDIITR
Flex 6    NDFGNPTAQDPMPFLKSAGYGKAGGTVTPTPNTGWKTNKYGTLYKSESASFTPNTDIITR
Flex 31   NDFGNPTAQDPMPFLKSAGYGKAGGTVTPTPNTGWKTNKYGTLYKSESASFTPNTDIITR
Flex 10   NDFGNPTAQDPMPFLKSAGYGKAGGTVTPTPNTGWKTNKYGTLYKSESASFTPNTDIITR
Flex 32   NDFGNPTAQDPMPFLKSAGYGKAGGTVTPTPNTGWKTNKYGTLYKSESASFTPNTDIITR
Rigid 17  NDFSNPTAQDPMPFLKSAGYGKAGGTVTPTPNTGWKTNKYGTLYKSESASFTPNTDIITR
Rigid 37  NDFSNPTAQDPMPFLKSAGYGKAGGTVTPTPNTGWKTNKYGTLYKSESASFTPNTDIITR
Rigid 21  NDFSNPTAQDPMPFLKSAGYGKAGGTVTPTPNTGWKTNKYGTLYKSESASFTPNTDIITR
Rigid 41  NDFSNPTAQDPMPFLKSAGYGKAGGTVTPTPNTGWKTNKYGTLYKSESASFTPNTDIITR
Rigid 23  NDFSNPTAQDPMPFLKSAGYGKAGGTVTPTPNTGWKTNKYGTLYKSESASFTPNTDIITR
Rigid 43  NDFSNPTAQDPMPFLKSAGYGKAGGTVTPTPNTGWKTNKYGTLYKSESASFTPNTDIITR
Rigid 19  NDFSNPTAQDPMPFLKSAGYGKAGGTVTPTPNTGWKTNKYGTLYKSESASFTPNTDIITR
Rigid 39  NDFSNPTAQDPMPFLKSAGYGKAGGTVTPTPNTGWKTNKYGTLYKSESASFTPNTDIITR
Rigid 20  NDFSNPTAQDPMPFLKSAGYGKAGGTVTPTPNTGWKTNKYGTLYKSESASFTPNTDIITR
Rigid 40  NDFSNPTAQDPMPFLKSAGYGKAGGTVTPTPNTGWKTNKYGTLYKSESASFTPNTDIITR
Rigid 22  NDFSNPTAQDPMPFLKSAGYGKAGGTVTPTPNTGWKTNKYGTLYKSESASFTPNTDIITR
Rigid 42  NDFSNPTAQDPMPFLKSAGYGKAGGTVTPTPNTGWKTNKYGTLYKSESASFTPNTDIITR
Flex 5    GDFSNPTAQDPMPFLKSAGYGKAGGTVTPTPNTGWKTNKYGTLYKSESASFTPNTDIITR
Flex 7    GDFSNPTAQDPMPFLKSAGYGKAGGTVTPTPNTGWKTNKYGTLYKSESASFTPNTDIITR
Flex 9    GDFSNPTAQDPMPFLKSAGYGKAGGTVTPTPNTGWKTNKYGTLYKSESASFTPNTDIITR
Flex 3    NDFSNPTAQDPMPFLKSAGYGKAGGTVTPTPNTGWKTNKYGTLYKSESASFTPNTDIITR
Flex 30   NDFSNPTAQDPMPFLKSAGYGKAGGTVTPTPNTGWKTNKYGTLYKSESASFTPNTDIITR
Flex 11   NDFSNPTAQDPMPFLKSAGYGKAGGTVTPTPNTGWKTNKYGTLYKSESASFTPNTDIITR
Flex 33   NDFSNPTAQDPMPFLKSAGYGKAGGTVTPTPNTGWKTNKYGTLYKSESASFTPNTDIITR
Flex 12   NDFSNPTAQDPMPFLKSAGYGKAGGTVTPTPNTGWKTNKYGTLYKSESASFTPNTDIITR
Flex 34   NDFSNPTAQDPMPFLKSAGYGKAGGTVTPTPNTGWKTNKYGTLYKSESASFTPNTDIITR
Flex 2    NDFSNPTAQDPMPFLKSAGYGKAGGTVTPTPNTGWKTNKYGTLYKSESASFTPNTDIITR
Flex 29   NDFSNPTAQDPMPFLKSAGYGKAGGTVTPTPNTGWKTNKYGTLYKSESASFTPNTDIITR
Flex 0    NDFSNPTAQDPMPFLKSAGYGKAGGTVTPTPNTGWKTNKYGTLYKSESASFTPNTDIITR
Flex 1    NDFGNPTAQDPMPFLKSAGYGKAGGTVTPTPNTGWKTNKYGTLYKSESASFTPNTDIITR
Flex 28   NDFGNPTAQDPMPFLKSAGYGKAGGTVTPTPNTGWKTNKYGTLYKSESASFTPNTDIITR
Rigid 24  NDFSNPTAQDPMPFLKSAGYGKAGGTVTPTPNTGWKTNKYGTLYKSESASFTPNTDIITR
Rigid 44  NDFSNPTAQDPMPFLKSAGYGKAGGTVTPTPNTGWKTNKYGTLYKSESASFTPNTDIITR
Rigid 26  NDFSNPTAQDPMPFLKSAGYGKAGGTVTPTPNTGWKTNKYGTLYKSESASFTPNTDIITR
Rigid 46  NDFSNPTAQDPMPFLKSAGYGKAGGTVTPTPNTGWKTNKYGTLYKSESASFTPNTDIITR
Rigid 15  NDFSNPTAQDPMPFLKSAGYGKAGGTVTPTPNTGWKTNKYGTLYKSESASFTPNTDIITR
Rigid 35  NDFSNPTAQDPMPFLKSAGYGKAGGTVTPTPNTGWKTNKYGTLYKSESASFTPNTDIITR
Flex 4    GDFSNPTAQDPMPFLKSAGYGKAGGTVTPTPNTGWKTNKYGTLYKSESASFTPNTDIITR
Rigid 25  NDFSNPTAQDPMPFLKSAGYGKAGGTVTPTPNTGWKTNKYGTLYKSESASFTPNTDIITR
Rigid 45  NDFSNPTAQDPMPFLKSAGYGKAGGTVTPTPNTGWKTNKYGTLYKSESASFTPNTDIITR
Rigid 27  NDFSNPTAQDPMPFLKSAGYGKAGGTVTPTPNTGWKTNKYGTLYKSESASFTPNTDIITR
Rigid 47  NDFSNPTAQDPMPFLKSAGYGKAGGTVTPTPNTGWKTNKYGTLYKSESASFTPNTDIITR
Rigid 16  NDFSNPTAQDPMPFLKSAGYGKAGGTVTPTPNTGWKTNKYGTLYKSESASFTPNTDIITR
Rigid 36  NDFSNPTAQDPMPFLKSAGYGKAGGTVTPTPNTGWKTNKYGTLYKSESASFTPNTDIITR
Flex 13   NDFSNPTAQDPMPFLKSAGYGKAGGTVTPTPNTGWKTNKYGTLYKSESASFTPNTDIITR
Rigid 14  NDFSNPTAQDPMPFLKSAGYGKAGGTVTPTPNTGWKTNKYGTLYKSESASFTPNTDIITR
          .**.********************************************************
```

FIG. 1C

```
              190       200       210       220       230       240
               |         |         |         |         |         |
Flex 8     TTGPFRSMPQSGVLKAGQTIHYDEVMKQDGHVWVGYTGNSGQRIYLPVRTWNKSTNTLGV
Rigid 38   TTGPFRSMPQSGVLKAGQTIHYDEVMKQDGHVWVGYTGNSGQRIYLPVRTWNKSTNTLGV
Rigid 18   TTGPFRSMPQSGVLKAGQTIHYDEVMKQDGHVWVGYTGNSGQRIYLPVRTWNKSTNTLGV
Flex 6     TTGPFRSMPQSGVLKAGQTIHYDEVMKQDGHVWVGYTGNSGQRIYLPVRTWNKSTNTLGV
Flex 31    TTGPFRSMPQSGVLKAGQTIHYDEVMKQDGHVWVGYTGNSGQRIYLPVRTWNKSTNTLGV
Flex 10    TTGPFRSMPQSGVLKAGQTIHYDEVMKQDGHVWVGYTGNSGQRIYLPVRTWNKSTNTLGV
Flex 32    TTGPFRSMPQSGVLKAGQTIHYDEVMKQDGHVWVGYTGNSGQRIYLPVRTWNKSTNTLGV
Rigid 17   TTGPFRSMPQSGVLKAGQTIHYDEVMKQDGHVWVGYTGNSGQRIYLPVRTWNKSTNTLGV
Rigid 37   TTGPFRSMPQSGVLKAGQTIHYDEVMKQDGHVWVGYTGNSGQRIYLPVRTWNKSTNTLGV
Rigid 21   TTGPFRSMPQSGVLKAGQTIHYDEVMKQDGHVWVGYTGNSGQRIYLPVRTWNKSTNTLGV
Rigid 41   TTGPFRSMPQSGVLKAGQTIHYDEVMKQDGHVWVGYTGNSGQRIYLPVRTWNKSTNTLGV
Rigid 23   TTGPFRSMPQSGVLKAGQTIHYDEVMKQDGHVWVGYTGNSGQRIYLPVRTWNKSTNTLGV
Rigid 43   TTGPFRSMPQSGVLKAGQTIHYDEVMKQDGHVWVGYTGNSGQRIYLPVRTWNKSTNTLGV
Rigid 19   TTGPFRSMPQSGVLKAGQTIHYDEVMKQDGHVWVGYTGNSGQRIYLPVRTWNKSTNTLGV
Rigid 39   TTGPFRSMPQSGVLKAGQTIHYDEVMKQDGHVWVGYTGNSGQRIYLPVRTWNKSTNTLGV
Rigid 20   TTGPFRSMPQSGVLKAGQTIHYDEVMKQDGHVWVGYTGNSGQRIYLPVRTWNKSTNTLGV
Rigid 40   TTGPFRSMPQSGVLKAGQTIHYDEVMKQDGHVWVGYTGNSGQRIYLPVRTWNKSTNTLGV
Rigid 22   TTGPFRSMPQSGVLKAGQTIHYDEVMKQDGHVWVGYTGNSGQRIYLPVRTWNKSTNTLGV
Rigid 42   TTGPFRSMPQSGVLKAGQTIHYDEVMKQDGHVWVGYTGNSGQRIYLPVRTWNKSTNTLGV
Flex 5     TTGPFRSMPQSGVLKAGQTIHYDEVMKQDGHVWVGYTGNSGQRIYLPVRTWNKSTNTLGV
Flex 7     TTGPFRSMPQSGVLKAGQTIHYDEVMKQDGHVWVGYTGNSGQRIYLPVRTWNKSTNTLGV
Flex 9     TTGPFRSMPQSGVLKAGQTIHYDEVMKQDGHVWVGYTGNSGQRIYLPVRTWNKSTNTLGV
Flex 3     TTGPFRSMPQSGVLKAGQTIHYDEVMKQDGHVWVGYTGNSGQRIYLPVRTWNKSTNTLGV
Flex 30    TTGPFRSMPQSGVLKAGQTIHYDEVMKQDGHVWVGYTGNSGQRIYLPVRTWNKSTNTLGV
Flex 11    TTGPFRSMPQSGVLKAGQTIHYDEVMKQDGHVWVGYTGNSGQRIYLPVRTWNKSTNTLGV
Flex 33    TTGPFRSMPQSGVLKAGQTIHYDEVMKQDGHVWVGYTGNSGQRIYLPVRTWNKSTNTLGV
Flex 12    TTGPFRSMPQSGVLKAGQTIHYDEVMKQDGHVWVGYTGNSGQRIYLPVRTWNKSTNTLGV
Flex 34    TTGPFRSMPQSGVLKAGQTIHYDEVMKQDGHVWVGYTGNSGQRIYLPVRTWNKSTNTLGV
Flex 2     TTGPFRSMPQSGVLKAGQTIHYDEVMKQDGHVWVGYTGNSGQRIYLPVRTWNKSTNTLGV
Flex 29    TTGPFRSMPQSGVLKAGQTIHYDEVMKQDGHVWVGYTGNSGQRIYLPVRTWNKSTNTLGV
Flex 0     TTGPFRSMPQSGVLKAGQTIHYDEVMKQDGHVWVGYTGNSGQRIYLPVRTWNKSTNTLGV
Flex 1     TTGPFRSMPQSGVLKAGQTIHYDEVMKQDGHVWVGYTGNSGQRIYLPVRTWNKSTNTLGV
Flex 28    TTGPFRSMPQSGVLKAGQTIHYDEVMKQDGHVWVGYTGNSGQRIYLPVRTWNKSTNTLGV
Rigid 24   TTGPFRSMPQSGVLKAGQTIHYDEVMKQDGHVWVGYTGNSGQRIYLPVRTWNKSTNTLGV
Rigid 44   TTGPFRSMPQSGVLKAGQTIHYDEVMKQDGHVWVGYTGNSGQRIYLPVRTWNKSTNTLGV
Rigid 26   TTGPFRSMPQSGVLKAGQTIHYDEVMKQDGHVWVGYTGNSGQRIYLPVRTWNKSTNTLGV
Rigid 46   TTGPFRSMPQSGVLKAGQTIHYDEVMKQDGHVWVGYTGNSGQRIYLPVRTWNKSTNTLGV
Rigid 15   TTGPFRSMPQSGVLKAGQTIHYDEVMKQDGHVWVGYTGNSGQRIYLPVRTWNKSTNTLGV
Rigid 35   TTGPFRSMPQSGVLKAGQTIHYDEVMKQDGHVWVGYTGNSGQRIYLPVRTWNKSTNTLGV
Flex 4      TTGPFRSMPQSGVLKAGQTIHYDEVMKQDGHVWVGYTGNSGQRIYLPVRTWNKSTNTLGV
Rigid 25   TTGPFRSMPQSGVLKAGQTIHYDEVMKQDGHVWVGYTGNSGQRIYLPVRTWNKSTNTLGV
Rigid 45   TTGPFRSMPQSGVLKAGQTIHYDEVMKQDGHVWVGYTGNSGQRIYLPVRTWNKSTNTLGV
Rigid 27   TTGPFRSMPQSGVLKAGQTIHYDEVMKQDGHVWVGYTGNSGQRIYLPVRTWNKSTNTLGV
Rigid 47   TTGPFRSMPQSGVLKAGQTIHYDEVMKQDGHVWVGYTGNSGQRIYLPVRTWNKSTNTLGV
Rigid 16   TTGPFRSMPQSGVLKAGQTIHYDEVMKQDGHVWVGYTGNSGQRIYLPVRTWNKSTNTLGV
Rigid 36   TTGPFRSMPQSGVLKAGQTIHYDEVMKQDGHVWVGYTGNSGQRIYLPVRTWNKSTNTLGV
Flex 13    TTGPFRSMPQSGVLKAGQTIHYDEVMKQDGHVWVGYTGNSGQRIYLPVRTWNKSTNTLGV
Rigid 14   TTGPFRSMPQSGVLKAGQTIHYDEVMKQDGHVWVGYTGNSGQRIYLPVRTWNKSTNTLGV
           ************************************************************
```

*FIG. 1D*

```
Flex 8      LWGTIK (SEQ ID NO:1)
Rigid 38    LWGTIK (SEQ ID NO:2)
Rigid 18    LWGTIK (SEQ ID NO:3)
Flex 6      LWGTIK (SEQ ID NO:4)
Flex 31     LWGTIK (SEQ ID NO:5)
Flex 10     LWGTIK (SEQ ID NO:6)
Flex 32     LWGTIK (SEQ ID NO:7)
Rigid 17    LWGTIK (SEQ ID NO:8)
Rigid 37    LWGTIK (SEQ ID NO:9)
Rigid 21    LWGTIK (SEQ ID NO:10)
Rigid 41    LWGTIK (SEQ ID NO:11)
Rigid 23    LWGTIK (SEQ ID NO:12)
Rigid 43    LWGTIK (SEQ ID NO:13)
Rigid 19    LWGTIK (SEQ ID NO:14)
Rigid 39    LWGTIK (SEQ ID NO:15)
Rigid 20    LWGTIK (SEQ ID NO:16)
Rigid 40    LWGTIK (SEQ ID NO:17)
Rigid 22    LWGTIK (SEQ ID NO:18)
Rigid 42    LWGTIK (SEQ ID NO:19)
Flex 5      LWGTIK (SEQ ID NO:20)
Flex 7      LWGTIK (SEQ ID NO:21)
Flex 9      LWGTIK (SEQ ID NO:22)
Flex 3      LWGTIK (SEQ ID NO:23)
Flex 30     LWGTIK (SEQ ID NO:24)
Flex 11     LWGTIK (SEQ ID NO:25)
Flex 33     LWGTIK (SEQ ID NO:26)
Flex 12     LWGTIK (SEQ ID NO:27)
Flex 34     LWGTIK (SEQ ID NO:28)
Flex 2      LWGTIK (SEQ ID NO:29)
Flex 29     LWGTIK (SEQ ID NO:30)
Flex 0      LWGTIK (SEQ ID NO:31)
Flex 1      LWGTIK (SEQ ID NO:32)
Flex 28     LWGTIK (SEQ ID NO:33)
Rigid 24    LWGTIK (SEQ ID NO:34)
Rigid 44    LWGTIK (SEQ ID NO:35)
Rigid 26    LWGTIK (SEQ ID NO:36)
Rigid 46    LWGTIK (SEQ ID NO:37)
Rigid 15    LWGTIK (SEQ ID NO:38)
Rigid 35    LWGTIK (SEQ ID NO:39)
Flex 4      LWGTIK (SEQ ID NO:40)
Rigid 25    LWGTIK (SEQ ID NO:41)
Rigid 45    LWGTIK (SEQ ID NO:42)
Rigid 27    LWGTIK (SEQ ID NO:43)
Rigid 47    LWGTIK (SEQ ID NO:44)
Rigid 16    LWGTIK (SEQ ID NO:45)
Rigid 36    LWGTIK (SEQ ID NO:46)
Flex 13     LWGTIK (SEQ ID NO:47)
Rigid 14    LWGTIK (SEQ ID NO:48)
            ******
```

FIG. 1E

DEIMMUNIZED LYSOSTAPHIN AND METHODS OF USE

INTRODUCTION

This application is a 35 U.S.C. § 371 filing of International Application No. PCT/US2015/030765, filed May 14, 2015, which claims the benefit of priority from U.S. Patent Application Ser. No. 61/993,056, filed May 14, 2014, U.S. Patent Application Ser. No. 62/003,256, filed May 27, 2014, U.S. Patent Application Ser. No. 62/115,326, filed Feb. 12, 2015 and U.S. Patent Application Ser. No. 62/155,079, filed Apr. 30, 2015, the contents of which is incorporated herein by reference in their entireties.

This invention was made with government support under Grant Nos. 1R21AI098122 awarded by the National Institutes of Health. The government has certain rights in the invention.

BACKGROUND

*Staphylococcus aureus* colonizes the skin and mucosal membranes of humans and animals, and together with the other members of the genus *Staphylococcus*, has been implicated in a diverse array of infections. *S. aureus* contains many virulence factors including surface proteins designated as "microbial surface components recognizing adhesive matrix molecules," which facilitate attachment to surfaces and initiate infection (Gordon & Lowy (2008) *Clin. Infect. Dis.* 46:S350-5359). *S. aureus* can also form biofilms (Donlan & Costerton (2002) *Clin. Microbiol. Rev.* 15:167-193), which allow it to evade both the immune system and antibiotics. Most strains have a polysaccharide capsule and secrete a variety of enzymes that are used during infection to enhance bacterial spreading (Foster (2005) *Nat. Rev. Microbiol.* 3:948-958). *S. aureus* can also cause toxic shock syndrome, and studies have shown that the peptidoglycan and lipoteichoic acid of the *S. aureus* cell wall act together to cause toxic shock in rats (Kimpe, et al. (1995) *Proc. Natl. Acad. Sci. USA* 92:10359-10363).

Antibiotic resistance in staphylococci appeared after penicillin was first used for treatment of staphylococcal infections. This development of resistance, which was present in over 80% of clinical isolates by the late 1960s (Lowy (2003) *J. Clin. Invest.* 111:1265-1273), prompted the development of new, more potent drugs to combat the opportunistic pathogen. These efforts led to production of methicillin, a narrow spectrum penicillinase-resistant drug designed to alleviate the burden of staphylococcal infections. However, it took only a year for the first methicillin-resistant *S. aureus* (MRSA) clinical isolates to be discovered.

Initially, MRSA infections were only associated with prolonged hospital treatment and invasive surgical procedures, and were classified as Health Care-Acquired MRSA (HCA-MRSA). However, in recent years, MRSA has also emerged as a community-acquired infection (CA-MRSA), which affects groups with high-intensity physical contact, such as competitive athletes, military recruits, and children in daycare centers (Romano, et al. (2006) *J. Athl. Train.* 41:141-145; Kazakova, et al. (2005) *New Engl. J. Med.* 352:468-475; Zinderman, et al. (2004) *Emerg. Infect. Dis.* 10:941-944; Adcock, et al. (1998) *J. Infect. Dis.* 178:577-580).

The *S. aureus* cell wall is composed of alternating polysaccharide subunits of N-acetylglucosamine and N-acetylmuramic acid, wherein each N-acetylmuramic acid is connected to a peptide chain. Cross-linking of the peptidoglycan is achieved by four major penicillin-binding proteins (PBP1, 2, 3 and 4) that connect the muropeptide chains via pentaglycine interpeptide bridge. Methicillin resistance arose when *S. aureus* acquired the mecA gene, which encodes for penicillin-binding protein PBP2A that has transpeptidase activity but lower affinity for penicillin and β-lactam antibiotics. Resistant cells still produce PBPs, but given the expression of PBP2A, peptidoglycan synthesis continues in the presence of methicillin and other β-lactams (Hiramatsu, et al. (2001) *Trends Microbiol.* 9:486-493).

Lysostaphin is a glycyl-glycine zinc-dependent endopeptidase produced by *Staphylococcus simulans*, which selectively targets pentaglycine interpeptide cross-bridges. The gene for lysostaphin has been isolated and characterized. Genetic truncations have been made to remove the 36-residue signal Peptide and 224-residue long propeptide thereby facilitating fusion to either an initiating methionine for intracellular expression or an exogenous signal sequence, e.g., to permit the secretion of a single species of lysostaphin into the periplasmic space of *E. coli* (See, e.g., US 2005/0118159). The mature, 247-residue enzyme is composed of N-terminal catalytic domain (138 amino acids), which is connected to the C-terminal cell wall binding domain (92 amino acids) via an 18-residue linker (Lu, et al. (2013) *Antimicrob. Agents Chemother.* 57:1872-1881).

Lysostaphin has shown promise as a therapeutic agent for treatment of *S. aureus* infections. The protein has been shown to lyse staphylococcal strains (Schindler & Schuhardt (1964) *Proc. Natl. Acad. Sci. USA* 51:414421) and clinical isolates (Cropp & Harrison (1964) *Can. J. Microbiol.* 10:823-828), and demonstrated remarkable efficacy in animal models (Schuhardt & Schindler (1964) *J. Bacteriol.* 88:815-816; Schaffner, et al. (1967) *Yale J. Biol. Med.* 39:230-244; Goldberg, et al. (1967) *Antimicrob. Agents Chemother.* 7:45-53; Kokai-Kun, et al. (2007) *J. Antimicrob. Ther.* 60:1051-1059; Placencia, et al. (2009) *Ped. Res.* 65:420-424; Climo, et al. (1998) *Antimicrob. Agents Chemother.* 42:1355-60), including those of staphylococcal biofilms (Kokai-Kun, et al. (2009) *J. Antimicrob. Ther.* 64:94-100). In several of these studies, antibodies against lysostaphin were observed in animals subjected to the drug for a prolonged period of time (Climo, et al. (1998) *Antimicrob. Agents Chemother.* 42:1355-1360). Similarly, human clinical trials with intranasal lysostaphin indicated a slight elevation in anti-lysostaphin antibody titer (Kokai-Kun (2012) in *Antimicrobial Drug Discovery: Emerging Strategies* (Tegos & Mylonakis, eds) Ch. 10, 147-165).

In an attempt to improve pharmacokinetics and reduce immunogenicity, lysostaphin has been linked to branched polyethylene glycol (PEG). While PEGylation reduced immunoreactivity, PEGylation of the enzyme significantly reduced its activity (Walsh, et al. (2003) *Antimicrob. Agents Chemother.* 47:554-558). In addition, US 2008/0095756 describes the deimmunization of the cell wall binding domain of lysostaphin. However, variants with a deimmunized catalytic domain are not described.

SUMMARY OF THE INVENTION

This invention is a deimmunized lysostaphin having a mutation at one or more of Ser124, Ser122, Asn121, Arg118, Ile99, Lys95, Tyr93, Leu83, Lys46, Ile41, Asn13, Asn12 of SEQ ID NO:49. In one embodiment, the lysostaphin is aglycosylated. In another embodiment, the mutation is Ser124Gly, Ser122Asp, Asn121Gly, Arg118Thr, Ile99Gln, Lys95Glu, Tyr93His, Leu83Met, Lys46His, Ile41Glu, Asn13His, Asn12Gly, or a combination thereof. In a further embodiment, the deimmunized lysostaphin further includes one or more amino acid substitutions in the C-terminal binding domain. A pharmaceutical composition containing the deimmunized lysostaphin and an antibiotic is provided, as is a method preventing or treating a microbial infection.

BRIEF DESCRIPTION OF THE DRAWINGS

FIGS. 1A-1E show a sequence alignment of lysostaphin variants of the present invention.

FIG. 4A, Bacterial burden in the lungs of C57Bl/6 mice following infection with *S. aureus* and treatment with wild-type LST, variant Flex 5, variant Flex 9, or a PBS control. N=6 per group. FIG. 4B, HUMI mice (all humanized from a single donor) were immunized subcutaneously with either wild-type LST (WT), variant Flex 5, or variant Flex 9, and splenocytes were harvested and restimulated ex vivo with the same protein or DMSO. Proliferation was measured as uptake of tritiated thymidine. N=4 per group, pooled and measured in triplicate. FIG. 4C, Transgenic DR4 mice were immunized with multiple subcutaneous injections of wild-type LST. Following the final boost, mice were allowed to recover for 20 weeks, divided into two groups, and rechallenged with either wild-type LST or variant Flex 5. Splenocytes were harvested and restimulated ex vivo with the rechallenge protein or DMSO, and proliferation was measured as uptake of tritiated thymidine. N=5 per group, pooled and measured in triplicate. Statistical significance was assessed by one way ANOVA (FIG. 4A) or two way ANOVA (FIGS. 4B and 4C). *$P<0.05$; $P<0.01$; *$P<0.001$; ****$P<0.0001$.

DETAILED DESCRIPTION OF THE INVENTION

Figure 2:
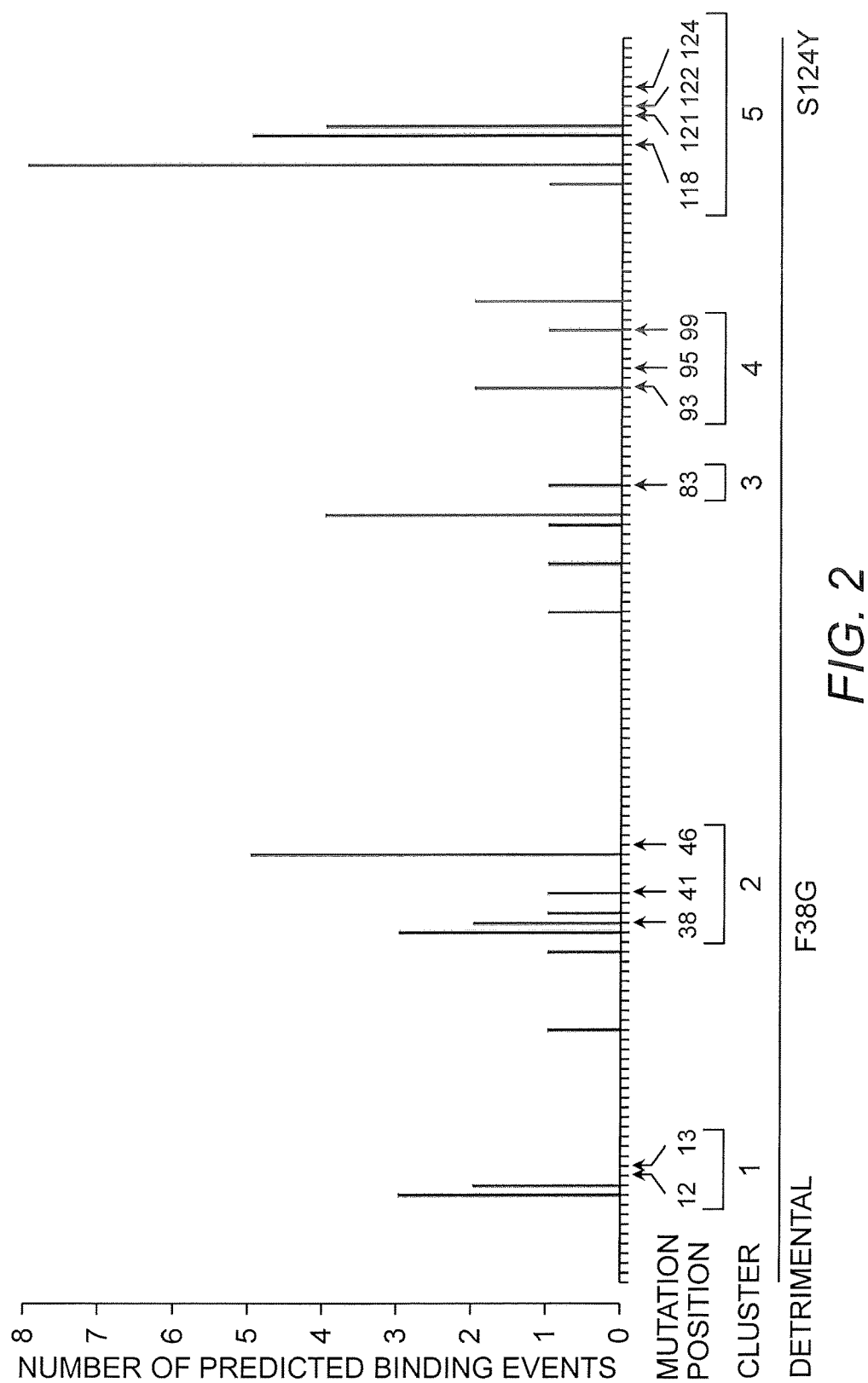
FIG. 2 shows an epitope map of the lysostaphin catalytic domain. The total number of predicted binding events is plotted against the lysostaphin primary sequence. Using EpiMatrix, epitopes were predicted for MHC II alleles DRB*0101, 0301, 0401, 0701, 0801, 1101, 1301, and 1501. The maximum score is 8 and represents an epitope that is predicted to bind all 8 alleles. Such an epitope was observed at position 116. The sites of EpiSweep mutations are indicated with arrows and residue numbers. Epitope groups are divided into five distinct clusters. Mutations found to be detrimental for lysostaphin expression and activity that were later dropped (Phe38Gly and Ser124Tyr) are also indicated.

It has now been shown that the catalytic domain of lysostaphin can be deimmunized without significantly altering enzymatic activity. In particular, EpiSweep analysis of lysostaphin was used to identify MHC II binding events. Deimmunized lysostaphin variants containing mutations in the catalytic domain were generated, expressed, purified and shown to have an activity level comparable to commercially-sourced lysostaphin. By combining mutations in the catalytic domain with mutations in the cell wall binding domain, this invention provides a fully deimmunized lysostaphin variant and methods of using the same to treat a microbial infection.

As used herein, the term "deimmunized" when used in reference to lysostaphin, relates to lysostaphin (e.g., lysostaphin variants, derivatives and/or homologues thereof), wherein the specific removal and/or modification of highly immunogenic regions or residues has occurred. The term "deimmunized" is well-known in the art and, among other things, has been employed for the removal of T-cell epitopes from other therapeutic molecules including antibodies (See, e.g., WO 98/52976 or WO 00/34317).

Humoral antibody formation requires the cooperation of helper T-cells with antigen-specific B-cells. To reduce immunogenicity of a molecule, one approach is to reduce the ability of the antigen to interact with and stimulate B-cells and/or reduce their ability to stimulate helper T-cells. The identification of B-cell epitopes is problematic, however, given the fact that they are of indeterminate length, and often dependent on the tertiary structure of the target antigen. In contrast, T cell epitopes are short (9-15 amino acid), linear peptides (See, e.g., Doytchinova & Flower (2006) *Mol. Immunol.* 43(13):2037-44). In addition, evidence suggests that reduction of T-cell activation is easier to achieve and has the ability to greatly impact antibody production (see, e.g., Tangri, et al. (2005) *J. Immunol.* 174:3187-3196). The amino acid sequences that include the antigenic determinants that stimulate T-cells are referred to as T-cell epitopes and are displayed in the context of major histocompatibility complex (MHC) molecules on antigen presenting cells. Altering the ability of T cell epitopes to bind MHC molecules (e.g., by inhibiting the binding of the epitope to the MHC molecule, altering the affinity between the epitope and the MHC molecule, altering the epitope in a manner such that the epitope's orientation is altered while within the binding region of the MHC molecule, or altering the epitope in such a way that its presentation by the MHC molecule is altered) has the potential to render the altered epitopes unable to or less able to stimulate an immunogenic response (e.g., stimulate helper T-cells and B cell responses). Accordingly, using the methods described herein, epitopes of lysostaphin were identified and subsequently altered in an effort to reduce the immunogenicity of lysostaphin and its ability to induce humoral antibody responses.

Thus, deimmunization involves the identification, modification and/or removal of T-cell epitopes, preferably helper T-cell epitopes. In this context, the term T-cell epitope relates to T-cell epitopes (i.e., small peptides) that are recognized by T-cells in the context of MHC class I and/or class II molecules. Methods for the identification of T-cell epitopes are known in the art (see, e.g., WO 98/52976, WO 00/34317, and US 2004/0180386). Various methods of identification include, but are not limited to, peptide threading, peptide-MHC binding, human T-cell assays, analysis of cytokine expression patterns, ELISPOT assays, class II tetramer epitope mapping, search of MHC-binding motif databases and the additional removal/modification of T-cell epitopes. In particular embodiments, a structure-guided deimmunization approach, such as that employed by the EpiSweep method, is used. EpiSweep integrates structure-based protein design, sequence-based protein deimmunization, and algorithms for finding the Pareto frontier of a design space (Parker, et al. (2013) J. Comput. Biol. 20:152-65).

Having identified T cell epitopes by application of the above-recited technologies, the epitopes can be eliminated, substituted and/or modified from lysostaphin or fragment(s) thereof (e.g., the catalytic domain) by one or more amino acid substitutions within an identified MHC binding peptide as further described herein. In some embodiments, one or more amino acid substitutions are generated that eliminate or greatly reduce binding to MHC class I and/or class II molecules, or alternatively, altering the MHC binding peptide to a sequence that retains its ability to bind MHC class I or class II molecules but fails to trigger T cell activation and/or proliferation.

Mature lysostaphin has been shown to have two functional domains, a C-terminal domain of 92 residues that binds the *S. aureus* outer cell wall and the N-terminal active site having endopeptidase activity (Baba & Schneewind (1996) *EMBO J.* 15:4789-4797). Lysostaphin has not been successfully crystallized in part due to the differing solvent characteristics of its two separate domains. However, using the in silico methods described herein, highly functional lysostaphin proteins, including various combinations of mutations, have been produced. Mutable amino acids at each position in the catalytic domain (except active site residues) were selected lysostaphin variants were produced that were predicted to have lower immunogenicity while retaining stability. Each mutation was evaluated for expression and activity. Only the mutations that were deemed satisfactory in both regards were selected, and the deimmunization process was repeated again. After the appropriate energy minimizations of the resulting plans, designs with the best predicted energy scores were chosen and experimentally tested. Lysostaphin variants that were capable of being expressed were then purified and further characterized for activity, stability and immunogenicity.

Accordingly, the present invention provides a variety of lysostaphin variants, including modification (e.g., mutations such as amino acid substitutions) of immunogenic epitopes, which retain activity while concurrently displaying reduced immunogenicity. As used herein, the term "lysostaphin" refers to amino acid sequence and/or nucleic acid sequence encoding full length lysostaphin or portion thereof, any lysostaphin mutant or variant (e.g., lysostaphin of any one of SEQ ID NOs: 1-48 or 218-220), any lysostaphin truncation (e.g., in which one or more amino acids have been removed from the protein's amino terminus, carboxy terminus, or both), and any recombinantly expressed lysostaphin protein, that retains the proteolytic ability, in vitro and in vivo, of proteolytic attack against glycine-containing bridges in the cell wall peptidoglycan of staphylococci. Lysostaphin variants (e.g., deimmunized lysostaphin described herein) may also be expressed in a truncated form. Modified full-length lysostaphin or lysostaphin variants may be generated by post-translational processing of the protein (either by enzymes present in a host cell strain or by means of enzymes or reagents introduced at any stage of the process) or by mutation of the structural gene. Lysostaphin variants, as describe herein, may include deletion, insertion, domain removal, point and replacement/substitution mutations.

The present invention is not limited to any particular lysostaphin variant. Indeed, a variety of variants are provided by the present invention including, but not limited to, those described in the Examples and depicted in FIGS. 1A-1E. In some embodiments, a lysostaphin variant has a single amino acid substitution (e.g., any one of the amino acid substitutions described herein) when compared with the wild-type sequence:

(SEQ ID NO: 49)
AATHEHSAQWLNNYKKGYGYGPYPLGINGGMHYGVDFFMNIGTPVKAISS

GKIVEAGWSNYGGGNQIGLIENDGVHRQWYMHLSKYNVKVGDYVKAGQII

GWSGSTGYSTAPHLHFQRMVNSFSNPTAQDPMPFLKSAGYGKAGGTVTPT

PNTGWKTNKYGTLYKSESASFTPNTDIITRTTGPFRSMPQSGVLKAGQTI

HYDEVMKQDGHVWVGYTGNSGQRIYLPVRTWNKSTNTLGVLWGTIK.

In some embodiments, a lysostaphin variant has two amino acid substitutions when compared with the wild-type sequence. In other embodiments, a lysostaphin variant has three amino acid substitutions when compared with the wild-type sequence. In further embodiments, a lysostaphin variant has four or more amino acid substitutions when compared with the wild-type sequence. In certain embodiments, a lysostaphin variant has one or more amino acid substitutions in the catalytic domain. In some embodiments, a lysostaphin mutant has a mutation at Ser124, Ser122, Asn121, Arg118, Ile99, Lys95, Tyr93, Leu83, Lys46, Ile41, Asn13, Asn12 or a combination thereof. In some embodiments, a lysostaphin variant has one or a combination of the following mutations: Ser124Gly, Ser122Asp, Asn121Gly, Arg118Thr, Ile99Gln, Lys95Glu, Tyr93His, Leu83Met, Lys46His, Ile41Glu, Asn13His, and Asn12Gly. In other embodiments, a lysostaphin variant also has one or more amino acid substitutions in the C-terminal binding domain. In some embodiments, a lysostaphin variant has a C-terminal binding domain mutation at Asn236, Arg186, Ala169, Ser166, Tyr160 or a combination thereof. In some embodiments, a lysostaphin variant has one or a combination of the following mutations in the C-terminal binding domain mutation: Asn236Asp, Arg186Thr, Ala169Gly, Ser166Asn and Tyr160His. Other suitable amino acid substitutions in the C-terminal binding domain include, but are not limited to those disclosed in US 2008/0095756.

Similarly, the present invention is not limited to any particular type of mutation. Mutations of this invention include, but not limited to, amino acid exchange(s), insertion(s), deletion(s), addition(s), substitution(s), inversion(s) and/or duplication(s). These mutations/modification(s) also include conservative and/or homologue amino acid exchange(s). Guidance concerning how to make phenotypically/functionally silent amino acid substitution has been described (see, e.g., Bowie (1990), *Science* 247:1306-1310).

The present invention also provides lysostaphin variants having an amino acid sequence that is at least 60%, more preferably at least 70%, more preferably at least 80%, more preferably 90%, more preferably at least 95% and most preferably 99% identical or homologous to the polypeptide sequences shown in FIG. 1 (SEQ ID NOs: 1-48) or in SEQ ID NO:218-220.

In some embodiments, a lysostaphin variant of the present invention elicits less than 90%, more preferably less than 80%, more preferably less than 70%, more preferably less than 60%, more preferably less than 50%, more preferably less than 40%, more preferably less than 30%, more preferably less than 20%, and even more preferably less than 10% of the immune response (e.g., as measured by anti-lysostaphin antibody titers) elicited by non-deimmunized lysostaphin.

In some embodiments, the present invention provides a plasmid harboring a nucleic acid sequence encoding deimmunized a lysostaphin variant. In certain embodiments, the plasmid is an expression vector harboring a nucleic acid sequence encoding a lysostaphin variant (e.g., that displays bactericidal activity and reduced immunogenicity and). In some embodiments, the lysostaphin variant is expressed as a fusion protein, e.g., fused to sequences that facilitate purification (e.g., histidine stretches). In some embodiments, an expression vector of the present invention harbors a nucleic acid sequence encoding a deimmunized lysostaphin variant having an amino acid sequence as set forth in SEQ ID NO:1-48 (FIGS. 1A-1E) or SEQ ID NO:218-220.

In addition to lysostaphin variant nucleic acids, a plasmid of this invention may also include regulatory sequences, e.g., promoters, transcriptional enhancers and/or sequences that allow for induced expression of lysostaphin variants. For example, one suitable inducible system is a tetracycline-regulated gene expression system (see, e.g., Gossen & Bujard (1992) *Proc. Natl. Acad. Sci. USA* 89:5547-5551; Gossen et al. (1994) *Trends Biotech.* 12:58-62). In some embodiments, the inducible system is an isopropyl-b-D-thiogalactoside (IPTG)-inducible promoter.

Using expression plasmids, the lysostaphin variant of this invention can be produced by a number of known methods. For example, the lysostaphin variant can be expressed and isolated from *Bacillus sphaericus* (U.S. Pat. No. 4,931,390); *Lactococcus lactis* NICE expression system (NIsin-Controlled gene Expression) (Mierau, et al. (2005) *Microb. Cell Fact.* 4:1-9); pET23b(+) and pBAD/Thio-TOPO *E. coli* expression systems (Szweda, et al. (2005) *J. Biotechnol.* 117:203-213); BL21 (DE-3) *E. coli* (Sharma, et al. (2006) *Prot. Exp. Purific.* 45:206-215); or *Pichia pastoris*, as described herein and elsewhere for the production of therapeutic proteins (Gasser, et al. (2013) *Future Microbiol.* 8:191-208; Walsh (2010) *Nature Biotechnol.* 28:917-924; Shekhar (2008) *Chem. Biol.* 15:201-202; Meyer, et al. (2008) *Bioproc. Internat.* 6:10-21). In particular embodiments, the lysostaphin variant of this invention is obtained by expression in *P. pastoris*, which is characterized with efficient and selective secretion, high protein titers, and high cell density cultivations (Vogl, et al. (2013) *Curr. Opin. Biotechnol.* 24:1094-1101). Furthermore, *P. pastoris* is considered as a safe (GRAS) organism, has several signal sequences that can be used for protein secretion, and has one of the strongest promoters known (AOX). Because it allows for protein secretion directly into media, *P. pastoris* greatly simplifies protein recovery and downstream purification.

The lysostaphin variants of this invention can be purified by a number of known methods. For example, due to its high positive charge, lysostaphin has been purified from bacterial hosts such as *S. simulans, B. sphaericus*, or *L. lactis* using a cation exchange step (Recsei, et al. (1990) supra; Mierau, et al. (2005) supra; Fedorov, et al. (2003) *Biochemistry* (Moscow) 68:50-53). When expressed in *E. coli*, lysostaphin has been purified using affinity chromatography (Szweda, et al. (2005) supra; Sharma, et al. (2006) supra).

Lysostaphin activity can be determined in several different ways: minimum inhibitory concentration (MIC), minimum bactericidal concentration (MBC), disk diffusion, and turbidity reduction (Kusuma & Kokai-Kun (2005) *Antimicrob. Agents Chemother.* 49:3256-3263). The MIC assay is performed to obtain the minimum concentration of lysostaphin that is necessary to prevent growth of *S. aureus* cells, while MBC assay is usually done after a MIC assay to determine the minimal concentration of the drug necessary to kill *S. aureus*. MIC assays are considered to be the golden standard of determining the value of a therapeutic. The disk diffusion assay is conducted to measure activity by determining the diameter of zone of clearance that is created when a lysostaphin-containing disk is placed on a lawn of *S. aureus* and allowed to diffuse into the plate media over time. The turbidity reduction assay involves measuring the decrease in optical absorbance of *S. aureus* culture over time as lysis of the cells progresses (Schindler & Schuhardt (1964) *Proc. Natl. Acad. Sci. USA* 51:414-421).

Protein stability can be determined using several different methods. Three well-established methods for measuring thermostability include, e.g., differential scanning calorimetry (DSC), differential scanning light scattering (DSLS), and differential scanning fluorimetry (DSF). All methods are based on determining the rate of protein unfolding with increasing temperature, which is a measure of protein stability. For instance, if a small increase in temperature results in protein unfolding, the protein is not considered to be very stable. DSC directly measures the heat absorption associated with thermal denaturation and has been proven to be sufficiently quantitative for evaluation of stability of protein therapeutics (Wen, et al. (2011) *J. Pharmaceut. Sci.* 101: 955-964). The DSLS method measures protein stability based on the assumption that proteins denature irreversibly as they are exposed to increasing temperatures. Using light-scattering, this method monitors the aggregation that occurs as a consequence of denaturation. In DSF, a fluorescent dye is used that fluoresces upon binding hydrophobic residues. As temperature increases, the protein starts to unfold and exposes the hydrophobic residues found in its core, causing an increase in the fluorescent signal. This increase in signal is monitored over a range of temperatures and is used to determine the Tm value.

To assess immunogenicity, in vitro and in vivo models have been generated. Since MHC molecules play an important role in T cell dependent immune responses, in vitro assays can be used to test the ability of a peptide to bind MHC (Salvat, et al. (2014) *J. Vis. Exp.* 85). In addition, several animal models such as rats, mice, and non-human primates are currently used in the pre-clinical evaluation of protein therapeutics, wherein the closer a model is to humans, the more accurate it will be at predicting unwanted antibody production in patients (Brinks, et al. (2013) *Pharma. Res.* 30:1719-1728).

In some embodiments, the present invention provides a pharmaceutical composition containing a lysostaphin variant of the present invention. For example, in some embodiments, the present invention provides a composition containing a lysostaphin variant and a pharmaceutically acceptable carrier. In certain embodiments, the present invention provides a lysostaphin variant (e.g., deimmunized lysostaphin) of use in a pharmaceutical composition for treatment or prevention of staphylococcal infection (e.g., of the skin, of a wound, or of an organ) or as a therapy for various active *S. aureus* infections. In preferred embodiments, a pharmaceutical composition of the present invention includes a therapeutically effective amount of a lysostaphin of the invention, together with a pharmaceutically acceptable carrier. The present invention is not limited by the types of pharmaceutically acceptable carrier utilized. Indeed, a variety of carriers are well known in the art including, but not limited to, sterile liquids, such as water, oils, including petroleum oil, animal oil, vegetable oil, peanut oil, soybean oil, mineral oil, sesame oil, and the like. Saline solutions, aqueous dextrose, and glycerol solutions can also be employed as liquid carriers, particularly for solution preparations for injection. Suitable pharmaceutical carriers are described in Remington's Pharmaceutical Sciences, 18th Edition.

A therapeutically effective amount is an amount of lysostaphin variant reasonably believed to provide some measure of relief, assistance, prophylaxis, or preventative effect in the treatment of infection. A therapeutically effective amount may be an amount believed to be sufficient to block a bacterial colonization or infection. Similarly, a therapeutically effective amount may be an amount believed to be sufficient to alleviate (e.g., eradicate) an existing bacterial infection. A pharmaceutical composition of the present invention may be particularly useful in preventing, ameliorating and/or treating bacterial infection.

The compositions of the invention may be administered locally (e.g., topically) or systemically (e.g., intravenously). Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

In accordance with this invention, the terms "treatment", "treating" and the like are used herein to generally mean obtaining a desired pharmacological and/or physiological effect. The effect may be prophylactic in terms of completely or partially preventing an infection and/or may be therapeutic in terms of completely or partially treating (e.g., eradicating) a bacterial infection. The term "treatment" as used herein includes preventing bacterial infection from occurring in a subject (e.g., that may be predisposed to infection (e.g., nosocomial infection) but has not yet been diagnosed as having infection); inhibiting bacterial infection; and/or (c) relieving infection (e.g., completely or partially reducing the presence of bacteria responsible for infection).

Staphylococcal infections, such as those caused by *S. aureus*, are a significant cause of morbidity and mortality, particularly in settings such as hospitals, schools, and infirmaries. Patients particularly at risk include infants, the elderly, the immunocompromised, the immunosuppressed, and those with chronic conditions requiring frequent hospital stays. Patients also at risk of acquiring staphylococcal infections include those undergoing inpatient or outpatient surgery, those within an Intensive Case Unit (ICU), on continuous hemodialysis, with HIV infection, with AIDS, burn victims, people with diminished immunity (e.g., resulting from drug treatment or disease), the chronically ill or debilitated patients, geriatric subjects, infants with immature immune systems, and people with intravascular (e.g., implanted) devices. Thus, in some embodiments, a composition containing a lysostaphin variant is administered to any one of these types of subject as well as to other subjects that have or are susceptible to bacterial infection (e.g., caused by *S. aureus* or *S. epidermidis*).

In some embodiments, a lysostaphin variant of the present invention is formulated as either an aqueous solution, semi-solid formulation, or dry preparation (e.g., lyophilized, crystalline or amorphous, with or without additional solutes for osmotic balance) for reconstitution. Formulations may be in, or reconstituted in, for example, a non-toxic, stable, pharmaceutically acceptable, aqueous carrier medium, at a pH of about 3 to 8, typically 5 to 8, for administration by conventional protocols and regimes or in a semi-solid formulation such as a cream. Delivery can be via, for example, ophthalmic administration, intravenous (iv), intramuscular, subcutaneous or intraperitoneal routes or intrathecally or by inhalation or used to coat medical devices, catheters and implantable devices, or by direct installation into an infected site so as to permit blood and tissue levels in excess of the minimum inhibitory concentration (MIC) of the active agent to be attained (e.g., to effect a reduction in microbial titers in order to cure, alleviate or prevent an infection). In some embodiments, the antimicrobial agent is formulated as a semi-solid formulation, such as a cream (e.g., that is used in a topical or intranasal formulation).

Furthermore, the lysostaphin variant can be co-administered, simultaneously or alternating, with other antimicrobial agents so as to more effectively treat an infectious disease. Formulations may be in, or be reconstituted in, semi-solid formulations for topical, ophthalmic, or intranasal application, liquids suitable for ophthalmic administration, bolus iv or peripheral injection or by addition to a larger volume iv drip solution, or may be in, or reconstituted in, a larger volume to be administered by slow iv infusion. For example, a lysostaphin variant can be administered in conjunction with antibiotics that interfere with or inhibit cell wall synthesis, such as penicillins, nafcillin, and other alpha- or beta-lactam antibiotics, cephalosporins such as cephalothin, aminoglycosides, sulfonamides, antifolates, macrolides, quinolones, glycopepetides such as vancomycin and polypeptides. In some embodiments, a lysostaphin variant is administered in conjunction with one or more antibiotics that inhibit protein synthesis (e.g., aminoglycosides such as streptomycin, tetracyclines, and streptogramins). The present invention is not limited by the type of agent co-administered with deimmunized lysostaphin. Indeed, a variety of agents may be co-administered including, but not limited to, those agents described in U.S. Pat. Nos. 6,028, 051, 6,569,830, and 7,078,377, each of which is hereby incorporated by reference in its entirety. In some embodiments, a lysostaphin variant is administered with monoclonal antibodies; other non-conjugated antibacterial enzymes such as lysostaphin, lysozyme, mutanolysin, and cellozyl muramidase; peptides (e.g., defensins); and lantibiotics (e.g., nisin); or any other lanthione-containing molecules (e.g., subtilin).

Agents co-administered with a lysostaphin variant may be formulated together with the lysostaphin variant as a fixed combination or may be used extemporaneously in whatever formulations are available and practical and by whatever routes of administration are known to provide adequate levels of these agents at the sites of infection.

In preferred embodiments, lysostaphin variants according to the present invention possess at least a portion of the antimicrobial activity of the corresponding non-deimmunized antimicrobial agent. A lysostaphin variant of the present invention may be administered in increased dosages and/or at less frequent intervals due to the decreased immunogenicity. In some embodiments, a lysostaphin variant retains at least 10% of the activity of the non-deimmunized antimicrobial agent. In some embodiments, a lysostaphin variant retains at least 20% of the activity of the non-deimmunized antimicrobial agent. In some embodiments, a lysostaphin variant retains at least 30% of the activity of the non-deimmunized antimicrobial agent. In some embodiments, a lysostaphin variant retains at least 40% of the activity of the non-deimmunized antimicrobial agent. In some embodiments, a lysostaphin variant retains at least 50% of the activity of the non-deimmunized antimicrobial agent. In some embodiments, a lysostaphin variant retains at least 60% of the activity of the non-deimmunized antimicrobial agent. In some embodiments, a lysostaphin variant retains at least 70% of the activity of the non-deimmunized antimicrobial agent. In some embodiments, a lysostaphin variant retains at least 80% of the activity of the non-deimmunized antimicrobial agent. In some embodiments, a lysostaphin variant retains at least 90% of the activity of the non-deimmunized antimicrobial agent. In some embodiments, a lysostaphin variant retains 90% or more (e.g., 95%, 97%, 99% or more) of the activity of the non-deimmunized antimicrobial agent.

Suitable dosages and regimes of a deimmunized lysostaphin may vary with the severity of the infection and the sensitivity of the infecting organism and, in the case of combination therapy, may depend on the particular agent (e.g., anti-staphylococcal agent) co-administered. Dosages may range from about 0.05 to about 500 mg/kg/day (e.g., in some embodiments, range from 0.1-10 mg/kg/day, in some embodiments, range from 10-100 mg/kg/day, in some embodiments, range from 100-200 mg/kg/day, in some embodiments, range from 200-400 mg/kg/day, in some embodiments, range from 400-500 mg/kg/day), although higher (e.g., 500-1000 mg/kg/day) or lower (e.g., 0.1-0.5 mg/kg/day doses may be provided, given as single or divided doses, or given by continuous infusion. In some embodiments, deimmunized lysostaphin is administered once a day, twice a day, three times a day or more frequently (e.g., four or more times a day). In some embodiments, deimmunized lysostaphin is administered once a week, twice a week, or every other day. In some embodiments, deimmunized lysostaphin is administered once every other week, once a month, once every two months, once every three months, once every four months, once every five months, once every six months, once every 9 months, once every year or less frequently.

In certain embodiments, a deimmunized lysostaphin of this invention is aglycosylated. Aglycosylation can be carried out as described here, and can include mutations at residues Ser126 and/or Thr127. Exemplary mutations include, Ser126Pro and Thr127Ala.

In some embodiments, a deimmunized lysostaphin of the present invention may be further modified in order to further decrease immunogenicity of the lysostaphin molecule while retaining antimicrobial activity. For example, in some embodiments, a deimmunized lysostaphin is conjugated to a water soluble polymer. The present invention is not limited by the type of water soluble polymer to which a deimmunized lysostaphin is conjugated. Indeed, a variety of water soluble polymers may be used including, but not limited to, poly(alkylene oxides), polyoxyethylated polyols and poly(vinyl alcohols). Poly(alkylene oxides) include, but are not limited to, polyethylene glycols (PEGs), poloxamers and poloxamines. The present invention is not limited by the type of conjugation used (e.g., to connect a deimmunized lysostaphin to one or more water-soluble polymers (e.g., PEG)). In some embodiments, a poly(alkylene oxide) is conjugated to a free amino group via an amide linkage (e.g., formed from an active ester such as the N-hydroxysuccinimide ester) of the poly(alkylene oxide). In some embodiments, an ester linkage remains in the conjugate after conjugation. In some embodiments, linkage occurs through a lysine residue present in the deimmunized lysostaphin molecule. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, deimmunized lysostaphin is conjugated to PEG utilizing any of the methods, reagents and/or linkages described in U.S. Pat. Nos. 4,424,311; 5,672,662; 6,515,100; 6,664,331; 6,737, 505; 6,894,025; 6,864,350; 6,864,327; 6,610,281; 6,541, 543; 6,515,100; 6,448,369; 6,437,025; 6,432,397; 6,362, 276; 6,362,254; 6,348,558; 6,214,966; 5,990,237; 5,932, 462; 5,900,461; 5,739,208; 5,446,090 and 6,828,401; and WO 02/02630 and WO 03/031581. In some embodiments, a deimmunized lysostaphin-water soluble polymer conjugate of the present invention is produced by a third party (e.g., NEKTAR, San Carlos, Calif.). In some embodiments, the conjugate includes a cleavable linkage present in the linkage between the polymer and deimmunized lysostaphin (e.g., such that when cleaved, no portion of the polymer or linkage remains on the deimmunized lysostaphin molecule). In some embodiments, the conjugate includes a cleavable linkage present in the polymer itself (e.g., such that when cleaved, a small portion of the polymer or linkage remains on the deimmunized lysostaphin molecule).

In some embodiments, a deimmunized lysostaphin of the present invention is used for the treatment and/or prevention of a biofilm (e.g., as described in US 2003/0215433 and WO 03/082148). In other embodiments, a deimmunized lysostaphin of the present invention is used in the prevention and/or treatment of a microbial infection, including bacterial infections by members of the genus *Staphylococcus*. According to such methods, a subject in need of treatment (e.g., a subject with or at risk of developing an *S. aureus* infection) is administered an effective amount of a deimmunized lysostaphin so that the microbial infection is prevented or treated. Subjects benefiting from this treatment include those exhibiting clinical signs or symptoms of an infection, a subject exposed to a bacterium (e.g., S. aureus), or a subject suspected of being exposed to a bacterium (e.g., S. aureus). Effective treatment will result in a decrease, attenuation, inhibition or amelioration of the well-known signs or symptoms of infection. In some embodiments, treatment includes nasal applications, e.g., as described in US 2003/0211995; or topical applications, e.g., as described in US 2004/0192581.

The selected dosage level will depend upon a variety of factors including the activity of the particular deimmunized lysostaphin employed, the route of administration, the time of administration, the rate of excretion or metabolism of the particular deimmunized lysostaphin, the duration of the treatment, other drugs, compounds and/or materials used in combination with the particular deimmunized lysostaphin employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a deimmunized lysostaphin at levels lower than that required in order to achieve the desired therapeutic effect and gradually increase the dosage until the desired effect is achieved. This is considered to be within the skill of the artisan.

Effective doses can also be determined in an art-recognized model of S. aureus infection. There are many different in vivo model systems that can be used by one of skill in the art to further demonstrate efficacy and aid in identification of doses that will be both safe and effective in humans. Such animal model systems are well-accepted and used during development of new human pharmaceuticals. Examples of such model systems include, but are not limited to, a guinea pig model of S. aureus wound infection (Kernodle & Kaiser (1994) Antimicrob. Agents Chemother. 38:1325-1330); a rabbit model of S. aureus abscess in rabbits (Fernandez, et al. (1999) Antimicrob. Agent Chemother. 43:667-671); a mouse model of S. aureus skin infection (Gisby & Bryant (2000) Antimicrob. Agents Chemother. 44:255-260); a mouse model of deep dermal S. aureus infection (Godin, et al. (2005) J. Antimicrob. Chemother. 55:989-994); and a mouse intraperitoneal infection model (Patel, et al. (2004) Antimicrob. Agents Chemother. 48:4754-4761). In such models, therapeutics can be tested against infections where the infection established is from inoculation of the animal with various strains of S. aureus. Demonstration of efficacy in such models is measured in many ways and would include but not be limited to a reduction in mortality rate, a reduction in bacterial cell counts determined by microscopic examination of tissue or blood samples taken from the animals, or even assessment of wound healing in the animals.

The following non-limiting examples are provided to further illustrate the present invention.

EXAMPLE 1

Deimmunization of Lysostaphin Catalytic Domain

Materials and Methods

Reagents and Media. Primers were ordered with standard desalting from IDT Technologies (Coralville, Iowa). PCR cleanup and gel extraction kits were from Zymo Research (Irvine, Calif.). Commercial lysostaphin was purchased from Sigma (St. Louis, Mo.). Plasmid purification was performed using QIAPREP Spin Miniprep Kit (Qiagen; Valencia, Calif.). All enzymes were obtained from New England BioLabs (Ipswich, Mass.), and all reagents from VWR Scientific (Philadelphia, Pa.), unless otherwise noted. Peptides derived from the lysostaphin catalytic domain were ordered from GenScript (Piscataway, N.J.), and were greater than 85% pure. MHC-II DR molecules were purchased from Benaroya Research Institute (Seattle, Wash.), anti-MHC-IIDR antibody from Biolegend (San Diego, Calif.), and DELFIA Eu-labeled Streptavidin was from PerkinElmer (Boston, Mass.).

Epitope Prediction. The T cell epitope content of the lysostaphin catalytic domain was predicted using EpiMatrix, a scoring matrix whose predictions have been shown to correlate well with the clinically observed immunogenicity of therapeutics. EpiMatrix is a pocket profile method used to predict HLA binding (Groot & Moise (2007) Curr. Opin. Drug Discover. Dev. 10). In this approach, a protein is divided into overlapping 9-mer peptides, each of which is then evaluated for its binding potential to HLA alleles. The eight most common HLA alleles (DRB1*0101, DRB1*0301, DRB1*0401, DRB1*0701, DRB1*0801, DRB1*1101, DRB1*1301, DRB1*1501), which are representative of more than 90% of the human population (Southwood, et al. (1998) J. Immunol. 160:3363-3373), were considered. Based on binding potential, each peptide was assigned a corresponding standardized Z score and then mapped onto the cluster immunogenicity scale, which represents the deviation in epitope content from what would be expected for a randomly generated peptide (Groot, et al. (2013) Exp. Rev. Clin. Pharmacol. 6:651-662). Peptides scoring above 1.64 on the EpiMatrix "Z" scale (approximately the top 5%) were considered to be likely to bind to the corresponding MHC molecule, while peptides scoring in the top 1% (above 2.32 on the scale) were extremely likely to bind (Koren, et al. (2007) Clin. Immunol. 124:26-32). If a peptide had a score higher than 1.64 for four or more alleles, it was said to contain an EpiBar (Weber, et al. (2009) Adv. Drug Deliv. Rev. 61:965-976).

Homology Modeling of Lysostaphin. EpiSweep analyzes deimmunized variants based on two quantified measures: epitope score and force field energy value. However, the algorithm uses the structure of the protein to calculate energy. Since the crystal structure of lysostaphin was not known, a lysostaphin model was constructed based on the available crystal structures of proteins similar to the catalytic domain of lysostaphin. The templates were selected by comparing the sequence of lysostaphin to the PDB database and selecting three highly similar protein structures (PDB accession code: 2B0PA, 2B44A, and 1QWYA). For homology modeling purposes, sequence identity above 30% is considered sufficiently accurate (Rost (1999) Prot. Eng. Design Select. 12:85-94). All of the template structures belong to LytM, an autolysin from S. aureus, which has 48% sequence identity and 63% similarity to the catalytic domain of lysostaphin (Lu, et al. (2013) supra).

The catalytic domain models were built using LytM crystal structures by employing MODELLER, a homology modeling protocol that builds a three-dimensional structure of proteins based on coordinates of template structures (Shen & Sali (2006) Protein Sci. 15:2507-2524). Two hundred-fifty models were generated and the most accurate one was selected in terms of the DOPE statistical potential (Shen & Sali (2006) supra).

For regions of the protein for which there was no sufficient coordinate information to allow complete and accurate construction of the model, a protein loop modeling method, FREAD, was used to remodel the existing gaps (Choi & Deane (2010) *Proteins* 78:1431-1440). The obtained homology model was minimized against AMBER99sb with an implicit solvent model (GB/SA). The aglycosylated wild-type (125 NPT) was modeled by applying in silico mutations to the original model using Scwrl4 (Krivov, et al. (2009) *Proteins: Struct. Funct. Bioinform.* 77:778-795), followed by energy re-minimization.

Evolutionary Information. The process of deimmunization requires mutation of residues that are predicted to contribute to MHC binding. However, T cell epitopes can be present in any part of the protein. Thus, random selection of mutations could lead to disruption of proper folding and function. This problem can be mitigated by adopting point mutations found in sequences remotely similar to the target sequence. To determine which mutations could be used in the deimmunization process, a total of 10,000 homologs to $LST^{CAT}$ were collected by running PSI-BLAST (3 iterations, e-value <0.001). These sequences were filtered to remove those with >50% gaps or <35% sequence identity to the wild-type. A diverse set of 218 representative sequences was subselected so as to have at most 90% sequence identity to each other. Allowed mutations were those predicted to delete at least one putative epitope while appearing as frequently as expected in terms of a background probability distribution (McCaldon & Argos (1988) *Proteins* 4:99-122). Additional filters excluded mutations to/from Pro and Cys, mutations involving active site residues (32His, 36Asp, 82His, 113His and 115His), and mutations previously found to be detrimental (Thr43Asp, Ser50Asp, Asn121Asp, and Leu135Ser).

EpiSweep. Structure-based EpiSweep is a protein redesign tool that allows for protein deimmunization while retaining protein stability and functionality. The algorithm combines validated immunoinformatics and structural modeling to produce Pareto optimal designs that can then be selected experimentally for the best immunogenicity, stability, and activity scores. The method by which EpiSweep selects the optimal designs has been described (Parker, et al. (2013) *J. Computation. Biol.* 20:152-165). Briefly, the algorithm addresses the stability concern by assuming the protein backbone as rigid and selecting the best side-chain conformations from a discrete set of rotamers, which are chosen to minimize total protein energy. All rotamers and rotamer pairs are evaluated for potential clashes with the backbone and with each other. For example, conformations found to contain rotamers with a significant van der Waals radii overlap or with exceptionally high intra- or inter-rotamer energies are discarded (Parker, et al. (2013) supra).

For EpiSweep analysis of the lysostaphin catalytic domain, the mutational load was allowed to vary from two to eight mutations and the algorithm was constrained to disallow mutations at the active site (His32, Asp36, His82, His113, and His115). Furthermore, the algorithm was to generate not only Pareto optimal plans at each mutational load (designs with the lowest possible rotamer energies), but also the additional 19 suboptimal plans (designs that have successively worse rotamer energies as compared to the Pareto optimal plans). This analysis was performed to correct for any possible mistakes that may arise due to the rigid backbone assumption, since proteins are characterized by a high degree of flexibility. In fact, it has been observed that further side chain optimization changes Pareto optimality of EpiSweep designs, and thus may affect design selection (Parker, et al. (2013) supra).

EpiSweep Analysis of Ser126Pro Backbone. For analysis using the Ser126Pro lysostaphin backbone, the algorithm considered only the 12 well-tolerated mutations (Ser124Gly, Ser122Asp, Asn121Gly, Arg118Thr, Ile99Gln, Lys95Glu, Tyr93His, Leu83Met, Lys46His, Ile41Glu, Asn13His, and Asn12Gly). Since Ser122Asp mutation was an extremely efficient epitope remover (Table 6), the algorithm was also constrained to include this mutation in all generated plans. Additional post-processing energy minimization of the EpiSweep designs was performed using molecular modeling software TINKER against AMBER (AMBER99sb) force field and an implicit solvent model (GB/SA).

Plasmids and Strains. *P. pastoris* strain GS115 and expression vector pPIC9 were obtained from Invitrogen (Grand Island, N.Y.). *S. aureus* strain SA113 and *S. aureus* subsp. *aureus* (ATCC 25923) were obtained from the American Type Culture Collection (Manassas, Va.). Other strains of *S. aureus* (methicillin sensitive strains 6445 and 3425-1, and MRSA strain 3425-3) were clinical isolates.

Synthesis of Lysostaphin Gene Optimized for *P. pastoris* Expression. Synthesis of a synthetic lysostaphin gene was performed as described (Zhao, et al. (2014) *Appl. Environ. Microbiol.* 80:2746-53). The majority of the codons was replaced to reflect the codon preference by *P. pastoris* (Zhao, et al. (2000) *Sheng Wu Gong Cheng Xue Bao* 16:308-11). To disrupt long A+T nucleotide stretches in the gene sequence, second-most frequent codons were introduced as needed.

PCR-Based Synthesis of Single Point Mutants. Lysostaphin single point mutants were synthesized as described (Zhao, et al. (2014) supra). Briefly, the mutations were introduced using splice overlap extension PCR with primers listed in Table 1. For instance, the Ser122Gly mutation was introduced by first amplifying lysostaphin gene using Syn_F and S122G_R, and S122G_F and Syn_R primers. The resulting (gel-purified) gene fragments were then mixed at an equimolar ratio, and used as a template in a subsequent reaction using Syn_F and Syn_R primers. The final product was the full-length lysostaphin gene with the Ser122Gly mutation. All PCR reactions were performed using PHUSION High-Fidelity DNA polymerase. The lysostaphin gene harboring the desired mutation was then digested with EcoRI and XhoI, and ligated into the pPIC9 plasmid using T4 DNA ligase. The end product of ligation was the lysostaphin gene fused to the alpha mating factor secretion signal from *Saccharomyces cerevisiae*. The resulting plasmid was transformed into *E. coli* DH5α electrocompetent cells (F⁻□80lacZΔM15Δ (lacZYA-argF) U169 recA1 endA1 hsdR17 ($r^-_K$ $m^+_K$) phoA supE44 λ⁻thi1 gyrA96 recAl). Clones were evaluated for the presence of lysostaphin gene using Syn_F and Syn_R primers and sequenced to confirm the presence of mutations (primers AOX1_F and AOX1_R).

TABLE 1

| Primer | Sequence (5'->3') | SEQ ID NO: |
|---|---|---|
| N12G_R | ACCCTTCTTGTAGTTACCCAACCATTGAGCGGA | 50 |
| N12G_F | TCCGCTCAATGGTTGGGTAACTACAAGAAGGGT | 51 |
| N13H_R | CGATGAATTCTTACTTGATGGTACCCCA | 52 |
| N13H_F | ATCGCTCGAGAAAAGAGCTGCTACCCA CGAGCACTCCGCTCAATGGTTGAACCACTAC | 53 |
| F38GR | GGTACCGATGTTCATACCGAAGTCAACACCGTA | 54 |
| F38G_F | TACGGTGTTGACTTCGGTATGAACATCGGTACC | 55 |

TABLE 1-continued

| Primer | Sequence (5'->3') | SEQ ID NO: |
|---|---|---|
| I41E_R | AGCCTTGACTGGGGTACCCTCGTTCATGAAGAA | 56 |
| I41E_F | TTCTTCATGAACGAGGGTACCCCAGTCAAGGCT | 57 |
| K46H_R | ACCGGAGGAGATAGCGTGGACTGGGGTACCGAT | 58 |
| K46H_F | ATCGGTACCCCAGTCCACGCTATCTCCTCCGGT | 59 |
| L83M_R | TACTTGGACATGTGCATGTACCATTG | 60 |
| L83M_F | CAATGGTACATGCACATGTCCAAGTA | 61 |
| Y93H_R | TTGACCAGCCTTGACGTGGTCACCGACCTTGAC | 62 |
| K95E_R | GATGATTTGACCAGCCTCGACGTAGTCACCGAC | 63 |
| K95E_F | GTCGGTGACTACGTCGAGGCTGGTCAAATCATC | 64 |
| Y93H_F | GTCAAGGTCGGTGACCACGTCAAGGCTGGTCAA | 65 |
| I99Q_R | ACCGGACCAACCGATTTGTTGACCAGCCTTGAC | 66 |
| I99Q_F | GTCAAGGCTGGTCAACAAATCGGTTGGTCCGGT | 67 |
| R118T_R | GAAGGAGTTGACCATGGTTTGGAAGTGCAAGTG | 68 |
| R118T_F | CACTTGCACTTCCAAACCATGGTCAACTCCTTC | 69 |
| N121G_R | TGGGTTGGAGAAGGAACCGACCATTCTTTGGAA | 70 |
| N121G_F | TTCCAAAGAATGGTCGGTTCCTTCTCCAACCCA | 71 |
| S122D_R | GGTTGGGTTGGAGAAGTCGTTGACCATTCTTTG | 72 |
| S122D_F | CAAAGAATGGTCAACGACTTCTCCAACCCAACC | 73 |
| S122G_R | GGTTGGGTTGGAGAAACCGTTGACCATTCTTTG | 74 |
| S122G_F | CAAAGAATGGTCAACGGTTTCTCCAACCCAACC | 75 |
| S124G_R | TTGAGCGGTTGGGTTACCGAAGGAGTTGACCAT | 76 |
| S124G_F | ATGGTCAACTCCTTCGGTAACCCAACCGCTCAA | 77 |
| S124Y_R | TTGAGCGGTTGGGTTGTAGAAGGAGTTGACCAT | 78 |
| S124Y_F | ATGGTCAACTCCTTCTACAACCCAACCGCTCAA | 79 |
| Syn_R | CGATGAATTCTTACTTGATGGTACCCCA | 80 |
| Syn_F | ATCGCTCGAGAAAAGAGCTGCTACCCAC | 81 |
| AOX1_R | GCAAATGGCATTCTGACATCC | 82 |
| AOX1_F | GACTGGTTCCAATTGACAAGC | 83 |
| AflII_R | AACGTAACCAGCGGACTTAAGGAATGGCATTGGGTC | 84 |
| AflII_F | GACCCAATGCCATTCCTTAAGTCCGCTGGTTACGGT | 85 |
| T118R_R | GAAGTCGTTGACCATTCTTTGGAAGTGCAAGTG | 86 |
| T118R_F | CACTTGCACTTCCAAAGAATGGTCAACGACTTC | 87 |

Cloning of LST Integrated Designs. Lysostaphin variants that were not expressing in the first round of screening and contained the Arg118Thr mutation were synthesized without that mutation and re-examined for expression. Splice overlap extension PCR was used to revert the Arg118Thr mutation back to wild-type (Thr118) with primers T118R_F and T118R_R (Table 1).

To prepare the pPIC9 plasmid for insertion of synthesized genes, a silent mutation was introduced into the lysostaphin linker (residues 135-136) to accommodate a cutting site for the restriction enzyme AflII. To introduce the necessary mutations, splice overlap extension PCR was used with primers AflII_F and AflII_R (Table 1). The synthetic genes were digested with XhoI and AflII restriction enzymes, and ligated in similarly digested pPIC9 plasmid using T4 DNA ligase. The resulting plasmid was transformed into E. coli DH5α electrocompetent cells and the resulting clones were sequenced to confirm the presence of mutations.

P. pastoris Expression and Purification. After DH5α clones were confirmed for the presence of correct catalytic domain mutation by sequence analysis, the purified plasmid was digested with SacI High-Fidelity restriction enzyme prior to electroporation into P. pastoris strain GS115. The resulting transformants were grown on MD plates (1.34% yeast nitrogen base, 0.000004% biotin, 2% dextrose and 1% agar). For expression studies, clones were grown in BMGY media (1% yeast extract, 2% peptone, 1.34% yeast nitrogen base, 0.000004% biotin, 1% glycerol, 100 mM phosphate buffer, pH 6) at 30° C. in 500 ml shake flasks covered with four layers of cheese cloth for enhanced oxygen flow to the yeast. After 24 hours, cells were centrifuged at 3,000 rpm in a table top centrifuge for 10 minutes. The cells were then resuspended in 100 ml of BMMY induction media (1% yeast extract, 2% peptone, 1.34% yeast nitrogen base, 0.000004% biotin, 0.5% methanol, 100 mM phosphate buffer, pH 6) and allowed to grow for the next 48 hours at 30° C. At 12-hour intervals, 100% methanol was added for a final concentration of 1%. After 48 hours of induction, shake flask culture was centrifuged in a table top centrifuge at 3,000 rpm for 15 minutes. The resulting supernatant was filtered to remove any yeast cells and diluted 1:5 with 10 mM $KH_2PO_4$ buffer at pH 7.5. Diluted supernatant was flowed over a gravity column packed with 500 µl SP-SEPHAROSE Fast Flow resin (GE Healthcare; Cleveland, Ohio). The column was washed with 5 ml of 50 mM NaCl in 10 mM $KH_2PO_4$ at pH 7.5. Protein was eluted with 500 µl aliquots of 200 mM NaCl in mM $KH_2PO_4$, pH 7.5. The purity of lysostaphin was determined using SDS-PAGE. The protein concentration was quantified using ND-1000 Spectrophotometer (Nano-Drop Technologies; Wilmington, Del.). To ensure accuracy, protein absorbance measure was adjusted using the absorbance adjustment factor of 0.4 for both wild-type lysostaphin and its variants. Briefly, the adjustment factor was calculated as the inverse of the reported Abs 0.1% (=1 g/L) value (ProtParam, ExPASy).

Lytic Assay of Culture Supernatant. S. aureus cells were grown either to mid-log or to saturation in tryptic soy broth (TSB) at 37° C. with shaking. The cells were harvested by centrifugation and washed once in phosphate buffered saline (PBS: 2.7 mM KCl, 1.5 mM $KH_2PO_4$, 8.9 mM $Na_2HPO_4$, 136.9 mM NaCl, pH 7.4). The assay was performed in 96-well, black, clear bottom plates from Greiner Bio-One (Monroe, N.C.). The final (250 µl) reaction was composed of 10 µl of P. pastoris culture supernatant, S. aureus cells at OD600=1.5, and 5 µM SYTOX Green (Thermo Fisher Scientific; Waltham, Mass.), all in PBS. Data were collected using SPECTRAMAX GEMINI Fluorescence Microplate Reader (Molecular Devices; Sunnyvale, Calif.) using an excitation/emission of 504/523 nm, and rates were determined from the slope of the steepest linear portion of the trace. Each assay was performed with 500 ng of commercially-sourced lysostaphin (ssLys) as an internal control.

The amount of protein used in each assay was estimated from SDS-PAGE gels. Briefly, 10 µl of culture supernatant was run on a SDS-PAGE gel together with standards of 0.5 µg, 0.7 µg, and 1 µg of ssLys in separate lanes. The gel was stained using GELCODE Blue Stain Reagent from Thermo Fisher Scientific (Carlsbad, Calif.) and bands quantified using Quantity Tools from Image Lab 5.1 software (Bio-Rad Laboratories; Hercules, Calif.).

Lytic Assay Using Purified Protein. The activity of purified lysostaphin variants was examined using the SYTOX® kinetic assay as previously described in Chapter 2, Section 3.2.6. 200 ng of purified enzyme (instead of culture supernatant) was used in each reaction.

MIC Assay. The MICs of wild-type lysostaphin and its variants were determined by adding 2-fold serial dilutions of enzymes into wells of a polypropylene 96-well plate (Costar 3879) containing ~40,000 S. aureus SA113 (or S. aureus 6445, 3425-1, 3425-3) cells in Muller Hinton broth (BD) supplemented with 2% NaCl and 0.1% bovine serum albumin, yielding a total volume of 100 µl. Plates were grown overnight at 37° C. with shaking at 900 rpm on an Orbit P4 orbital shaker (Labnet; Edison, N.J.). The inhibitory activity of purified lysostaphin was determined by the concentration of enzyme that completely inhibited bacterial growth. The assay was performed in triplicate for each enzyme.

PNGase F Treatment. P. pastoris culture supernatant was treated with 1 µl of 10× G7 buffer and the same volume of REMOVE-IT PNGase F. The reaction was incubated for 1 hour at 37° C. and the results analyzed by SDS-PAGE.

Saturation Mutagenesis. Saturation mutagenesis at position 125 of the lysostaphin catalytic domain was carried out using known methods (Zhao, et al. (2014) supra). Briefly, saturation mutagenesis was performed by splice overlap extension PCR using the lysostaphin synthetic gene as a template and degenerate NNK primers. The resulting 32-member library was transformed into P. pastoris, and transformants were grown on YPD medium (1% yeast extract, 2% peptone, 1% methanol, 1% agar) at 30° C. for 48 hours. To find yeast clones expressing the active enzymes, molten top agar (0.5% yeast extract, 1% peptone, 1% NaCl, 0.75% agar) containing S. aureus SA113 cells was poured over YPM yeast plates and incubated at 37° C. for 10 hours. Halo-forming colonies were picked out and amplified using primers Syn_F and Syn_R, and the genes were sequenced using primers AOX1_F and AOX1_R.

MIC Assay Using P. pastoris Culture Supernatant. Lysostaphin MIC was determined essentially as described (Zhao, et al. (2014) supra). Briefly, 100 µl aliquots of P. pastoris culture supernatant were serially diluted in TSB. Each well was inoculated with 100 µl of ~$10^6$ CFU/ml S. aureus SA113 in TSB. Microplates were incubated at 37° C. for 24 hours. The inhibitory activity in culture supernatants was assessed as the $MIC_{50}$, the treatment dilution yielding 50% inhibition of growth. $MIC_{50}$ was quantified by measuring light scattering at 650 nm in a microplate reader.

Thermostability. The relative thermostability of the lysostaphin variants was determined by differential scanning fluorimetry, as previously described (Niesen, et al. (2007) Nat. Protocols 2:2212-2221). Proteins and SYPRO Orange were diluted in PBS (final concentrations of 100 µg/ml and 5× in 20 µl reaction volume, respectively), and fluorescence was quantified at 1-degree increments from 25 to 94° C. using an Applied Biosystems ABI 7500 fast real-time PCR system. The reactions were performed using PCR Plates for Fast Thermocyclers (VWR; Radnor, Pa.). Fluorescence was quantified using the preset TAMRA parameters. Melting temperatures were determined by data analysis with the 'DSF Analysis v3.0.xlsx' EXCEL sheet and GraphPad Prism v.6.02 software.

MHC Binding Assays. MHC II competition binding assays were performed using a 384-well high throughput assay as previously described (Salvat, et al. (2014) supra). Binding assays were performed for the eight alleles: DRB1*0101, 0301, 0401, 0701, 0801, 1101, 1301, and 1501. Briefly, 100 nM biotinylated control peptides composed of known peptide antigens for each MHC II allele were incubated in polypropylene 384-well plates with 50 nM purified recombinant MHC II protein and serial dilutions of LST or variant peptide fragments (100 µM to 10 nM). Peptide-MHC II complexes were captured from equilibrated solutions using the conformation specific anti-HLA-DR antibody L243 coated on high binding ELISA plates. Bound control peptide was quantified using the DELFIA streptavidin-Europium conjugate and time resolved fluorescence (SpectraMax Gemini Fluorescence Microplate Reader).

Biofilm Degradation Assay. S. aureus SA113 was grown overnight in TSB at 37° C. shaking. The cells were then diluted 1:100 in TSB supplemented with 5% ethanol and 0.1% glucose and 100 µl of cell suspension was added to wells of a 96-well plate (Costar 3595). The cells were left to form biofilms overnight at 37° C. without shaking. The resulting biofilms were then washed three times in water and treated with 200 ng of enzyme in 100 µl for 75 minutes. No-treatment wells contained PBS with 0.1% BSA. The plates were washed three times in water after the treatment and stained with 0.1% crystal violet for 15 minutes. The plates were then washed again three times in water and allowed to dry. Two hundred µl of 30% acetic acid was added to each well and allowed to dissolve the crystal violet stain for minutes at 25° C. with shaking. Destain (150 µl) was transferred to a new 96-well plate and the absorbance of each well was measured in a SPECTRAMAX 190 spectrophotometer (Molecular Devices; Sunnyvale, Calif.) at 550 nm.

Murine Lung Infection Model. Overnight LB cultures of S. aureus strain ATCC 25923 were pelleted, washed twice with PBS, and resuspended to give $10^8$-$10^9$ colony forming units (CFU) in 40 µl of PBS. The actual inoculum was determined by serial dilution of the input bacterial suspension on LB agar (DIFCO), followed by incubation at 37° C. for 24 hours. Adult female C57BL/6J mice (age, 8 to 12 weeks; Jackson Laboratories, Detroit, Mich.) were anesthetized briefly with isoflurane and inoculated with 40 µl of bacterial suspension via oropharyngeal aspiration. At 1 hour post-infection, a second 40 µl PBS inoculation containing either 2.5 µg wild-type LST, 2.5 µg variant Flex 5, 2.5 µg variant Flex 9, or a blank control. At 24 hours post-infection, mice were sacrificed and lungs were excised, placed into 1 ml of cold PBS, and homogenized. Viable bacterial counts in the lung homogenate were determined by plating serial dilutions onto LB agar, followed by incubation at 37° C. for 24 hours.

HUMI Murine Immunogenicity Studies. HUMI mice were constructed by surgical transplantation of human bone marrow, liver, and thymus tissues into NOD/SCID/$Y_c^{-/-}$ mice (Dartmouth Transgenics & Genetic Constructs Shared Resource) as described (Brainard, et al. (2009) J. Virol. 83:7305-21). All animals were humanized from the same human donor. Mice used experimentally had human lymphocytes as a minimum of 25% of their total peripheral blood leukocytes. Fourteen weeks post-engraftment, 12 female HUMI mice were divided into 3 groups of 4 each and immunized with a single 50 µl subcutaneous injection of 100 µg wild-type LST, 100 µg variant Flex 5, or 100 µg variant Flex 9 in complete Freund's adjuvant (CFA). Two weeks following the immunization, mice were sacrificed and splenocytes were harvested and pooled for each group. Pooled splenocytes ($5×10^5$/well) were plated in triplicate into 96-well plates with medium containing 5% fetal calf serum, 1-glutamine, antibiotics, and a final concentration of 10 µg/ml LST or variants (or 1% DMSO as a control). After 72 hours of incubation, wells were pulsed with 1 µCi of

[³H]thymidine (Dupont NEN, Boston, Mass.) and harvested 6 hours later onto UNIFILTER 96-well GF/C plates for assessment of thymidine incorporation by scintillation counting (Packard MicroSant NXT counter).

Transgenic DR4 Murine Immunogenicity Studies. Twelve female 6-8 week old DR4 transgenic mice (Abb Knockout/Transgenic HLA-DR4; B6.129S2-H2-Ab1tm1GruTg(HLA-DRA/H2-Ea, HLA-DRB1*0401/H2-Eb)1Kito; Taconic Farms, Germantown, N.Y.) were divided into four groups of three each and immunized with 50 µl subcutaneous injections of wild-type LST using one of the following four schemes: (i) initial immunization with 100 µg enzyme in CFA, followed by 100 µg boosts in incomplete Freund's adjuvant (IFA) on days 14 and 28; (ii) initial immunization with 20 µg enzyme in CFA, followed by 20 µg boosts in IFA on days 14 and 28; (iii) initial immunization with 100 µg enzyme in PBS buffer, followed by 100 µg boosts in PBS buffer on days 7, 14, 21 and 28; (iv) initial immunization with 20 µg enzyme in PBS buffer, followed by 20 µg boosts in PBS buffer on days 7, 14, 21 and 28. Serum IgG antibody titers against wild-type LST were measured on days 13, 20, 27, 34, and 62. Five weeks after the final boost, all 12 mice exhibited equivalent maximum ELISA signals at a 1:40 serum dilution and all signals were within 20% at a 1:160 dilution. Mice were housed without further manipulation until week 23 of the study, at which time serum IgG antibody titers were again measured and mice were divided into two experimental arms having equivalent average antibody titers. Note that during the week 9 to week 23 recovery period, two mice (the lowest titer 100 µg no adjuvant and one of the high titer 100 µg adjuvant) began suffering hair loss, weight loss, and reduced mobility and were sacrificed as per the IACUC approved protocol. At week 24, one arm was rechallenged with 100 µg wild-type LST in IFA and the other arm with 100 µg variant Flex 5 in IFC. At week 26, mice were sacrificed and splenocytes were harvested and pooled for each group. Proliferation assays were conducted as described above.

Bioinformatics Analysis. Sequence alignment of lysostaphin and its homologous sequences ALE-1 and LytM was performed using ClustalW.

Epitope Prediction

EpiMatrix analysis of the lysostaphin catalytic domain of an Asn125Gln mutant (Zhao, et al. (2014) supra) showed that the domain had many predicted T cell epitopes, with a total epitope score of 46. The protein had 14 instances of predicted top 1% binders (score>2.32), and 32 instances of top 5% binders (score>1.64). The sequence was also found to contain three EpiBars (peptides which have a score of 1.64 or higher for a minimum of four alleles), with the peptide [116]FQRMVNSFS[124] (SEQ ID NO:88) predicted as highly immunogenic for all eight alleles (Table 2).

TABLE 2

| Peptide | SEQ ID NO: | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|---|
| WLNNYKKGY | 89 | | | | | 1.69 | 2.12 | 1.73 | 1.93 |
| LNNYKKGYG | 90 | | | | | 2.46 | | | 1.9 |
| INGGMHYGV | 91 | | | | | | | | 1.93 |
| VDFFMNIGT | 92 | | | | | | | | |
| FFMNIGTPV | 93 | 2.41 | | 1.79 | 1.93 | | | | |
| FMNIGTPVK | 94 | | | 2.19 | | | 2.06 | | |
| MNIGTPVKA | 95 | | 1.68 | | | | | | |
| IGTPVKAIS | 96 | | | | | | | 1.85 | |
| VKAISSGKI | 97 | 2.35 | 2.02 | 1.65 | 2.9 | | | | 2.75 |
| IENDGVHRQ | 98 | | | 2.06 | | | | | |
| VHRQWYMHL | 99 | | | | | | | | 1.99 |
| WYMHLSKYN | 100 | | | | 2.72 | | | | |
| YMHLSKYNV | 101 | 1.86 | | | | 2.29 | 2.72 | | 2.01 |
| LSKYNVKVG | 102 | | | | | | 1.67 | | |
| YVKAGQIIG | 103 | 1.66 | | | | | 1.97 | | |
| IIGWSGSTG | 104 | | | | 1.76 | | | | |
| WSGSTGYST | 105 | 1.95 | | | | 1.92 | | | |
| LHFQRMVNS | 106 | | | | | | | 2.05 | |
| FQRMVNSFS | 88 | 3.4 | 2.54 | 3.41 | 2.27 | 2.66 | 3.37 | 2.24 | 2.86 |
| QRMVNSFSQ | 107 | | | | 1.71 | | 1.8 | | |
| MVNSFSQST | 108 | 1.91 | | | 2.41 | | | | 2.12 |

Selection of the Most Frequent Mutations for a Preliminary Design Analysis

EpiSweep yielded a total of 1,533 plans, 81 of which were evaluated as Pareto optimal plans at mutational loads of two to eight mutations. At this point, it was possible to simply select a set of designs, which would then be subjected to experimental analysis for proper folding and activity. However, previous efforts to produce deimmunized lysostaphin based on sequence-based EpiSweep did not yield active variants. Structure-based EpiSweep was designed as an alternative method, which was supposed to produce better results. Given that inaccurate lysostaphin representation may have resulted in errors, an iterative feedback strategy was used, wherein the 15 most frequent mutations (individually) were tested for their impact on protein folding (expression) and activity.

The results (Table 3) showed that the most frequent 15 mutations were present in 9-67% of total plans, and in 1-65% of Pareto optimal plans. The mutations were all found on the surface of the catalytic domain. Buried residues were not frequently used by EpiSweep. Indeed, buried residues Ser49Gly and Ser49Ala take positions as the 18$^{th}$ and 20$^{th}$ mutation, respectively. Amino acids that were predicted to contribute to MHC binding included basic (Arg/Lys), polar uncharged (Ser/Asn/Tyr), and non-polar residues (Phe/Leu/Ile). These residues were replaced with non-polar (Gly/Met), acidic (Asp/Glu), basic (His), or polar uncharged (Thr/Gln/Tyr) amino acids.

TABLE 3

| Mutation | Total Number of Plans with Mutation | Number of Optimal Plans with Mutation | Surface/Buried Residue |
|---|---|---|---|
| Arg118Thr | 1031 (67%) | 53 (65%) | Surface |
| Ser124Gly | 1012 (66%) | 59 (73%) | Surface |
| Ser122Gly | 954 (62%) | 57 (70%) | Surface |
| Lys95Glu | 861 (56%) | 50 (62%) | Surface |
| Phe38Gly | 848 (55%) | 46 (57%) | Surface |
| Asn12Gly | 604 (39%) | 48 (59%) | Surface |
| Lys46His | 516 (34%) | 25 (31%) | Surface |
| Tyr93His | 516 (34%) | 26 (32%) | Surface |
| Ser122Asp | 348 (23%) | 18 (22%) | Surface |
| Leu83Met | 336 (22%) | 15 (19%) | Surface |
| Asn121Gly | 262 (17%) | 11 (14%) | Surface |
| Ser124Tyr | 246 (16%) | 7 (9%) | Surface |
| Asn13His | 179 (12%) | 4 (5%) | Surface |
| Ile41Glu | 161 (11%) | 10 (12%) | Surface |
| Ile99Gln | 143 (9%) | 1 (1%) | Surface |
| Thr110Glu | 136 (9%) | 1 (1%) | Surface |
| Leu83Asn | 136 (9%) | 5 (6%) | Surface |
| Ser49Gly | 117 (8%) | 0 | Buried |
| Val120Gln | 102 (7%) | 3 (4%) | Surface |
| Ser49Ala | 69 (5%) | 0 | Buried |

The mutations were predicted to significantly reduce the binding of peptides to the MHC and produce less immunogenic variants (Table 4). In all generated peptides, it could be seen that the number of mutant hits (the number of alleles a peptide was predicted to bind) was lower than that of the wild-type peptides. For instance, the Arg to Thr mutation at position 118 in the wild-type QRMVNSFSQ (SEQ ID NO:107) peptide was predicted to delete both epitopes and resulted in a Z score of 0 across all the alleles. Some of the more immunogenic regions were harder to tackle with a single mutation. Yet, it was observed that even a single mutation could have a meaningful impact on reducing the total immunogenicity score. For instance, the Ser122Asp mutation deleted two epitopes and reduced the overall hit number from 14 to 8.

TABLE 4

| Mutation | Peptide | SEQ ID NO: | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|---|---|
| R118T | QTMVNSFSQ | 109 | | | | | | | | |
| S124G | QRMVNSFGQ | 110 | | | | | | | | |
|  | MVNSFGQST | 111 | 1.83 | | | 1.77 | | | | |
| S122G | FQRMVNGFS | 112 | 3.17 | 2.5 | 2.97 | 2.26 | 2.68 | 3.31 | | 2.87 |
|  | QRMVNGFSQ | 113 | | | | | | | | |
|  | MVNGFSQST | 114 | | | | | | | | 2.01 |
| K95E | YVEAGQIIG | 115 | | | | | | | | |
| F38G | VDFGMNIGT | 116 | | | | | | | | |
|  | FGMNIGTPV | 117 | 2.1 | | | | | | | |
|  | GMNIGTPVK | 118 | | | | | | | | |
| N12G | WLGNYKKGY | 119 | | | | | | | 2.02 | |
|  | LGNYKKGYG | 120 | | | | | | 1.98 | | |
| K46H | MNIGTPVHA | 121 | | | | | | | | |
|  | IGTPVHAIS | 122 | | | | | | | | |
|  | VHAISSGKI | 123 | 2.29 | 1.96 | | 2.84 | | | | 2.69 |
| Y93H | HVKAGQIIG | 124 | | | | | | | | |
| S122D | LHFQRMVND | 125 | | | | | | | | |
|  | FQRMVNDFS | 126 | 3.28 | 1.93 | 3.02 | | 1.75 | 2.98 | | 1.97 |
|  | QRMVNDFSQ | 127 | | | | | | | | |
|  | MVNDFSQST | 128 | | 1.72 | 1.9 | | | | | |

TABLE 4-continued

| Mutation | Peptide | SEQ ID NO: | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|---|---|
| L83M | VHRQWYMHM | 129 | | | | | | | | |
| | MSKYNVKVG | 130 | | | | | | | | |
| N121G | QRMVGSFSQ | 131 | | | | | | | | |
| S124Y | FQRMVNSFY | 132 | 2.92 | 2.75 | 2.6 | 1.88 | | 2.52 | 2.45 | 2.39 |
| | QRMVNSFYQ | 133 | | | | | | | | |
| | MVNSFYQST | 134 | | | | | | | | |
| N13H | WLNHYKKGY | 135 | | | | | | 2.21 | | |
| I41E | VDFFMNEGT | 136 | | | | | | | | |
| | FMNEGTPVK | 137 | | | 2.16 | | | | | |
| | MNEGTPVKA | 138 | | | | | | | | |
| | EGTPVKAIS | 139 | | | | | | | | |
| I99Q | YVKAGQQIG | 140 | | | | | 1.91 | | | |
| | QIGWSGSTG | 141 | | | | | | | | |

Mutations are shown in bold.

Modification of Lysostaphin Sequence for *P. pastoris* Expression

Initial attempts to make *S. simulans* lysostaphin in *P. pastoris* were hampered by the lack of protein expression. Thus, the gene was modified for expression in *P. pastoris* (Zhao, et al. (2014) supra). Briefly, the sequence of the wild-type lysostaphin was adjusted to reflect the codon preference of *P. pastoris*. Additionally, a long segment with disproportionate A+T content in the sequence was identified and disrupted. The new version of the gene (SYN lysostaphin) was found to yield up to 80 mg/L of protein in shake flask culture, and 500 mg/L in a 2 L bioreactor (Zhao, et al. (2014) supra).

Subsequent expression experiments conducted with SYN lysostaphin showed that the protein migrated as a doublet in SDS-PAGE. It was suspected that the observed doublets were due to protein N-glycosylation. Close examination of the lysostaphin sequence revealed that it contained a glycosylation sequon at position 125. The presence of the N-glycan was confirmed by PNGase treatment of the culture supernatant. Once treated, the protein migrated as a singlet in SDS-PAGE.

An attempt to disrupt the Asn125 glycosylation sequon was made by introducing conservative Asn->Gln, Asn->Ser, and Asn->Asp single point mutations. The results of this analysis indicated that these mutants exhibited similar expression levels but had 10-, 20- and 40-fold lower activity than the wild-type enzyme, respectively.

In subsequent studies, a library was constructed by saturation mutagenesis to determine which other residues besides Asn could be tolerated at position 125 and still allow for disruption of N-glycosylation sequence (Zhao, et al. (2014) supra). The library results, and subsequent alignment of lysostaphin sequence with its homologues (ALE-1 and LytM), showed that Asn125 is a conserved residue, such that focus needed to be placed on mutating other residues of the glycosylation sequon. Thus, two other mutants, Ser126Pro and Thr127Ala, were synthesized and found to successfully prevent N-glycosylation. The mutants were compared to the wild-type lysostaphin and found to exhibit equivalent activity. Since a fully active aglycosylated mutant was desired, the lysostaphin Ser126Pro was selected for further experimental evaluation with the EpiSweep algorithm.

EpiSweep Correction for Aglycosylated Lysostaphin

The Ser126Pro lysostaphin backbone was analyzed with EpiMatrix and EpiSweep to determine the epitope score and compare the most frequent mutations. The results showed that switching to the Ser126Pro mutant increased the predicted epitope score. Ser126Pro had a total epitope score of 50, as compared to epitope score of 46 for the Asn125Gln backbone (Table 2). EpiMatrix analysis also showed that Ser126Pro had five EpiBars (peptides which have a Z score of 1.64 or higher for a minimum of four alleles), while Asn125Gln had three. The Ser126Pro backbone had 15 instances of predicted top 1% binders (score>2.32), and 35 instances of top 5% MHC binders (score>1.64). Peptide [116]FQRMVNSFS[124] (SEQ ID NO:88) remained equally problematic, as in the Asn125Gln backbone, and was predicted to be highly immunogenic for all eight alleles. The four new epitopes present in Ser126Pro backbone were introduced in peptides [119]MVNSFSNPT[127] (SEQ ID NO:142) and [120]VNSFSNPTA[128] (SEQ ID NO:143) (Table 5).

TABLE 5

| Peptide | SEQ ID NO: | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|---|
| WLNNYKKGY | 89 | | | | | 1.69 | 2.12 | 1.73 | |
| LNNYKKGYG | 90 | | | | | 2.46 | | | 1.93 |

TABLE 5-continued

| Peptide | SEQ ID NO: | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|---|
| INGGMHYGV | 91 | | | | | | | | 1.9 |
| VDFFMNIGT | 92 | | | | | | | | 1.93 |
| FFMNIGTPV | 93 | 2.41 | | 1.79 | 1.93 | | | | |
| FMNIGTPVK | 94 | | | 2.19 | | | 2.06 | | |
| MNIGTPVKA | 95 | 1.68 | | | | | | | |
| IGTPVKAIS | 96 | | | | | | | 1.85 | |
| VKAISSGKI | 97 | 2.35 | 2.02 | 1.65 | 2.9 | | | | 2.75 |
| IENDGVHRQ | 98 | | | 2.06 | | | | | |
| VHRQWYMHL | 99 | | | | | | | | 1.99 |
| WYMHLSKYN | 100 | | | | 2.72 | | | | |
| YMHLSKYNV | 101 | 1.86 | | | | 2.29 | 2.72 | | 2.01 |
| LSKYNVKVG | 102 | | | | | 1.67 | | | |
| YVKAGQIIG | 103 | 1.66 | | | | 1.97 | | | |
| IIGWSGSTG | 104 | | | 1.76 | | | | | |
| WSGSTGYST | 105 | 1.95 | | | 1.92 | | | | |
| LHFQRMVNS | 106 | | | | | | | 2.05 | |
| FQRMVNSFS | 88 | 3.4 | 2.54 | 3.41 | 2.27 | 2.66 | 3.37 | 2.24 | 2.86 |
| MVNSFSNPT | 142 | 2 | | 1.9 | 2.79 | | 1.78 | | 2.25 |
| VNSFSNPTA | 143 | | | 2.03 | | 1.96 | 2.05 | | 2.55 |

EpiSweep analysis of the Ser126Pro backbone yielded a total of 2,333 plans, 96 of which were evaluated as Pareto optimal plans at mutational loads of two to eight mutations (compared with the Asn125Gln backbone which yielded a total of 1,533 plans, 81 of which were Pareto optimal). Table 6 compares the most frequent mutations found in the Asn125Gln and Ser126Pro backbones. The mutation pattern was not significantly changed after switching to the new backbone. Most mutations remained in the top 15, with exception of only four mutations: Ser122Gly, Ser124Gly, Leu83Met and Ile99Gln moved to positions 16, 18, 23 and 24, respectively. The most frequent mutation, Arg118Thr, remained as dominant in both backbones. While in the Asn125Gln backbone all 15 most frequent mutations were surface exposed residues, the new backbone pushed a buried residue, Ser49Gly, to the top 15. Most mutations were similarly represented in total plans and optimal plans, with an exception of Ser124Gly, which changed from being present in 72% of the plans, to not being present in any of the optimal plans selected with the Ser126Pro backbone. The most frequent 15 mutations (evaluated based on the Asn125Gln backbone) were present in 2-82% of total plans generated using the Ser126Pro backbone, and in 0-88% of Pareto optimal plans.

TABLE 6

| Mutation | Percentage of Plans with Mutation | Percentage of Optimal Plans with Mutation | Ranking Order change |
|---|---|---|---|
| Arg118Thr | 67->82% | 65->88% | 1->1 |
| Ser124Gly | 66->9% | 72->0% | 2->18 |
| Ser122Gly | 62->10% | 70->4% | 3->16 |
| Lys95Glu | 56->53% | 61->58% | 4->2 |
| Phe38Gly | 55->18% | 56->25% | 5->11 |
| Asn12Gly | 39->49% | 59->78% | 6->3 |
| Lys46His | 33->18% | 30->18% | 7->10 |
| Tyr93His | 33->45% | 32->58% | 8->4 |
| Ser122Asp | 22->43% | 22->54% | 9->5 |
| Leu83Met | 21->4% | 18->1% | 10->23 |
| Asn121Gly | 17->26% | 13->32% | 11->7 |
| Ser124Tyr | 16->12% | 8->9% | 12->15 |
| Asn13His | 11->15% | 4->10% | 13->14 |
| Ile41Glu | 10->21% | 12->26% | 14->9 |
| Ile99Gln | 9->2% | 1->3% | 15->24 |
| Thr110Glu | 8->25% | 1->27% | 16->8 |
| Leu83Asn | 8->10% | 6->8% | 17->17 |
| Ser49Gly | 7->18% | 0->27% | 18->12 |
| Val120Gln | 6->6% | 3->0% | 19->21 |
| Ser49Ala | 4->7% | 0->0% | 20->20 |

The 15 mutations based on the Asn125Gln backbone were still predicted to significantly reduce the binding of residues to MHC II and produce less immunogenic variants in the Ser126Pro backbone (Table 7). The predicted deletions were largely similar to those obtained with Asn125Gln. The overall mutant hit rate with Asn125Gln was 35 (40 with Ser126Pro) and the wild-type hit rate is 84 (88 with Ser126Pro), so the two backbones targeted roughly the same number of epitopes.

The one significant difference observed was that the Arg118Thr mutation, which deleted two epitopes in the Asn125Gln backbone, did not delete any epitopes in the Ser126Pro backbone. However, closer examination showed that Arg118Thr helped other mutations delete more epitopes. For instance, when Arg118Thr was combined with Ser122Asp, the two mutations deleted a total of 13 epitopes. As such, the Arg118Thr mutation was not eliminated from further study. However, the Ser122Gly mutation was excluded since it targeted the same residue as Ser122Asp but only deleted three epitopes (as opposed to 10 that Ser122Asp was predicted to remove).

sidered a sufficient evaluation of the effect of single point mutations on the protein.

The analysis of lysostaphin single point mutants revealed that all variants were expressed in *P. pastoris*. Thus, none of the most frequent EpiSweep mutations abolished expression. The two mutations with the lowest expression levels were Arg118Thr and Ser124Tyr, with 47% and 35% of the wild-type expression level, respectively. Furthermore, 13 of the lysostaphin variants had activity that either equaled or exceeded that of the wild-type enzyme. Point mutant Phe38Gly was one of the two mutations with activity lower than the wild-type (69%). The second mutation with low activity was Ser124Tyr, with 16% of the wild-type activity. Since Phe38Gly and Ser124Tyr did not meet threshold activity levels of >70% of the wild-type activity, neither enzyme was included in further studies. While the expression level of the Arg118Thr mutation was less than 50% of

TABLE 7

| | | SEQ | Z Scores | | | | | | | |
|---|---|---|---|---|---|---|---|---|---|---|
| Mutation | Peptide | ID NO: | DRB1* 0101 | DRB1* 0301 | DRB1* 0401 | DRB1* 0701 | DRB1* 0801 | DRB1* 1101 | DRB1* 1301 | DRB1* 1501 |
| S124G | MVNSFGQST | 111 | 1.92 | | | 2.15 | | | | 1.74 |
| S122G | FQRMVNGFS | 112 | 3.17 | 2.5 | 2.97 | 2.26 | 2.68 | 3.31 | | 2.87 |
| | MVNGFSQST | 114 | | | 1.66 | 1.94 | | | | 2.14 |
| K95E | YVEAGQIIG | 115 | | | | | | | | |
| F38G | VDFGMNIGT | 116 | | | | | | | | |
| | FGMNIGTPV | 117 | 2.1 | | | | | | | |
| | GMNIGTPVK | 118 | | | | | | | | |
| N12G | WLGNYKKGY | 119 | | | | | | 2.02 | | |
| | LGNYKKGYG | 120 | | | | | 1.98 | | | |
| K46H | MNIGTPVHA | 121 | | | | | | | | |
| | IGTPVHAIS | 122 | | | | | | | | |
| | VHAISSGKI | 123 | 2.29 | 1.96 | | 2.84 | | | | 2.69 |
| Y93H | HVKAGQIIG | 124 | | | | | | | | |
| S122D | LHFQRMVND | 125 | | | | | | | | |
| | FQRMVNDFS | 126 | 3.28 | 1.93 | 3.02 | | 1.75 | 2.98 | | 1.97 |
| | MVNDFSNPT | 144 | | 1.86 | 2.26 | | | | | |
| | VNDFSNPTA | 145 | | | | | | | | |
| L83M | VHRQWYMHM | 129 | | | | | | | | |
| | MSKYNVKVG | 130 | | | | | | | | |
| N121G | VGSFSNPTA | 146 | | | | | | | | 2.11 |
| S124Y | FQRMVNSFY | 132 | 2.92 | 2.75 | 2.6 | 1.88 | | 2.52 | 2.45 | 2.39 |
| | MVNSFYQST | 134 | | | | 2.02 | | | | |
| N13H | WLNHYKKGY | 135 | | | | | | | 2.21 | |
| I41E | VDFFMNEGT | 136 | | | | | | | | |
| | FMNEGTPVK | 137 | | | 2.16 | | | | | |
| | MNEGTPVKA | 138 | | | | | | | | |
| | EGTPVKAIS | 139 | | | | | | | | |
| I99Q | YVKAGQQIG | 140 | | | | | 1.91 | | | |
| | QIGWSGSTG | 141 | | | | | | | | |

Mutations are shown in bold.

Expression Level and Activity of Lysostaphin Variants

Even though the algorithm was focused on deimmunization of only the catalytic domain, it is important to note that the single point mutants were tested in the context of a full-length, mature protein to ensure proper protein folding. Since lysostaphin is secreted into media, a simple analysis of lysostaphin activity from the culture supernatant was conthe wild-type enzyme, this enzyme was further analyzed given the number of epitopes removed by this mutation.

Backbone Flexibility Adjustment

All designs obtained using EpiSweep assumed a rigid backbone (referred to herein as "rigid" backbone designs). However, since proteins are known for their high level of flexibility, it was posited that keeping the backbone fixed in the post-processing energy minimization step could compromise the accuracy of deimmunized variants by resulting in imprecise energy assessments. It has been observed that completely rigid designs differ drastically in energy-epitope score landscape from the designs in which the side chains were allowed to relax (while the backbone was fixed) during minimization (Parker, et al. (2013) supra). Thus, to achieve flexibility in a computationally-permitting way, additional post-processing energy minimization of the EpiSweep designs was performed (referred to herein as "flexible" backbone designs). The results of this analysis showed that there was indeed a visible movement between the two backbones.

EpiSweep Analysis of Chosen Mutations

As described above, the expression and activity of the 15 most frequent mutations were analyzed. Based upon this analysis, two mutations were dropped due to unsatisfactory activity values. In addition, Ser122Gly was removed as it targeted the same residue as Ser122Asp, which deleted 10 epitopes compared to the three epitopes of the Ser122Gly mutation. The most frequent mutation, Arg118Thr, did not delete any epitopes in the context of the Ser126Pro backbone and had a relatively low expression level. However, Arg118Thr was maintained as it assisted other mutations in targeting epitopes. For instance, when combined with Ser122Asp, the Arg118Thr mutation targeted a total of 13 epitopes. As a result, the data set contained different mutations: Ser124Gly, Ser122Asp, Asn121Gly, Arg118Thr, Ile99Gln, Lys95Glu, Tyr93His, Leu83Met, Lys46His, Ile41Glu, Asn13His, and Asn12Gly.

EpiSweep analysis was performed once again, but the algorithm was constrained to use only the 12 well-tolerated mutations. The mutational load was allowed to vary from two to eight mutations and the algorithm was forced not to introduce mutations at the active site (His32, Asp36, His82, His113, and His115). Since it was observed that the Ser122Asp mutation was an extremely efficient epitope remover, the algorithm was constrained to include this mutation in all generated plans. As before, the algorithm generated Pareto optimal plans and an additional 19 suboptimal plans at each mutational load. The lowest epitope score was found to be 24, and could only be achieved with plans containing eight mutations. The highest epitope score was 40, and the plans with this score had only the forced Ser122Asp mutation.

A number of plans along the Pareto optimal curve (designs that have the lowest possible rotamer energy at a fixed epitope score and mutational load) were selected. EpiSweep analysis yielded rigid backbone plans, and a total of 14 Pareto optimal plans at mutational loads ranging from two to eight mutations were selected, with the epitope score in the range of 24 (lowest) to 36. Since the wild-type lysostaphin backbone had an epitope score of 50, it was posited that this range covered designs that were significantly deimmunized.

To address the protein flexibility concern, 14 designs that were energy minimized post-processing (flexible backbone designs) were also included. The designs at the same epitope scores and mutational loads as the rigid backbone designs were selected so that the two different methods of obtaining variants could be directly evaluated. For instance, if a Pareto optimal rigid plan with eight mutations and an epitope score of 24 were chosen, a flexible backbone design at the same mutational load and epitope score was selected. When faced with several options, the flexible backbone design of the lowest rotamer energy was chosen. Because they were energy minimized, these designs did not appear on the Pareto frontier. It should be noted that the two mutation plan was shared between the rigid and flexible backbone designs.

Expression Level and Activity of Synthesized Variants

Each lysostaphin variant was grown in shake flask culture and examined for expression level by SDS-PAGE. The plans that were found to express at a meaningful level in culture supernatants (by SDS-PAGE detection) were further characterized for their relative specific activities. The results showed that out of 28 rigid and flexible backbone plans, only 11 were expressed. Expression levels of all variants except Rigid 1 were found to be lower than that of the wild-type lysostaphin.

All of the plans (except Flex 1; SEQ ID NO:32) had activity lower than that of the wild-type enzyme, but only two had activity lower than the commercial *E. coli*-produced lysostaphin. It was noted that there was a significant difference between the activity of the wild-type lysostaphin produced in *P. pastoris* and ssLys. Out of a total of 11 expressing plans, six were flexible backbone designs and five were rigid backbone designs. Rigid design mutational load ranged from two to six, and flexible from two to eight.

The activity level of the plans decreased as the number of mutations increased. This trend was better observed in flexible rather than the rigid backbone designs. Similarly, in flexible plans, it was found that the expression level decreased with an increase in the mutational load. This trend was not observed in rigid backbone designs, as their expression level remained low regardless of the mutational load. The only rigid design that had a high expression level was the two mutation design Rigid 1, which was shared between the rigid and flexible designs (also referred to as Flex 14).

Analysis of Non-Expressing Mutants

Since less than a half of the synthesized designs expressed at a meaningful level, the non-expressing designs were analyzed for their mutational patterns. This analysis showed that expressing and non-expressing designs shared the majority of the mutations. Some mutations, such as Leu83Met, Tyr93His, and Lys95Glu, were present in most of the non-expressing plans, but only in a few expressing plans. Similarly, Arg118Thr was present in only a few expressing plans but, unlike any other mutation (the forced Ser122Asp mutation excluded), it could be found in all of the non-expressing plans (Table 8).

TABLE 8

| Design ID | N12G | N13H | I41E | K46H | L83M | Y93H | K95E | I99Q | R118T | N121G | S122D | S124G | No. Mutations |
|---|---|---|---|---|---|---|---|---|---|---|---|---|---|
| Wild-Type[E] | | | | | | | | | | | | | 0 |
| Flex 1[E] | | | E | | | | | Q | | | D | | 3 |
| Flex 5[E] | | | | H | | | | Q | | G | D | | 4 |
| Flex 6[E] | G | | E | | | | | Q | | G | D | | 5 |
| Flex 8[E] | G | | E | | M | | | Q | | G | D | | 6 |
| Flex 9[E] | G | | E | | M | | E | Q | | G | D | G | 8 |

TABLE 8-continued

| Design ID | N12G | N13H | I41E | K46H | L83M | Y93H | K95E | I99Q | R118T | N121G | S122D | S124G | No. Mutations |
|---|---|---|---|---|---|---|---|---|---|---|---|---|---|
| Flex 10$^E$ | G | | E | | | | | | | G | D | | 4 |
| Flex 14$^E$ | | | E | | | | | | | | D | | 2 |
| Rigid 1$^E$ | | | E | | | | | | | | D | | 2 |
| Rigid 2$^E$ | | | | H | | | | | T | | D | | 3 |
| Rigid 3$^E$ | | | | H | | H | E | | T | | D | | 4 |
| Rigid 13$^E$ | | H | | H | | | | | T | | D | | 4 |
| Rigid 14$^E$ | | H | | H | | H | E | | T | | D | | 5 |
| Flex 2$^N$ | | | E | H | | | | | T | | D | G | 4 |
| Flex 3$^N$ | | | E | | | | E | Q | T | | D | | 4 |
| Flex 4$^N$ | | | E | | | H | E | Q | T | | D | | 5 |
| Flex 7$^N$ | G | | E | | | | E | Q | T | | D | G | 6 |
| Flex 11$^N$ | G | | E | | | H | E | Q | T | | D | G | 7 |
| Flex 12$^N$ | | H | E | | | | E | Q | T | | D | | 5 |
| Flex 13$^N$ | | H | E | | | H | E | Q | T | | D | | 6 |
| Rigid 4$^N$ | G | | E | H | M | H | E | | T | | D | | 7 |
| Rigid 5$^N$ | G | | E | | M | | E | Q | T | | D | G | 7 |
| Rigid 6$^N$ | G | | E | | M | | E | | T | | D | | 5 |
| Rigid 7$^N$ | G | | E | | M | | | | T | | D | | 4 |
| Rigid 8$^N$ | G | | E | | M | H | E | | T | | D | | 7 |
| Rigid 9$^N$ | G | | E | | | | | | T | | D | | 3 |
| Rigid 10$^N$ | G | | E | | | H | E | | T | | D | | 5 |
| Rigid 11$^N$ | | H | | H | M | | | | T | | D | | 4 |
| Rigid 12$^N$ | | H | | H | M | H | E | | T | | D | | 7 |

$^E$Expressed.
$^N$Not expressed.
The double line divides expressing and non-expressing plans.

Since earlier results showed that mutation Arg118Thr had a relatively low expression level (less than 50% of wild type), it was posited that the observed lack of expression in the majority of the synthesized plans may have been due to the Arg118Thr mutation. To test this, the mutation was reverted back to wild-type in all plans having this mutation. Characterization of Both Original and Reverted Plans All expressed plans were purified for further characterization of activity and stability. Furthermore, all of the designs that originally had the Arg118Thr mutation, but now had the wild-type residue at the same position (reverted plans), were evaluated. The results of this analysis are shown in Table 9.

TABLE 9

| Design ID | Flexible Energy | Rigid Energy | Episcore | % Wild-Type Activity | MIC (µg/mL) | Tm (° C.) |
|---|---|---|---|---|---|---|
| Wild-Type | −3929 | −48.5 | 50 | 100 | 0.0351 | 59.2 |
| Flex 1 | −4130 | −47.2 | 34 | 63 | 0.0833 | 55.4 |
| Flex 5 | −3954 | −49.7 | 32 | 61 | 0.1042 | 55.7 |
| Flex 6 | −3978 | −49.3 | 28 | 58 | 0.2083 | 54.1 |
| Flex 8 | −3974 | −49.8 | 26 | 60 | 0.2083 | 52.9 |
| Flex 9 | −4005 | −50.8 | 24 | 57 | 0.1250 | 53.0 |
| Flex 10 | −3904 | −49.4 | 30 | 62 | 0.0729 | 57.5 |
| Flex 14 | −4056 | −47.4 | 36 | 69 | 0.0833 | 58.6 |
| Rigid 1 | −4056 | −47.4 | 36 | 69 | 0.0833 | 58.6 |
| Rigid 2 | −3784 | −55.5 | 34 | 72 | 0.1042 | 49.2 |
| Rigid 13 | −3699 | −57.1 | 32 | 71 | 0.0521 | 46.9 |
| Flex 2* | −4016 | −49.5 | 35 | 77 | 0.0833 | 58.4 |
| Flex 3* | −4166 | −47.7 | 33 | 61 | 0.2500 | 56.2 |
| Flex 4* | −4143 | −50.7 | 33 | 36 | 0.2083 | 57.5 |
| Flex 7* | −4084 | −49.0 | 29 | 67 | 0.2500 | 54.7 |
| Flex 11* | −4059 | −47.2 | 29 | 76 | 0.1250 | 52.8 |
| Flex 12* | −4079 | −49.4 | 31 | 54 | 0.1250 | 54.8 |
| Flex 13* | −4056 | −52.3 | 31 | 71 | 0.1667 | 54.2 |
| Rigid 2* | −3957 | −49.5 | 37 | 80 | 0.1042 | 57.1 |
| Rigid 3* | −3884 | −53.0 | 35 | 79 | 0.0833 | 57.3 |
| Rigid 4* | −3884 | −55.3 | 26 | 55 | 0.2500 | 54.1 |
| Rigid 5* | −4080 | −55.5 | 27 | 66 | 0.1667 | 52.5 |
| Rigid 6* | −4013 | −49.9 | 29 | 64 | 0.2083 | 53.3 |
| Rigid 7* | −3977 | −49.4 | 31 | 80 | 0.0729 | 55.0 |
| Rigid 9* | −3980 | −48.9 | 33 | 79 | 0.0729 | 56.5 |
| Rigid 10* | −3993 | −52.4 | 31 | 77 | 0.1458 | 55.6 |
| Rigid 11* | −3867 | −51.7 | 33 | 70 | 0.0313 | 55.7 |
| Rigid 13* | −3871 | −51.2 | 35 | 92 | 0.0625 | 56.9 |
| Rigid 14* | −3884 | −54.6 | 33 | 75 | 0.1042 | 56.1 |

Reverted plans are indicated with *.

Out of a total of 32 plans (original and reverted), 28 were found to express. The 28 that expressed well were purified and characterized for their activity and stability. During the preliminary analysis, Rigid 3 and Rigid 14 were found to express weakly in the culture supernatant. Reverted versions of Rigid 8 and 12 did not significantly improve expression. It is possible that these four plans had low expression levels due to the presence of other mutations besides Arg118Thr, but no obvious mutational patterns could be found. All other plans in which the Arg118Thr mutation was changed back to the wild-type sequence were found to express well. As such, the Arg118Thr mutation appeared to affect expression for the majority of the plans.

The results showed that the variants had high levels of activity and stability, as compared to the wild-type enzyme. Activity values were expressed as % of the wild-type activity, and ranged from 92% (Rigid 13*) to 36% (Flex 4*). The observed MIC values were close to the wild-type, with the highest being 0.25 µg/ml (Flex 3*, Flex 7* and Rigid 4*). Tm values were also similar to that observed in the wild-type enzyme, with the lowest Tm showing a decrease in stability of 12.3° C. (Rigid 13, Table 9).

This analysis indicated that an increase in the mutational load resulted in a decrease in activity/Tm values of the variants and an increase in MIC values. On average, rigid designs had a higher specific activity and lower MIC values than flexible designs. Flexible designs, however, had a better overall stability than rigid designs, as evidenced by higher average Tm values. Based on the results of a two-tailed t-test, the differences observed between the two design groups were statistically significant (p-values<0.03).

The designs were divided into the seven different groups (Table 10) for further characterization. Using the data from Table 9, the Pearson correlation coefficients between the flexible/rigid energies, mutational loads, activity, and stability for each design group were calculated.

TABLE 10

| | Pearson (P-value) | | | | | | |
|---|---|---|---|---|---|---|---|
| | Flexible Original | Rigid Original | Flexible Reverted | Rigid Reverted | All Flexible | All Rigid | All Designs |
| NM vs. Act. | −0.86 (0.01) | 0.55 (0.63) | 0.26 (0.57) | −0.80 (0.00) | −0.04 (0.88) | −0.61 (0.02) | −0.38 (0.04) |
| NM vs. MIC | 0.53 (0.22) | −0.59 (0.59) | −0.03 (0.95) | 0.73 (0.01) | 0.36 (0.21) | 0.69 (0.01) | 0.56 (0.00) |
| NM vs. Tm | −0.85 (0.02) | −0.94 (0.21) | −0.85 (0.02) | −0.12 (0.73) | −0.79 (0.00) | −0.09 (0.76) | −0.24 (0.22) |
| FE vs. Act. | −0.36 (0.43) | 0.77 (0.44) | 0.72 (0.07) | 0.20 (0.56) | 0.21 (0.47) | 0.08 (0.79) | 0.39 (0.04) |
| FE vs. MIC | 0.22 (0.63) | −0.34 (0.78) | −0.79 (0.04) | −0.35 (0.29) | −0.38 (0.18) | −0.34 (0.23) | −0.48 (0.01) |
| FE vs. Tm | −0.05 (0.92) | −1.00 (0.03) | −0.14 (0.77) | −0.02 (0.95) | −0.10 (0.74) | −0.59 (0.03) | −0.49 (0.01) |
| RE vs. Act. | 0.78 (0.04) | −0.8 (0.4) | 0.25 (0.59) | 0.52 (0.1) | 0.3 (0.3) | 0.36 (0.21) | −0.07 (0.75) |
| RE vs. MIC | −0.4 (0.35) | 0.27 (0.83) | 0.05 (0.91) | −0.4 (0.17) | −0.2 (0.56) | −0.2 (0.46) | 0.05 (0.79) |
| RE vs. Tm | 0.63 (0.13) | 1.00 (0.02) | −0.2 (0.66) | 0.09 (0.8) | 0.17 (0.57) | 0.55 (0.04) | 0.48 (0.01) |
| No. of Designs | 7 | 3 | 7 | 11 | 14 | 14 | 28 |

NM, No. of Mutations;
Act., Activity;
FE, Flexible Energy;
RE, Rigid Energy.

When considered together, all 28 designs showed a weak positive correlation between the number of mutations and the MIC value (Table 10, All Designs). Thus, as mutational load of the variants increased, their activity decreased (MIC value increased). A stronger positive correlation between the number of mutations and MIC was found in rigid reverted and all rigid plans.

Other correlations that were not obvious when all the plans were analyzed together become apparent when designs were evaluated separately. For instance, it was observed that a strong negative correlation existed between the mutational load and activity in the original flexible plans, reverted rigid plans, and all rigid plans. A strong negative correlation was also found between the number of mutations and Tm values in flexible original, flexible reverted, and all flexible plans.

Overall, strong correlations were not observed between energy and activity/stability terms when all designs were considered together. The only meaningful correlation observed was a weak negative correlation between the flexible energy and Tm (Table 10, All Designs). The correlations observed between the flexible energy and activity terms had opposite signs than what was expected. On the other hand, correlations between the rigid energy and activity were not significant, while the correlation between rigid energy and Tm had incorrect sign. Thus, to further examine whether energy was a reliable predictive tool, the correlations between energy components and experimentally determined activity and stability values were evaluated.

Even though flexible and rigid energies were not great predictors of activity, it was found that energy due to solvent interactions could be used instead (Table 11). As expected for a functional predictor, solvent energy had a negative (although weak) correlation with activity, and a stronger positive correlation with MIC values.

TABLE 11

| | Pearson Correlation Coefficient | | |
|---|---|---|---|
| | Activity | MIC | Tm |
| Flexible Energy | 0.391 | −0.479 | −0.0488 |
| Energy Due to Intermolecular Forces | 0.402 | −0.0514 | −0.0282 |
| Energy Due to Charge-Charge Interactions | 0.449 | −0.605 | −0.291 |
| Energy Due to Solvent Interactions | −0.397 | 0.556 | 0.064 |
| Rigid Energy | −0.065 | 0.054 | 0.484 |

Taken together, these results showed that flexible backbone energy was a relatively good predictive tool of stability, while energy due to solvent interactions seemed to be the best predictor for experimental activity observed using a MIC assay.

Characterizing Immunoreactivity of Lysostaphin Variants

The predicted epitopes in the wild-type lysostaphin catalytic domain were broadly distributed throughout the lysostaphin sequence, but the majority of the epitopes could be grouped into five clusters (FIG. 2). Most epitopes were predicted to have a high number of binding events.

To evaluate the relative immunogenicity of the variants, a total of 26 synthetic peptides spanning the sequence of the lysostaphin catalytic domain were designed. In particular, focus was placed on the five immunogenic clusters shown in FIG. 2. For each cluster listed, a wild-type peptide and the corresponding mutated peptide were designed. The mutated peptides contained both the single mutation and mutational combination that appeared in plans.

In the context of synthetic peptides, each mutation was evaluated for its predicted potential to eliminate epitopes. EpiBars (peptides that had a Z score of 1.64 or higher for a minimum of four alleles on the EpiMatrix immunogenicity scale) were found in cluster 2 ($^{45}$VKAISSGKI$^{53}$, SEQ ID NO:97), cluster 3 ($^{80}$WMHLSKYNV$^{88}$, SEQ ID NO:147), and cluster 5 ($^{116}$FQRMVNSFS$^{124}$, SEQ ID NO:88; $^{119}$MVNSFSNPT$^{127}$, SEQ ID NO:142; and $^{120}$VNSFSNPTA$^{128}$, SEQ ID NO:143).

Each peptide from was experimentally evaluated for its binding potential to eight MHC II alleles in a high-throughput MHC II binding assay. The EpiSweep-generated mutations generally lessened the binding of the peptides to the MHC. Out of the 168 pair-wise comparisons, mutations decreased binding affinity in 73 cases, had no effect in 60 cases and increased binding in 35 cases. A peptide was classified as a strong binder if an $IC_{50}$ value of less than 0.1 µM was observed, moderate if an $IC_{50}$ value was in the 0.1-1 µM range, and weak if an $IC_{50}$ value was in the 1-10 µM range. All peptides above 10 µM were considered non-binders.

Using the 10 µM cutoff to separate binders from non-binders, EpiMatrix predictions (at 5% threshold) were compared with the MHC II binding results. The percentage of true positives (correctly predicted binders), true negatives (correctly predicted non-binders), false positives (incorrectly predicted binders), and false negatives (incorrectly predicted non-binders) were calculated. The results showed that the overall predictive success rate was 70%, a result that was slightly lower than the previously published studies, which cite the predictive rate as ~76% (Groot, et al. (2011) Immunome Res. 7:2-7; Moise, et al. (2013) Hum. Vaccin. Immunother. 9:2060-2068). Allele-specific examination revealed that the predictions were in the previously observed range for DRB1*0101, 0301, 0401, and 0701. No data could be found for 0801. It was observed that for 1301 the majority of peptides registered as either weak or non-binders. This observation would suggest that the test peptide used for 1301 was likely a really strong binder, and as such had skewed the data toward a smaller predictive success rate. Similarly, the predictive rate for 1101 and 1501 was lower than previously reported and was also thought to have contributed to the lower overall rate.

The cluster 1 wild-type (C1WT) epitope was predicted to bind four out of eight MHC II alleles tested. In accordance with the prediction, both Asn12Gly and Asn13His mutations disrupted MHC II binding. Asn13His mutation was better at removing DRB1*0801 and 1101 epitopes, and the mutations were equally good at removing DRB1*1501 epitope. However, the mutations also resulted in strong binding for DRB1*0101 (Asn12Gly), and weak binding for DRB1*1301 (Asn13His) (Table 12).

TABLE 12

| Peptide | $IC_{50}$, µM (No. of predicted epitopes) | | | | | | | |
|---|---|---|---|---|---|---|---|---|
| | 0101 | 0301 | 0401 | 0701 | 0801 | 1101 | 1301 | 1501 |
| C1WT[1] | 214.9 (0*) | >250 (0*) | >250 (0*) | >250 (0*) | 13.73 (2) | 0.94 (1*) | 136.70 (1) | 101.50 (1) |
| N12G[2] | <0.01 (0) | >250 (0*) | >250 (0*) | >250 (0*) | 58.63 (1) | 5.16 (1*) | >250 (0*) | >250 (0*) |
| N13H[3] | >250 (0*) | >250 (0*) | >250 (0*) | >250 (0*) | >250 (1) | 4.13 (0) | 41.63 (1) | >250 (1) |

[1]SAQWLNNYKKGYGYG (SEQ ID NO: 148).
[2]SAQWLGNYKKGYGYG (SEQ ID NO: 221).
[3]SAQWLNHYKKGYGYG (SEQ ID NO: 222).
*Positive correlation between predicted binders and experimentally observed binders.
Binding thresholds set to 5% for predictions and 10 µM for experiments.

In the case of cluster 2 wild-type (C2WT) epitope, binding was predicted for seven MHC II alleles, with multiple epitopes for DRB1*0101, 0301, 0401, 0701, and 1501 (Table 13). The mutations were predicted to target the seven alleles except for DRB1*0101 and 0701, and for those three alleles (in addition to 0401) an increase in binding was observed. One exception was the Lys46His mutant, which showed a two-fold decrease in binding to 0101. Lys46His also reduced binding to 1101, while Ile41Glu and Ile41Glu/Lys46His resulted in strong binding. All mutants had lower affinity for 0301, as predicted. Ile41Glu and Lys46His showed reduced binding to 1501, while Ile41Glu/Lys46His emerged as a strong binder. The combination of mutations was particularly bad as it resulted in increased binding for all alleles but 0301. The high binding affinity of this cluster could be explained by the large number of epitopes. Out of a total of 13 epitopes across the eight alleles, the mutations were predicted to disrupt only four epitopes. Furthermore, this particular region contained an EpiBar, and previous studies show that these epitopes tend to be more immunogenic than epitopes that do not have EpiBars (Groot, et al. (2011) supra).

TABLE 13

| Peptide | $IC_{50}$, µM (No. of predicted epitopes) | | | | | | | |
|---|---|---|---|---|---|---|---|---|
| | 0101 | 0301 | 0401 | 0701 | 0801 | 1101 | 1301 | 1501 |
| C2WT[1] | 0.22 (2*) | 60.10 (2) | 13.73 (3) | 8.19 (2*) | >250 (0*) | 10.08 (1) | 103.90 (1) | 2.37 (2*) |
| I41E[2] | 0.59 (2*) | >250 (1) | 3.48 (3*) | 7.51 (2*) | >250 (0*) | 146.10 (0*) | 142.60 (0*) | 7.44 (1*) |

TABLE 13-continued

| Peptide | IC$_{50}$, µM (No. of predicted eptitopes) | | | | | | | |
|---|---|---|---|---|---|---|---|---|
| | 0101 | 0301 | 0401 | 0701 | 0801 | 1101 | 1301 | 1501 |
| K46H[3] | 0.49 (2*) | 151.62 (1) | 1.65 (2*) | 4.46 (2*) | 87.48 (0*) | 18.29 (1) | 212.00 (0*) | 2.55 (2*) |
| 41_46[4] | <0.01 (2*) | >250 (1) | <0.01 (2*) | 14.33 (2) | >250 (0*) | <0.01 (1*) | >250 (0*) | <0.01 (1*) |

[1]GVDFFMNIGTPVKAISSGKIV (SEQ ID NO: 223).
[2]GVDFFMNEGTPVKAISSGKIV (SEQ ID NO: 224).
[3]GVDFFMNIGTPVHAISSGKIV (SEQ ID NO: 225).
[4]GVDFFMNEGTPVHAISSGKIV (SEQ ID NO: 226).
*Positive correlation between predicted binders and experimentally observed binders.
Binding thresholds set to 5% for predictions and 10 µM for experiments.

The cluster 3 wild-type (C3WT) epitope was a predicted binder of DRB1*0101, 0701, and 1101, with multiple epitopes for 0801 and 1501 (Table 14). C3WT was experimentally shown to also weakly bind 1301. Leu83Met mutation was anticipated to disrupt binding in only 0801 and 1501. In agreement with the prediction, an approximately five-fold decrease in binding for 0801 was found. However, more than a two-fold decrease in 0701 (strong to moderate), ten-fold reduction for 1101, and a ~2000-fold drop for 0101 (strong to weak) was also observed. Increased binding was detected for 1501 (opposite of what was predicted), 1301, and 0301. For 1501, a shift from a weak to a moderate binder was observed, while 1301 remained a weak binder, and 0301 a non-binder. Thus, the Leu83Met mutation was largely productive as it reduced binding to four alleles and did not cause a change of classification for two other alleles (peptides remained weak or non-binders).

ing. One exception was mutation Lys95Glu, which was predicted to reduce binding to 0101 and 0801, but instead resulted in stronger binding (or remained as a strong binder) across all eight alleles. The mutations significantly decreased binding to 0101: Tyr93His, Ile99Gln, and Tyr93His/Lys95Glu/Ile99Gln transformed a strong binder into a weak or non-binder, and Tyr93His/Lys95Glu turned a strong binder into a moderate one. All mutations and their combinations reduced the binding for 0301 from weak to non-binders. Similarly, all mutations but Tyr93His/Ile99Gln resulted in significant decreases in binding to 1101 (strong to weak/non-binder), and all mutants except Tyr93His/Lys95Glu lessened the binding for 1301. Lastly, only Ile99Gln and Tyr93His/Lys95Glu/Ile99Gln eliminated binding to 1501 (strong to weak/non-binder). Mutations Ile99Gln, Tyr93His/Ile99Gln, and Tyr93His/Lys95Glu slightly increased binding affinity for 0701 by turning a

TABLE 14

| Peptide | IC$_{50}$, µM (No. of predicted eptitopes) | | | | | | | |
|---|---|---|---|---|---|---|---|---|
| | 0101 | 0301 | 0401 | 0701 | 0801 | 1101 | 1301 | 1501 |
| C3WT[1] | <0.01 (1*) | 155.43 (0*) | 38.12 (0*) | 0.41 (1*) | 0.14 (2*) | <0.01 (1*) | 54.69 (0*) | 9.51 (2*) |
| L83M[2] | 32.39 (1) | 114.83 (0*) | >250 (0*) | 2.09 (1*) | 0.37 (1*) | 0.11 (1*) | 27.38 (0*) | 4.42 (1*) |

[1]GVHRQWYMHLSKYNVKVGD (SEQ ID NO: 149).
[2]GVHRQWYMEMSKYNVKVGD (SEQ ID NO: 150).
*Positive correlation between predicted binders and experimentally observed binders.
Binding thresholds set to 5% for predictions and 10 µM for experiments.

The cluster 4 wild-type (C4WT) epitope was predicted to bind three out of eight MHC II alleles tested: DRB1*0101, 0401, and 0801. In addition to 0101 and 0401, binding was observed for 0301 (weak), 1101 (strong), 1301 (weak), and 1501 (strong), but not for 0801 (Table 15). In accordance with the prediction, the mutations disrupted MHC II binding.

non-binder C4WT into a weak binder. Overall, mutations Tyr93His, Ile99Gln, Tyr93His/Lys95Glu, Lys95Glu/Ile99Gln, and Tyr93His/Lys95Glu/Ile99Gln were the most productive across all eight alleles. Tyr93His/Lys95Glu/Ile99Gln was particularly good, as it eliminated binding to all eight alleles.

TABLE 15

| Peptide | IC$_{50}$, µM (No. of predicted eptitopes) | | | | | | | |
|---|---|---|---|---|---|---|---|---|
| | 0101 | 0301 | 0401 | 0701 | 0801 | 1101 | 1301 | 1501 |
| C4WT[1] | <0.01 (1*) | 31.40 (0*) | <0.01 (1*) | 92.86 (0*) | 62.54 (1) | 1.69 (0) | 78.47 (0*) | <0.01 (0) |
| Y93H[2] | 102.80 (0*) | >250 (0*) | >250 (1) | 181.90 (0*) | >250 (0*) | >250 (0*) | >250 (0*) | <0.01 (0) |
| K95E[3] | <0.01 (0) | 1.90 (0) | <0.01 (1*) | 4.81 (0) | 12.24 (0*) | 6.32 (0) | 25.69 (0*) | <0.01 (0) |
| I99Q[4] | 31.74 (0*) | >250 (0*) | 6.16 (0) | 93.12 (0*) | >250 (1) | 24.32 (0*) | >250 (0*) | 66.06 (0*) |

TABLE 15-continued

| | IC$_{50}$, μM (No. of predicted epitopes) | | | | | | | |
|---|---|---|---|---|---|---|---|---|
| Peptide | 0101 | 0301 | 0401 | 0701 | 0801 | 1101 | 1301 | 1501 |
| 93_99[5] | <0.01 (0) | >250 (0*) | <0.01 (0) | 60.49 (0*) | >250 (0*) | >250 (0*) | >250 (0*) | <0.01 (0) |
| 93_95[6] | 9.98 (0) | 110.20 (0*) | 25.52 (1) | 24.94 (0*) | 30.93 (0*) | 25.02 (0*) | 18.92 (0*) | 0.06 (0) |
| 95-99[7] | <0.01 (0) | >250 (0*) | 25.77 (0*) | 103.70 (0*) | >250 (0*) | 25.43 (0*) | >250 (0*) | <0.01 (0) |
| 939599[8] | >250 (0*) | >250 (0*) | >250 (0*) | 179.30 (0*) | >250 (0*) | >250 (0*) | >250 (0*) | >250 (0*) |

[1]DYVKAGQIIGWSGSTGY (SEQ ID NO: 151).
[2]DHVKAGQIIGWSGSTGY (SEQ ID NO: 152).
[3]DYVEAGQIIGWSGSTGY (SEQ ID NO: 153).
[4]DYVKAGQQIGWSGSTGY (SEQ ID NO: 154).
[5]DHVKAGQQIGWSGSTGY (SEQ ID NO: 155).
[6]DHVEAGQIIGWSGSTGY (SEQ ID NO: 156).
[7]DYVEAGQQIGWSGSTGY (SEQ ID NO: 157).
[8]DHVEAGQQIGWSGSTGY (SEQ ID NO: 158).
*Positive correlation between predicted binders and experimentally observed binders.
Binding thresholds set to 5% for predictions and 10 μM for experiments.

The cluster five wild-type (C5WT) epitope was predicted to bind all eight alleles, with multiple epitopes for all except DRB1*0301 and 0801. Binding was experimentally observed in all but 0301 and 1301, with 0701 and 0801 measuring as weak binders (Table 16). The most deimmunizing mutations were Arg118Thr/Ser122Asp/Ser124Gly and Asn121Gly/Ser122Asp/Ser124Gly, as they each significantly reduced binding affinity to six alleles. For the 0301 allele, the IC$_{50}$ values of the mutants decreased slightly, but the peptides remained as non-binders. This result agreed with the EpiSweep prediction, in which the mutations disrupted binding for all eight alleles. Asn121Gly diminished binding to four alleles, while Ser124Gly and Asn121Gly/Ser122Asp reduced binding to three. Asn121Gly/Ser122Asp also slightly increased the binding to 0301 (non-binder to weak binder). Similarly, Arg118Thr and R118T/S122D lessened the affinity to two alleles, but showed an increase in binding to 0301 (non-binder to weak binder). The observed increase in binding affinity for 0301 allele in mutation combinations could be explained by the fact that Ser122Asp was predicted to introduce one epitope for the allele. In fact, it was observed that Ser122Asp changed a non-binder peptide C5WT into a moderate binder.

TABLE 16

| | IC$_{50}$, μM (No. of predicted epitopes) | | | | | | | |
|---|---|---|---|---|---|---|---|---|
| Peptide | 0101 | 0301 | 0401 | 0701 | 0801 | 1101 | 1301 | 1501 |
| C5WT[1] | 0.15 (2*) | >250 (1) | 0.05 (3*) | 15.23 (2) | 22.01 (1) | <0.01 (3*) | >250 (3) | <0.01 (3*) |
| R118T[2] | <0.01 (2*) | 68.39 (1) | <0.01 (3*) | 23.14 (2) | 57.70 (1) | <0.01 (3*) | >250 (3) | <0.01 (3*) |
| N121G[3] | <0.01 (2*) | >250 (1) | 6.13 (2*) | 17.40 (2) | >250 (1) | 6.41 (2*) | >250 (2) | <0.01 (3*) |
| S122D[4] | <0.01 (1*) | 9.42 (2*) | <0.01 (2*) | >250 (0*) | 150.00 (1) | <0.01 (1*) | >250 (0*) | <0.01 (1*) |
| S124G[5] | <0.01 (2*) | >250 (1) | 0.04 (2*) | 150.70 (2) | >250 (1) | 0.30 (2*) | >250 (3) | <0.01 (3*) |
| 18_22[6] | <0.01 (1*) | 28.16 (1) | <0.01 (2*) | 110.60 (0*) | >250 (0*) | <0.01 (1*) | >250 (0*) | <0.01 (0) |
| 182224[7] | 7.43 (1*) | 132.90 (0*) | 7.52 (2*) | >250 (0*) | >250 (0*) | 14.13 (1) | >250 (0*) | 0.42 (0) |
| 21_22[8] | <0.01 (1*) | 77.42 (1) | <0.01 (2*) | >250 (0*) | 210.10 (0*) | 28.54 (1) | >250 (0*) | <0.01 (0) |
| 212224[9] | 0.18 (1*) | 116.40 (0*) | 5.55 (2*) | >250 (0*) | >250 (0*) | 13.45 (1) | >250 (0*) | 24.20 (0*) |

[1]HLHFQRMVNSFSNPTAQ (SEQ ID NO: 159).
[2]HLHFQTMVNSFSNPTAQ (SEQ ID NO: 160).
[3]HLHFQRMVGSFSNPTAQ (SEQ ID NO: 161).
[4]HLHFQRMVNDFSNPTAQ (SEQ ID NO: 162).
[5]HLHFQRMVNSFGNPTAQ (SEQ ID NO: 163).
[6]HLHFQTMVNDFSNPTAQ (SEQ ID NO: 164).
[7]HLHFQTMVNDFGNPTAQ (SEQ ID NO: 165).
[8]HLHFQRMVGDFSNPTAQ (SEQ ID NO: 166).
[9]HLHFQRMVGDFGNPTAQ (SEQ ID NO: 167).
*Positive correlation between predicted binders and experimentally observed binders.
Binding thresholds set to 5% for predictions and 10 μM for experiments.

Figure 3:
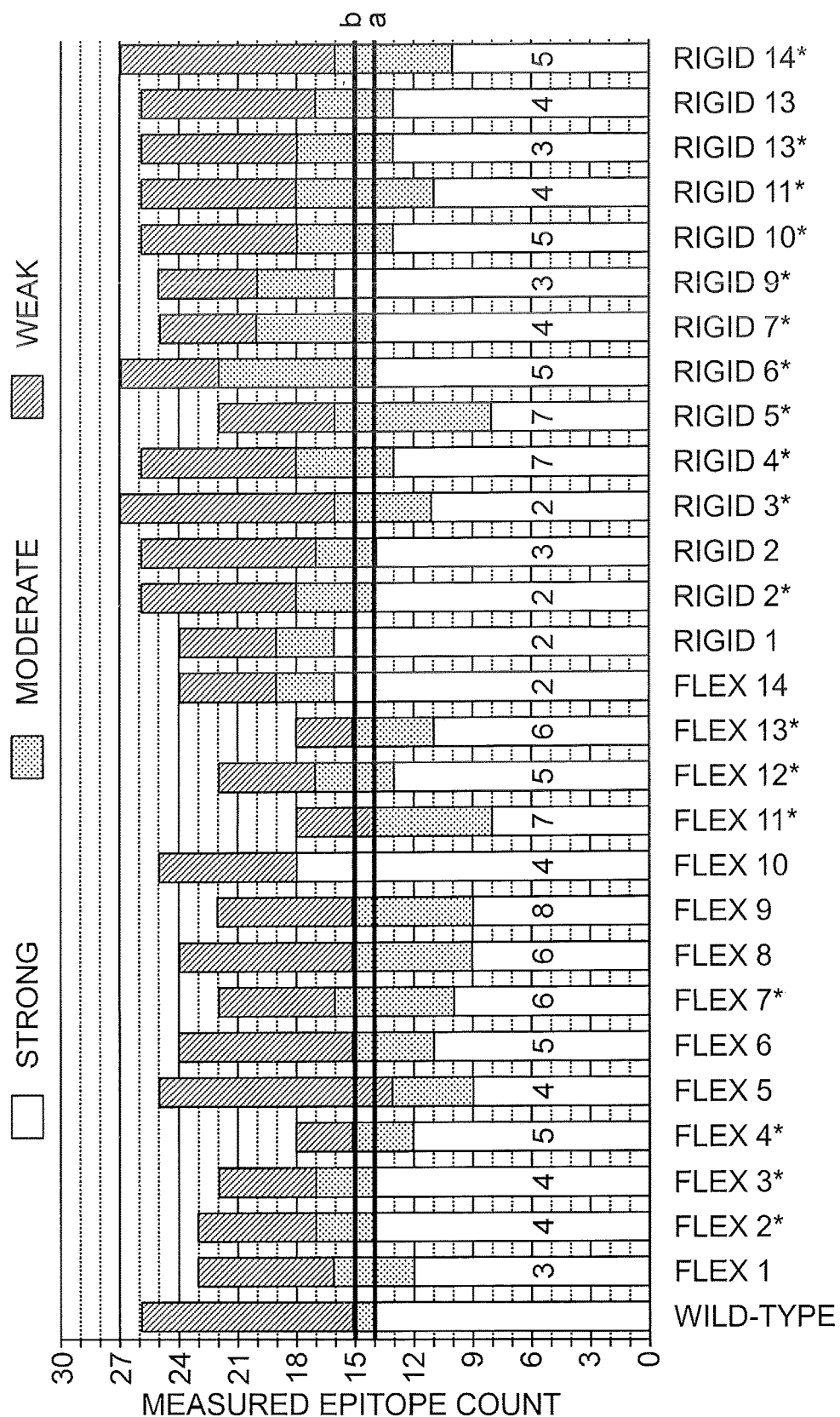
FIG. 3 shows an aggregate of immunogenicity scores calculated for full-length designs. Each peptide in a design was evaluated as strong ($IC_{50}<1$ μM), moderate (1 μM<$IC_{50}$<10 μM), or weak (10 μM<$IC_{50}$<100 μM) binder to the eight MHC class II alleles. Strong, moderate and weak binders were then summed to obtain the aggregate score shown in the figure. The line with an "a" indicates the number of strong binders in the wild type lysostaphin catalytic domain, while the line with a "b" shows the number of moderate binders. Numbers on the bars represent the mutational load of each design. *Indicates reverted designs.

To compare immunogenicity between the full-length designs, the aggregate epitope score for each design was calculated (FIG. 3). This analysis showed that the wild-type lysostaphin catalytic domain had a total of 26 binding interactions (or epitopes): 14 strong, 1 moderate, and 11 weak. The enzyme also had 14 non-binding interactions. In comparison, 18 of the designs had an epitope score lower than the wild-type, six had the same score, and only four had epitope scores that exceeded the wild-type (by maximum of two epitopes). All but three of the designs also had a higher number of non-binding interactions as compared to the wild-type. The minimum number of epitopes was 18, and it was present in three of the variants: Flex 4* (5 mutations), Flex 11* (7 mutations), and Flex 13* (6 mutations). Furthermore, 18 of the designs showed a reduction in the number of strong binders, as compared to the wild-type.

A strong negative correlation was noted between the number of mutations and the number of experimentally observed strong binders (Pearson coefficient −0.69). Similarly, a positive correlation was observed between the epitope score and the number of strong binders (Pearson coefficient 0.52). At the same time, no correlation was found between the mutational load/epitope score and the total number of binders. This result indicated that the algorithm was not only reducing binding, but was also primarily targeting the strong epitopes.

In general, more deimmunized plans were found among flexible than rigid backbone designs. On average, there were fewer strong, moderate, weak, and total binding interactions found in flexible than rigid plans. This trend may be explained in part by the fact that most rigid designs were reverted and missing one mutation. The lowest number of strong binders, eight, was observed in Flex 11* and Rigid 5*. As expected, the most aggressive plan, Flex 9, showed a significant decrease in immunogenicity, with a total of only 22 binding interactions: 9 strong, 6 moderate, and 7 weak.

In Vitro Analysis of Flex 5 and Flex 9 Variants

Variants Flex 5 and Flex 9 were expressed, purified, and characterized in biological duplicate. As an additional control, wild-type LST was obtained from a commercial supplier and analyzed in parallel. The apparent melting temperatures of both variants were consistent with values obtained during preliminary testing, but their specific rates of bacterial lysis were found to be somewhat higher upon more rigorous analysis (Table 17). Importantly, the deimmunized variants were equivalent to or better than commercially sourced LST in both assays. The enzymes' antibacterial activity was further quantified by assessing minimal inhibitory concentration (MIC) toward four strains of *S. aureus*. The Flex 5 MIC for strain SA113 was equivalent to that of wild-type and commercial LST, and it was within a single 2-fold serial dilution for three clinical isolates, including MRSA strain 3425-3. Variant Flex 9 also retained good bactericidal/bacteriostatic activity, preventing outgrowth of all four strains at 200 ng/ml (~7 nM) or less. Given the fact that the LST$^{CAT}$ variants encoded four or eight mutations, respectively, their high levels of anti-staphylococcal activity were striking.

TABLE 17

| Design ID | % WT Lytic Rate | Tm (° C.) | MIC (μg/mL) Strain SA113 | Strain 6445 | Strain 3425-1 | Strain 3425-3 |
|---|---|---|---|---|---|---|
| Wild-type | 100 ± 30 | 59.0 ± 0.4 | 0.02 ± 0.00 | 0.03 ± 0.01 | 0.04 ± 0.02 | 0.03 ± 0.02 |
| Commercial | 60 ± 20 | 47.3 ± 0.4 | 0.03 ± 0.00 | 0.03 ± 0.00 | 0.04 ± 0.01 | 0.03 ± 0.00 |
| Flex 5 | 70 ± 30 | 55.8 ± 0.2 | 0.02 ± 0.01 | 0.06 ± 0.04 | 0.11 ± 0.09 | 0.05 ± 0.03 |
| Flex 9 | 60 ± 20 | 52.8 ± 0.3 | 0.04 ± 0.01 | 0.13 ± 0.07 | 0.2 ± 0.1 | 0.2 ± 0.1 |

Figure 4C:
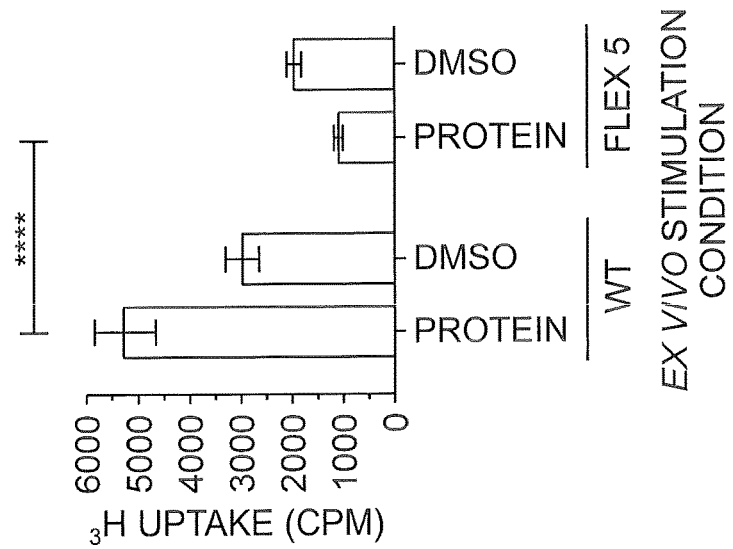
FIGS. 4A-4C shows in vivo efficacy and immunogenicity analysis of Flex 5 and Flex 9 variants.
Figure 4B:
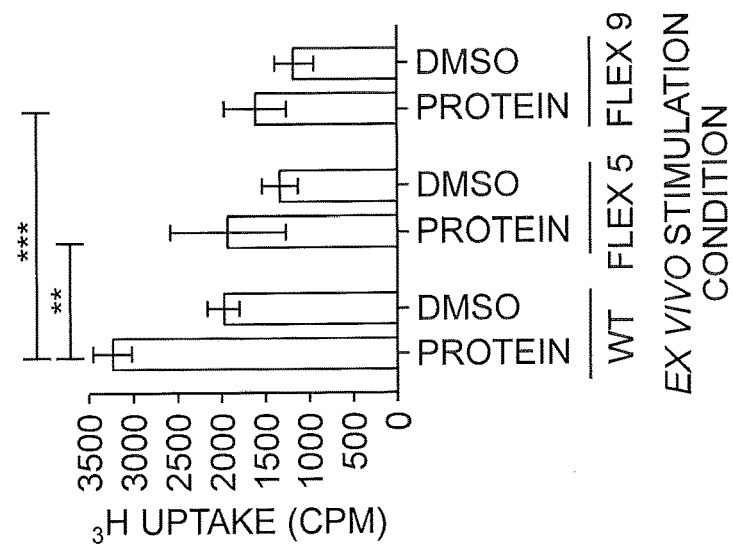
Figure 4A:
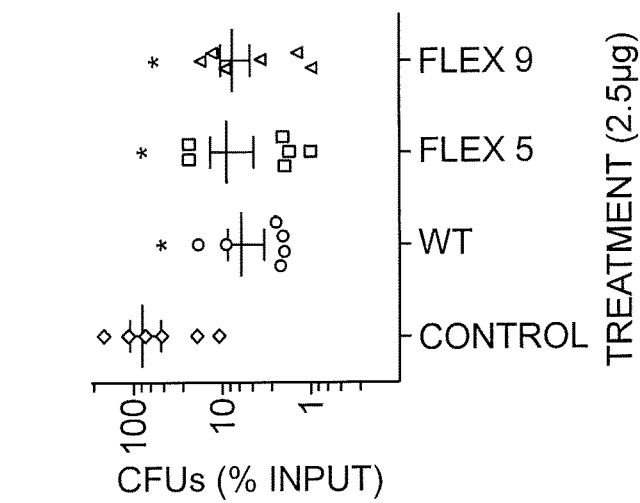

* Errors are standard deviation from a minimum of biological duplicates measured in triplicate In Vivo Efficacy and Immunogenicity of Flex 5 and Flex 9 Variants To assess antibacterial activities in a more clinically relevant fashion, a murine lung infection model was employed, which uses an *S. aureus* clinical isolate. Mice were infected with live bacteria via oropharyngeal aspiration, and one hour later they were treated via the same route with a solution containing 2.5 μg of wild-type LST, variant Flex 5, or variant Flex 9. Twenty-four hours post-infection, mice were sacrificed, lungs were harvested, and viable bacterial counts were determined by plating serial dilutions of lung homogenate. All three enzymes yielded a statistically significant 10-fold reduction in bacterial burden relative to a saline buffer control (one-way ANOVA P=0.007, Tukey post test), but there was no significant difference between the three treatments (FIG. 4A). Thus, the deimmunized candidates retained wild-type efficacy in the infected and inflamed lung environment.

In vivo immunogenicity was evaluated using NOD/SCID/$Y_c^{-/-}$ mice that had been surgically humanized with human immune cells, liver tissue, and thymus tissue (HUMI mice). Following transplantation of human tissues at six weeks of age, HUMI mice were allowed to mature and develop circulating repertoires of human B and T cells. At 14 weeks post-transplantation, mice were divided into three groups of four each and immunized subcutaneously with 100 μg of wild-type LST, Flex 5, or Flex 9 in adjuvant. Thirteen days post-immunization, mice were sacrificed, splenocytes were harvested and pooled for each group, and the pooled cells were subjected to ex vivo restimulation with their cognate proteins. Cell proliferation was measured by tritiated thymidine uptake at 72 hours. The stimulation index (protein vs. DMSO proliferative response) was less than 2-fold for wild-type LST (FIG. 4B), but it bears noting that T cells from humanized mice are widely known to exhibit impaired function. In particular, humanized mouse splenocytes have been shown to exhibit poor ex vivo proliferative response even in the presence of potent stimulatory agents such as phytohaemagglutinin, ionomycin-PMA, and anti-CD3/anti-CD28 antibody cocktails (Watanabe, et al. (2009) *Internatl. Immunol.* 21:843-858). Moreover, following two to three in vivo immunizations with the powerful antigen keyhole limpet hemocyanin in complete Freund's adjuvant (CFA), restimulated humanized mouse splenocytes fail to produce IFN-Y or IL-4 (Watanabe, et al. (2009) *Internatl. Immunol.* 21:843-858) and exhibit only a 2- to 6-fold stimulation index ex vivo (Tonomura, et al. (2008) *Blood* 111:4293-6). Thus, the significant (P=0.0005, two way ANOVA) 1.6-fold stimulation index of the wild-type LST splenocytes is a reasonable indicator of an antigen specific immune response, particularly given the fact that the mice of the current study received but one immunization. Relative to the wild-type immunized group, pooled splenocytes from Flex 5 and Flex 9 immunized mice exhibited significantly reduced proliferation (FIG. 4B). After background subtraction, Flex 5 pooled cells showed a 50% reduced response and Flex 9 pooled cells a 65% reduced response.

In addition to inherent immunogenicity in the context of a naïve immune system, the extent to which a deimmunized protein might evade an established memory response directed against the native sequence was also considered. Due to the long time-frame of such a study and the short lifespan of HUMI mice, the memory response in transgenic DR4 mice was assessed. This homozygous strain has an intact murine immune system, with the exception that they bear a chimeric class II MHC based on the peptide binding domains from human HLA DRA and DRB1*0401 (Ito, et al. (1996) *J. Exp. Med.* 183:2635-44). This stable transgenic model has a normal, healthy lifespan enabling extended studies, yet its antigen presenting cells exhibit human peptide binding specificity. Ten DR4 mice were immunized and repeatedly boosted with sub-cutaneous injections of wild-type LST. Nineteen weeks after the final boost, they were divided into two groups of five each such that each group exhibited similar average antibody titers. Mice were then rechallenged with either 100 μg wild-type LST or 100 μg variant Flex 5. Thirteen days later, splenocytes were harvested, pooled for each group, and subjected to ex vivo restimulation with the cognate protein from the final rechallenge. Similar to the results in the HUMI mice, ex vivo restimulation of DR4 splenocytes with wild-type LST yielded a 1.8-fold stimulation index (FIG. 4C). It bears noting that similarly small stimulation indices in DR2, DR3, and DQ8 transgenic mice have been shown to correlate with antigen specific antibody production and to be indicative of antigen specific immune responses (Depil, et al. (2006) *Vaccine* 24:2225-9). Thus, the significant (P=0.0002, two way ANOVA) 1.8-fold stimulation index seen here was a reasonable indicator of an anti-drug immune response. In contrast to wild-type LST rechallenged mice, proliferation of pooled splenocytes from the Flex 5 challenge group was at or below background levels (FIG. 4C). Thus, immune cells primed to recognize wild-type LST exhibited reduced activity upon rechallenge with Flex 5, indicating that the deimmunized variant effectively evaded the memory response directed against the wild-type enzyme.

EXAMPLE 2

Deimmunization of Lysostaphin Catalytic and Cell Wall Binding Domains Against HLA Allele DRB1*0401

Overview

This analysis was carried out to demonstrate that depletion of putative T cell epitopes in LST would mitigate the anti-drug antibody response and consequently enhance therapeutic efficacy. Epitope depleted variants were developed using two distinct computationally-guided strategies: structure-based design of individual deimmunized variants followed by empirical improvement (designated "opt" variants) and structure-based design and screening of combinatorial libraries enriched in functionally deimmunized members (designated "lib" variants). Humanized HLA-transgenic mice were used to assess the efficiency with which each method deleted putative immunogenic epitopes and thereby prevented formation of anti-LST antibodies in vivo. Subsequently, a recurrent bacteremia model was used to gauge the extent to which LST deimmunization enabled clearance of systemic *S. aureus* infections. This systematic comparison between deimmunized variants and their wild-type counterpart provides direct experimental evidence of the clinically relevant connections between putative T cell epitopes, in vivo immunogenicity, and therapeutic efficacy.

Figure 5:
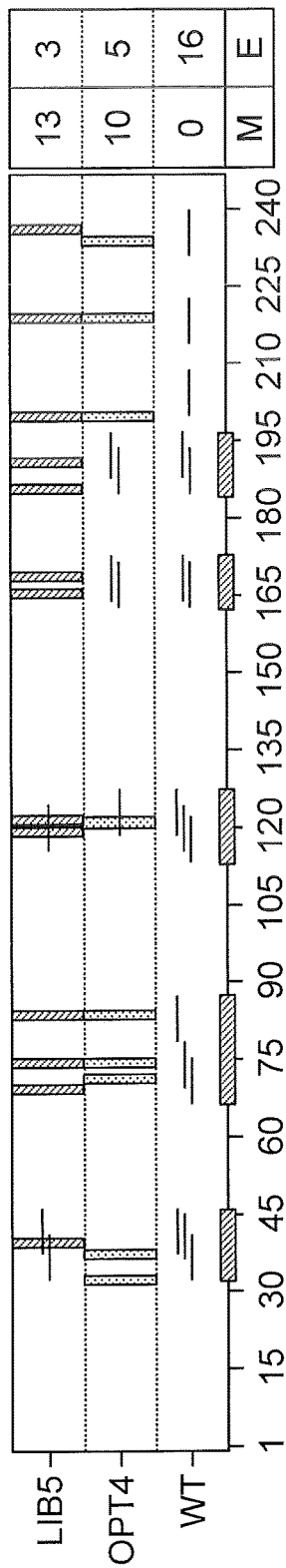
FIG. 5 shows the predicted DR4 T cell epitopes for variants Lib5 (top), Opt4 (middle), and $LST^{WT}$ (bottom). Nonamer epitopes are shown as horizontal lines at the corresponding position in the LST amino acid sequence (X-axis). $LST^{WT}$ contains 16 putative epitopes, Opt4 contains 5, and Lib5 contains only three. Regions of overlapping epitope density in $LST^{WT}$ are highlighted with filled blocks on the x-axis. Positions of deimmunizing mutations in Lib5 (top) and in Opt4 (middle) are shown as filled vertical bars. The mutation (M) and epitope (E) counts for each design are indicated at right.

As a proof of concept, focus was placed on allele DRB1*0401 (hereafter DR4), which is highly prevalent in North American and European populations. At a 5% threshold (i.e., peptides among the top 5% of predicted binders), the ProPred analysis tool (Singh & Raghava (2001) *Bioinformatics* 17:1236-7) predicted 16 DR4 restricted T cell epitopes within wild-type LST ($LST^{WT}$ epitope score=16). The peptide epitopes were arrayed as both overlapping clusters and isolated nonamers distributed throughout the protein's sequence and structure (FIG. 5). Interestingly, ProPred predicted more epitopes for DR4 than for any of the seven other representative DRB1 alleles: 0101, 0301, 0701, 0801, 1101, 1301, and 1501. Considering any single allele, therefore, the DR4 model represented a high bar for global protein redesign.

Materials and Methods

Materials. Primers were ordered with standard desalting from IDT Technologies (Coralville, Iowa). Restriction enzymes and Phusion DNA polymerase for molecular cloning were purchased from New England Biolabs (Ipswich, Mass.). All other reagents and supplies were from VWR Scientific (Philadelphia, Pa.), unless specifically noted.

*P. pastoris* expression vector pPIC9 and *P. pastoris* strain GS115(his4) were purchased from Invitrogen (Grand Island, N.Y.). *E. coli* DH5☐ [F− Φ80/acZΔM15 Δ(lacZYA-argF) U169 recA1 endA1 hsdR17 (rK−, mK+) phoA supE44 λ− thi-1 gyrA96 recA1], *S. aureus* strain SA113, and MRSA strain USA400 were from the American Type Culture Collection (Manassas, Va.).

LST Homology Models. As the crystal structure of lysostaphin was not available, homology models were constructed for the two domains. Three template structures from LytM were selected for the catalytic domain (2B0P:A, 2B44:A and 1QWY:A) (Firczuk, et al. (2005) *J. Mol. Biol.* 354:578-90; Odintsov, et al. (2004) *J. Mol. Biol.* 335:775-85). The three template structures share significant sequence identity (95%~97%), yet they have highly mobile loops (Firczuk, et al. (2005) *J. Mol. Biol.* 354:578-90) around conserved active sites. The highest sequence identity against the lysostaphin catalytic domain was 46.7%, which is sufficient to build quality model structures (Baker & Andrej (2001) *Science* 294:93-96). Initial homology models were built using MODELLER. A template-less region ($^{24}$PLGIN GG$^{30}$; SEQ ID NO:168) was modeled using a loop modeling method, FREAD (Choi & Deane (2010) *Proteins* 78:1431-1440), which selected a sequence-similar loop from 1GMN:A ($^{180}$PRGEEGG$^{186}$; SEQ ID NO:169) (Lietha, et al. (2001) *EMBO J.* 20:5543-5555). The cell wall binding domain was constructed using a single template structure (1R77:A, cell wall targeting domain structure of ALE-1, a lysostaphin homolog) with a high sequence identity (83.5%) (Lu, et al. (2006) *J. Biol. Chem.* 281:549-558). The best models were selected in terms of the DOPE statistical potential function score (Shen & Sali (2006) *Protein Sci.* 15:2507-2524). The catalytic domain models were minimized against AMBER99sb with GB/SA in order to relax the predicted loop (Hornak, et al. (2006) *Proteins* 65:712-725; Still, et al. (1990) *J. Am. Chem. Soc.* 112:6127-6129).

Preprocessing of Mutation Choices. For each domain, three iterations of PSI-BLAST (Altschul, et al. (1997) *Nucleic Acids Res.* 25:3389-3402) were run against the non-redundant database to find homologs. Multiple sequence alignments were constructed for the identified sequences, and processed to identify those that were not too gappy (at most 25%), and were sufficiently similar to LST (at least 35%) but sufficiently different from each other (at most 90% identical). A set of 114 representative catalytic domain homologs and 23 representative cell wall binding domain sequences remained. Amino acids were identified at each position in each multiple sequence alignment and subsequently used as possible mutations for design. Particular positions and mutations deemed functionally important were not allowed to mutate (positions 32, 36, 82, 113, 115, 117, 118, 119, 125, 126, 127 were locked down; specific mutations Y33T, F38A, F38G, M39A, I41R, S124Y and R118T were disallowed). A second filtering step kept only those mutations predicted to delete at least one epitope, as determined using ProPred at a 5% threshold. To avoid presumed deleterious effects, mutations to and from proline and cysteine were also excluded.

The mutational choices were expanded for library design, since screening allows for riskier substitutions. In particular, Chou-Fasman (Chou & Fasman (1974) *Biochem.* 13:222-45) propensities were used to identify residues likely to be acceptable in the wild-type secondary structure environment, according to a stringent threshold of 1.5. In addition, since the library was constructed with degenerate oligonucleotides that can incorporate additional amino acids beyond the desired ones, these additions were allowed, as long as the desired to undesired ratio within a degenerate oligonucleotide remained above 2:3.

Structure-Based Design of Individual Variants. In order to generate epitope depleted designs, the structure-based deimmunization method EpiSweep was applied to each domain as described in Example 1. OSPREY (ver. 2.0) (Chen, et al. (2009) *Proc. Natl. Acad. Sci. USA* 106:7678-7678) was used to assess one- and two-body energy terms for possible rotamers (Lovell, et al. (2000) *Proteins* 40:389-408) for the mutational choices, according to the AMBER force field (Pearlman, et al. (1995) *Comput. Phys. Commun.* 91:1-41) and a reference energy (Lippow & Tidor (2007) *Curr. Opin. Biotechnol.* 18:305-311). ProPred (Singh & Raghava (2001) *Bioinformatics* 17:1236-7) at a 5% threshold was used to assess DR4 epitope (HLA Allele DRB1*0401) content, characterizing each 9 mer as either a binder or a non-binder. It was found that at least seven mutations were required to deplete all the predicted DR4 epitopes in the catalytic domain; six were required to fully deplete the cell wall binding domain. A set of 20 energy optimal and near-optimal fully depleted designs were identified for each domain via the EpiSweep optimization algorithm. The most energy optimal catalytic domain design contained a mutation at Ser124, which analysis has identified as being potentially detrimental. However, the alternative double mutation Asn121Gly and Ser122Gly is predicted to remove the same epitope, yet these two mutations manifest higher experimentally determined activity than $LST^{WT}$. The energy difference between the most energy optimal design (containing a detrimental Ser124 mutation) and the alternative double mutation design was marginal (−294.94 and −293.9). Thus, a design (Opt1) was selected so as to possess the most energy optimal design for the cell wall binding domain and the alternative double mutation in the C-terminal portion of the catalytic domain (Asn121Gly and Ser122Gly).

Structure-Based Design of Deimmunized Libraries. In order to design combinatorial libraries enriched in stable, deimmunized variants, a method called EpiSOCoM was developed, which augments the SOCoM structure-based library design approach with epitope analysis, and employs a sweep-based Pareto optimization algorithm (Parker, et al. (2013) *J. Comput. Biol.* 20:152-65) to simultaneously optimize both energy and epitope content. Given a set of possible positions at which to mutate and possible amino acids to incorporate at those positions, along with a desired library size, EpiSOCoM selects a subset of the positions and subsets of the substitutions at those positions. It thereby specifies the construction of a library composed of all combinations of the substitutions and corresponding wild-type residues. EpiSOCoM optimizes a library for the average energy score and the average epitope score over its constituent variants, so that in general variants will be "good". Its Pareto optimization algorithm identifies all library designs (positions and substitutions) making undominated trade-offs between the two scores, in that no other library design is better for both.

In order to enable rapid assessment of structure-based energies without explicit rotameric modeling of each variant, SOCoM employs a Cluster Expansion (Grigoryan, et al. (2009) *Nature* 458:859-64; Grigoryan, et al. (2006) *PLoS Comput. Biol.* 2:e63) (CE) technique that expresses structure-based properties in terms of a protein-specific function of amino acid sequence. Here, Rosetta (Rohl, et al. (2004) *Methods Enzymol.* 383:66-93) was employed in a preprocessing step to model and evaluate energies of random LST variants based on the allowed mutational choices. These structural training sets allowed CE to express the energy Ψ for a possible LST variant S via a sum over position-specific one- and two-body sequence potentials:

$$\Psi(S)=\Sigma_i\psi_i(a_i)+\Sigma_{i,j}\psi_{i,j}(a_i, a_j) \quad (1)$$

where the sums involve amino acid $a_i$ at position i and $a_j$ at position j. A total of 9000 catalytic domain and 6000 cell wall binding domain models were used to train CE models, following the CE guidelines. These were then able to make accurate predictions for the energies of new random variants in a non-overlapping testing set (of size ~20% that of the training set), achieving correlations between the CE sequence potential and Rosetta energies of 0.8 for the catalytic domain and 0.9 for the cell wall binding domain. This modeling step thus enables fast, accurate prediction of energies within the "inner loop" of design optimization.

In order to assess a library without enumerating all its variants (not tractable when optimizing over the massive design space of possible libraries), SOCoM employs library-averaged position-specific scores. For example, if the set {Arg, Lys} were to be incorporated at one position, then the energetic contribution of that position, averaged over all variants the library, would be the average of the Arg energy and the Lys energy; similarly the pair-wise contribution from that position and another incorporating {Asp, Glu}, averaged over the library, would be the average of Arg:Asp, Arg:Glu, Lys:Asp, and Lys:Glu. Thus, given the allowed mutations, SOCoM precomputes $\overline{\psi}_i$, the average energetic contributions of possible subsets of amino acids that could be chosen at a position i, and $\overline{\psi}_{i,j}$, the average for pair of positions i and j. It then evaluates the average energy $\overline{\Psi}$ over a whole library T with an equation analogous to that for a single variant:

$$\overline{\Psi}(T)=\Sigma_i\overline{\psi}_i(T_i)+\Sigma_{i,j}\overline{\psi}_{i,j}(T_i, T_j) \quad (2)$$

where the sums now involve sets of amino acids $T_i$ at position i and $T_j$ at position j. Thus assessment of a library within the optimization is as efficient as assessment of a single variant.

To develop EpiSOCoM, it was also necessary to "lift" the epitope score to library-averaged contributions, in a manner analogous to SOCoM's treatment of energy scores. If amino acids $\{T_i, T_{i+1}, \ldots, T_{i+8}\}$ were to be incorporated at the nine contiguous positions starting at i, then the average epitope score contribution $\bar{e}$ from the various 9 mer combinations of amino acids is calculated as:

$$\bar{e}_i = \frac{\sum_{a_i \in T_i, a_{i+1} \in T_{i+1}, \cdots a_{i+1} \in T_{i+8}} e(a_i a_{i+1} \ldots a_{i+8})}{|T_i| \cdot |T_{i+1}| \ldots |T_{i+2}|} \quad (3)$$

where the sum is over each combination of amino acids, one from each set, and the function e(·) gives the epitope score of the 9 mer. Then the average epitope score, Ξ, of the library is simply the sum over all 9 mers:

$$\Xi = \sum_{i=1}^{n-S} \bar{e}_i \quad (4)$$

SOCoM uses an integer linear programming formulation to choose an optimal set of positions and sets of amino acids so as to optimize Eq. 2 subject to library size constraints. With EpiSOCoM, there are two objectives, energy (Eq. 2) and epitope score (Eq. 4). Since there is no a priori means to determine the best balance between these incommensurate properties, EpiSOCoM generates all Pareto optimal designs representing the best balance, enabling subsequent characterization of the trade offs and selection of suitable designs. To identify Pareto optimal designs, it employs a sweep algorithm based on that of EpiSweep. At each step in the sweep, average library energy is optimized (Eq. 2) according to a constraint on the average epitope score (Eq. 4). The constraint is successively tightened, so that each library must have a better epitope score (and thus worse energy) than the previous one. The Pareto optimization is implemented as an iterative layer over a constrained version of SOCoM, which in turn uses the IBM CPLEX integer programming solver to optimize each design.

Protein Expression, Purification and Characterization. LST and its derivatives were secreted from *P. pastoris*. Briefly, recombinant *Pichia* strains were cultured in a 2.5 L bioreactor (Applicon Biotechnology), and the proteins were captured from the supernatant by polyethylene glycol-6000 (PEG-6000) precipitation and purified to homogeneity by SP SEPHAROSE F.F. cation exchange chromatography. Endotoxin was removed from the protein preparation by TRITON-X114 extraction (Liu, et al. (1997) *Clin. Biochem.* 30:455-63). Protein expression levels were estimated by densitometry analysis of SDS-PAGE gels. The activities of proteins were assessed by determination of minimal inhibitory concentrations (MIC) against *S. aureus* strain SA113, and are reported as a normalized percentage relative to the MIC dilution determined for $LST^{WT}$ (i.e., 50% activity is 2-fold higher MIC relative to wild-type, and 25% activity is 4-fold higher MIC relative to wild type).

Library Construction and Screening. LST libraries were constructed by splice overlapping PCR with the primers shown in Table 18.

TABLE 18

| Mutations | Primer | Sequence (5'->3') | SEQ ID NO: |
|---|---|---|---|
| Library A | | | |
| Y33NDY, F38SF, T43KT | Forward | GGTATGCACDATGGTGTTGACTTCTYTATGAA CATCGGTAMGCCAGTCAAG | 170 |
| | Reverse | CTTGACTGGCKTACCGATGTTCATARAGAAGT CAACACCATHGTGCATACC | 171 |
| I70KRI, V75DEVV, W79TRSW, S84SRG | Forward | GGTTTGADAGAGAACGACGGTGWSCACAGACA AWSGTACATGCACTTGVGTAAGTAC | 172 |
| | Reverse | GTACTTACBCAAGTGCATGTACSWTTGTCTGT GSWCACCGTCGTTCTCTHTCAAACC | 173 |
| V120DV, S122TTRSA AGGSSWC | Forward | CACTTCCAAAGAATGGWTAACDSKTTCTCCAA CTCCGCT | 174 |
| | Reverse | AGCGGAGTTGGAGAAMSHGTTAWCCATTCTTT GGAAGTG | 175 |
| Library B | | | |
| S166TTRS, A169AG | Forward | GGTACCTTGTACAAGASMGAGTCCGSCTCCTT CACCCCAAAC | 176 |
| | Reverse | GTTTGGGGTGAAGGAGSCGGACTCKSTCTTGT ACAAGGTACC | 177 |
| S191SG, V193EDGGV V, I200TI | Forward | TCCATGCCACAARGCGGTGDMTTGAAGGCTGG TCAAACCAYTCACTACGACGAG | 178 |
| | Reverse | CTCGTCGTAGTGARTGGTTTGACCAGCCTTCA AKHCACCGCYTTGTGGCATGGA | 179 |
| N219NDY, Q222QE, N236KNQHED | Forward | GTDATTCCGGTSAGAGAATCTACTTGCCAGTC AGAACCTGGAACAAGTCCACCVAWAC | 180 |
| | Reverse | GTWTBGGTGGACTTGTTCCAGGTTCTGACTGG CAAGTAGATTCTCTSACCGGAATHAC | 181 |
| Library C | | | |
| Y33NDY, M39RMRLGV, | Forward | GGTGGTATGCACDATGGTGTTGACTTCTTTVK GAACATCGGTAMGCCAGTCAAGGCT | 182 |

TABLE 18-continued

| Mutations | Primer | Sequence (5'->3') | SEQ ID NO: |
|---|---|---|---|
| T43KT | Reverse | AGCCTTGACTGGCKTACCGATGTTCMBAAAGA AGTCAACACCATHGTGCATACCACC | 183 |
| W79TRSW, S84SRG | Forward | GGTGAGCACAGACAAWSGTACATGCACTTGVG TAAGTACAACGTCAAG | 184 |
|  | Reverse | CTTGACGTTGTACTTACBCAAGTGCATGTACS WTTGTCTGTGCTCACC | 185 |
| S191SG, V193DGV | Forward | AGATCCATGCCACAARGCGGTGDCTTGAAGGC TGGTCAA | 186 |
|  | Reverse | TTGACCAGCCTTCAAGHCACCGCYTTGTGGCA TGGATCT | 187 |
| N236KNQHED | Reverse | ATCGGAATTCTTACTTGATGGTACCCCACAAG ACACCCAAGGTWTBGGTGGACTTGTTC | 188 |

Library D

| Mutations | Primer | Sequence (5'->3') | SEQ ID NO: |
|---|---|---|---|
| Y33NY, G34DG, T43KT, V45VL | Forward | GGTATGCACWATGRCGTTGACTTCTTTATGAA CATCGGTAMGCCAKTAAAGGCTATC | 189 |
|  | Reverse | GATAGCCTTTAMTGGCKTACCGATGTTCATAA AGAAGTCAACGYCATWGTGCATACC | 190 |
| Y33NDY, N40KNTT, T43KTR | Forward | GGTATGCACDATGGTGTTGACTTCTTTATGAM WATCGGTAVACCAGTCAAG | 191 |
|  | Reverse | CTTGACTGGTBTACCGATWKTCATAAAGAAGT CAACACCATHGTGCATACC | 192 |
| V35DEVV, T43TKR, V45EDGGVV | Forward | CACTATGGTGWSGACTTCTTTATGAACATCGG TAVACCAGDMAAGGCTATC | 193 |
|  | Reverse | GATAGCCTTKHCTGGTBTACCGATGTTCATAA AGAAGTCSWCACCATAGTG | 194 |
| F116SCF | Forward | CCACACTTGCACTBCCAAAGAATGGAT | 195 |
|  | Reverse | ATCCATTCTTTGGVAGTGCAAGTGTGG | 196 |
| R186TR, S191AS | Forward | GGTCCATTCASGTCCATGCCACAAKCTGGTGT CTTG | 197 |
|  | Reverse | CAAGACACCAGMTTGTGGCATGGACSTGAATG GACC | 198 |
| S191SG, V193DGV | Forward | TCCATGCCACAARGCGGTGDCTTGAAGGCTGGT | 199 |
|  | Reverse | ACCAGCCTTCAAGHCACCGCYTTGTGGCATGGA | 200 |
| R186TTSRP RRAAGGSSC W, V193KKRRI MQQRRLLEE GGVV | Forward | GGTCCATTCNSSTCCATGCCACAAAGCGGTVD RTTGAAGGCT | 201 |
|  | Reverse | AGCCTTCAAYHBACCGCTTTGTGGCATGGASS NGAATGGACC | 202 |

Library E

| Mutations | Primer | Sequence (5'->3') | SEQ ID NO: |
|---|---|---|---|
| N28NS, I41NI, T43KT | Forward | GTATCARCGGTGGTATGCACTATGGCGTTGAC TTCTTTATGACCAWCGGTAMGCCAGT | 203 |
|  | Reverse | ACTGGCKTACCGWTGGTCATAAAGAAGTCAAC GCCATAGTGCATACCACCGYTGATAC | 204 |
| G34DG, I41KNII, T43KT | Forward | CACTATGRCGTTGACTTCTTTATGACCAWMGG TAMGCCAGTA | 205 |
|  | Reverse | TACTGGCKTACCKWTGGTCATAAAGAAGTCAA CGYCATAGTG | 206 |
| G34EDGG, T43KTR, I41KKRRIM EEGGVV | Forward | CACTATGRKGTTGACTTCTTTATGACCRDRGG TAVACCAGTA | 207 |
|  | Reverse | TACTGGTBTACCYHYGGTCATAAAGAAGTCAA CMYCATAGTG | 208 |
| N28NK, G30EG, I41NI, T43KRT | Forward | GTATCAASGGTGRAATGCACTATGGCGTTGAC TTCTTTATGACCAWCGGTAVACCAGT | 209 |
|  | Reverse | ACTGGTBTACCGWTGGTCATAAAGAAGTCAAC GCCATAGTGCATTYCACCSTTGATAC | 210 |
| N121NK, S124SSCW | Forward | AGAATGGATAASACTTTCTSSAACTCCGCT | 211 |
|  | Reverse | AGCGGAGTTSSAGAAAGTSTTATCCATTCT | 212 |

TABLE 18-continued

| Mutations | Primer | Sequence (5'->3') | SEQ ID NO: |
|---|---|---|---|
| T122TTIM, S124SSCW | Forward | AGAATGGATAACAYRTTCTSSAACTCCGCTGCT | 213 |
| | Reverse | AGCAGCGGAGTTSSAGAAYRTGTTATCCATTCT | 214 |

The PCR products were ligated into pPIC9 vector and transformed into DH5a. Constructs were sequence verified and transformed into *P. pastoris* by electroporation (Wu & Letchworth (2004) *Biotechniques* 36:152-4). Library construction and screening was implemented as an iterative directed evolution strategy. Active library members were identified using a moderate throughput plate halo formation assay. Briefly, *P. pastoris* transformants from each round of library construction were spread on YPM agar media (1% yeast extract, 2% peptone, 1% methanol, 1% agarose) and incubated at 30° C. for 2 days. Indicating top agarose (0.5% yeast extract, 1% peptone, 1% NaCl, 0.1 $OD_{600}$ SA113, 1% low melting agarose) was poured onto the YPM yeast plates, and the plates were incubated at 37° C. for 10 hours. Yeast clones expressing active enzymes were identified by their characteristic halo or zone of clearance. Approximately 10,000 clones were screened for each round. The genes encoding the 10 variants exhibiting the largest halos were PCR amplified from the genomically integrated cassette, subcloned back into pPIC9, sequenced, and retransformed into freshly prepared *P. pastoris* cells for functional validation by determination of MIC. The most deimmunized and functional variant was used as the starting point for the subsequent round of library construction and screening.

In Vivo Studies. The protocols for animal infection, treatment, and immunization were carried out to minimize animal suffering. C57Bl/6 mice were purchased from the Jackson Laboratory (Bar Harbor, Me.). C57Bl/6 background Abb Knockout/Transgenic HLA-DR4 mice (B6.129S2-H2-Ab1$^{tm1Gru}$ Tg(HLA-DRA/H2-Ea, HLA-DRB1*0401/H2-Eb)1Kito) were purchased from Taconic Farms (Germantown, N.Y.).

In Vivo Immunogenicity. A 100 μl volume of 100 μg purified wild-type or variant enzyme in complete Freund's adjuvant (CFA) was injected subcutaneously in either DR4 (N=5 per group) or C57Bl/6 (N=4 per group) mice. Thirteen days following immunization, serum was collected and anti-LST IgG antibody titers (specific to wild-type or variant protein) were measured by ELISA. Briefly, wild-type or variant protein antigen was coated onto high binding ELISA plates, followed by blocking with BSA. Immune serum from mice was serially diluted into the coated plates, which were then probed using goat anti-mouse IgG-HRP conjugate (Santa Cruz Biotechnology, Dallas, Tex.) at a working concentration of 1:1000. Plates were subsequently developed using TMB Substrate (Santa Cruz Biotechnology) Reported titers were defined as the serum fold dilution yielding an absorbance of 1.5.

In Vivo Efficacy. Prior to bacterial challenge, the immune systems of DR4 mice (N=3 per group) were primed 3-times with weekly subcutaneous injections of 100 μg $LST^{WT}$ or Lib5 variant in sterile phosphate buffered saline (PBS: 2.7 mM KCl, 1.5 mM $KH_2PO_4$, 8.9 mM $Na_2HPO_4$, 136.9 mM NaCl, pH 7.4). These immunizations and boosts contained no adjuvant. Anti-LST antibody titers were determined as described above. For the first cycle of infection and treatment, mice were challenged with intraperitoneal administration of $2\times10^8$ CFU *Staphylococcus aureus* strain USA400 in a 3% suspension of porcine mucin, and one hour later were treated by intravenous tail vein administration of 500 μg of $LST^{WT}$ or Lib5 variant in sterile PBS. Mice that were rescued by the enzyme treatment underwent subsequent infection and treatment cycles at weekly intervals. To compensate for development of innate murine antibacterial immunity following the first bacterial exposure, mice were challenged with $1\times10^9$ CFU USA400 in the second and third cycles, but the treatments remained at 500 μg of the appropriate protein. As a control to verify the lethal bacterial dose in each cycle, one mouse was given a sham treatment of PBS.

Structure-Based Design of Individual Variants

The EpiSweep algorithm (Parker, et al. (2013) *J. Comput. Biol.* 20:152-65) was used to optimize deimmunized variants, making the best trade-offs between predicted reduction in epitope content, as evaluated by ProPred, and predicted maintenance of protein stability, as evaluated by structure-based rotamer energy. Panels of 20 fully depleted designs (i.e., DR4 epitope scores=0) were generated separately for both the catalytic and cell wall binding domains. A variant combining low energy designs from each domain, Opt1 (Table 19), was selected for experimental analysis and cloned into an optimized *Pichia pastoris* expression system. Unfortunately, this 14-mutation design failed to yield functional protein (Table 20).

TABLE 19

| | Residues in the catalytic domain | | | | | | | | | |
|---|---|---|---|---|---|---|---|---|---|---|
| Design | Y33 | F38 | N40 | I70 | N72 | V75 | S84 | M119 | V120 | N121 | S122 |
| $LST^{WT}$ | | | | | | | | | | | |
| Opt1 | T | S | | | H | Q | Y | R | | G | G |
| Opt2 | T | S | | | H | Q | Y | | | G | G |
| Opt3 | T | S | | | H | Q | Y | | | G | G |
| Opt4 | T | S | | | H | Q | Y | | | G | G |
| Lib1 | | | | K | E | | | | D | | T |
| Lib2 | | | | | | | | | | | |
| Lib3 | | | | K | E | | | | D | | T |
| Lib4 | | | | K | E | G | | | D | | T |
| Lib5 | | | T | K | E | G | | | D | | T |

TABLE 19-continued

| | Residues in the cell wall binding domain | | | | | | | | | |
|---|---|---|---|---|---|---|---|---|---|---|
| Design | S166 | S168 | A169 | R186 | S191 | V193 | I200 | N219 | S234 | N236 |
| LST$^{WT}$ | | | | | | | | | | |
| Opt1 | E | K | | | | W | T | Y | | D |
| Opt2 | E | K | | | | W | T | Y | | D |
| Opt3 | | | | | | | T | Y | | D |
| Opt4 | | | | | | | T | Y | K | |
| Lib1 | | | | | | | | | | |
| Lib2 | T | | G | | | | T | Y | | |
| Lib3 | T | | G | | | | T | Y | | |
| Lib4 | T | | G | | | | T | Y | | D |
| Lib5 | T | | G | T | A | | T | Y | | D |

TABLE 20

| Design | Mutation Load | Epitope Score | Expression Level (% WT) | Activity (% WT) |
|---|---|---|---|---|
| LST$^{WT}$ | 0 | 16 | 100 | 100 |
| Opt1 | 14 | 0 | ND$^b$ | ND$^b$ |
| Opt2 | 13 | 1 | ND$^b$ | ND$^b$ |
| Opt3 | 10 | 5 | 20 | ND$^a$ |
| Opt4 | 10 | 5 | 10 | 0.25 |
| Lib1 | 4 | 13 | 80 | 100 |
| Lib2 | 4 | 12 | 80 | 100 |
| Lib3 | 8 | 8 | 60 | 50 |
| Lib4 | 10 | 6 | 50 | 50 |
| Lib5 | 13 | 3 | 50 | 50 |

$^a$Activity measured as minimal inhibitory concentration (MIC), reported as the % fold dilution, relative to wild type, at which the MIC was achieved.
$^b$Not Detectable.

The LST redesign work in Example 1 shows that single mutations could undermine otherwise stable and active deimmunized variants. Therefore, detrimental mutations in the Opt1 design were identified by systematically reverting mutations and mutation combinations. Analysis of isolated Opt1 mutations revealed that Met119Arg single-handedly abolished protein secretion, but reversion of this single mutation in design Opt2 (Table 19) failed to restore expression (Table 20). Ultimately, it was found that the three mutation combination Ser166Glu, Ser168Lys, and Val193Trp also undermined expression, and reversion to wild-type at these three sites as well as Met119 generated an expressible 10-mutation variant, Opt3 (Table 20).

Although Opt3 achieved reasonable expression levels (Table 20), purity analysis by SDS-PAGE revealed two bands: one at the expected 25 kDa mass and a second at approximately 30 kDa. Based on the results in Example 1, it was suspected that a latent N-linked glycosylation sequon in the C-terminal cell wall binding domain ($^{232}$NKS$^{234}$) had been activated. Therefore, the deimmunizing Asn236Asp mutation was exchanged with the Ser234Lys mutation, which deleted both the C-terminal epitope and the N-linked glycosylation sequon. The resulting 10-mutation variant, Opt4, bore only five predicted DR4 epitopes and expressed as a single 25 kDa band, albeit with lower yields than Opt3 (Table 20). Although the highly engineered Opt4 variant was produced in a folded and secretion competent state, it was subsequently found to possess only a small fraction of the wild type enzyme's antibacterial activity (Table 20).

Structure-Based Deimmunization Via Computational Library Design

In parallel to design of individual variants, an alternative combinatorial approach was pursued in which computational design was used to generate LST libraries predicted to be enriched in functional, deimmunized variants. The structure-based library design method SOCoM was augmented with epitope analysis in order to identify residue positions and mutations whose combinations yielded variants with low epitope scores, as evaluated by ProPred, along with good energies, as evaluated by a Cluster Expansion potential trained on Rosetta models. In the initial round, the designs were based on the wild-type reference, while in succeeding rounds the reference was shifted to the lead clone selected from the previous library screen.

Library A targeted nine sites in the catalytic domain, and the complementary Library B population targeted eight sites in the cell wall binding domain (Table 18). Although the deimmunized LST design space was massive, the initial libraries were constrained to fewer than 40,000 members so as to maintain some parity between library size and the screening capacity of agar plate halo formation assays. Approximately 10,000 clones were screened from both Libraries A and B, and 10 large-halo-forming colonies from each were sequenced and functionally validated. The most promising variant from Library A (clone Lib1) contained four mutations in the catalytic domain and exerted antibacterial activity equivalent to LST$^{WT}$ (Tables 19 and 20). Likewise, the most promising variant from Library B (clone Lib2) possessed four mutations in the cell wall binding domain (Table 19) and also had wild-type antibacterial activity (Table 20).

The respective deimmunized domains of variants Lib1 and Lib2 were combined to produce variant Lib3, containing eight mutations (Table 19), a 50% reduction in predicted epitope content, and retention of 50% wild-type activity (Table 20). The structures of the two Lib3 domains were subsequently modeled and used as templates in another round of deimmunized library design. The resulting Library C targeted five sites in the catalytic domain and three sites in the cell wall binding domain (Table 19). Functional screening of 10,000 clones yielded variant Lib4, which deleted 10/16 DR4 epitopes. Relative to its Lib3 starting template, Lib4 contained one additional mutation each in the catalytic and cell wall binding domains and retained equivalent antibacterial activity (Table 20). The domains of Lib4 were used in another iterative round of modeling and deimmunized library design, yielding Library D, from which 10,000 clones were screened to isolate variant Lib5. Variant Lib5 deleted 13/16 putative DR4 epitopes (Table 19), yet retained 50% wild-type expression and 50% antibacterial activity (Table 20). Compared to variant Opt4, the best enzyme from the individual protein design efforts, Lib5 exhibited both a lower predicted epitope score and higher measured functionality.

Further library construction and screening efforts (Library E) failed to identify additional functional constructs. Therefore, the 13-mutation Lib5 variant was designated the lead candidate for further analysis. It is interesting to note that the three putative epitopes remaining in variant Lib5 ($^{33}$YGVD-FFMTI$^{41}$, SEQ ID NO:215; $^{38}$FMTIGTPVK$^{46}$, SEQ ID NO:216; and $^{116}$FQRMDNTFS$^{124}$, SEQ ID NO:217) either encompass or are adjacent to amino acids responsible for active site $Zn^{2+}$ coordination (His32, Asp36 and His115). This fact may explain the elusive nature of functional mutations within these regions; screening of diverse library populations identified only one functional substitution in region 33-46 and two in region 116-124 (Table 19).

Epitope Depleted Designs Display Significantly Reduced Immunogenicity in vivo

The extent to which epitope depletion impacted in vivo immunogenicity was subsequently assessed. Anti-LST antibody responses were determined in both C57Bl/6 and transgenic DR4 mice, the latter of which are null for endogenous murine MHC II, but bear a chimeric MHC II receptor derived from human HLA DRB1*0401 (Ito, et al. (1996) *J. Exp. Med.* 183:2635-44). As a stringent benchmark for deimmunization, mice were immunized subcutaneously with protein in complete Freund's adjuvant, a powerful immunostimulant. Two weeks after a single immunization with LST$^{WT}$, all DR4 mice mounted a potent anti-LST IgG antibody response, with titers between 1:150 and 1:1700. In contrast, mice immunized with Opt4 showed a striking reduction in titers; only 2/5 mice exhibited any detectable anti-LST antibodies, and even those were substantially reduced relative to LST$^{WT}$ immunized animals. Variant Lib5 also elicited a reduced antibody response; only one animal exhibited high antibody titers (1:1200), three showed significantly lower antibody titers (1:15 to 1:26), and 1 mouse exhibited near background levels of anti-LST antibodies. Importantly, both LST$^{WT}$ and Opt4 were equally immunogenic in the C57Bl/6 laboratory mouse strain, while Lib5 was actually more immunogenic than LST$^{WT}$ (IgG titers 1:4400 to 1:15,000 versus 1:560 to 1:2100, respectively). Thus, the striking reductions in Opt4 and Lib5 immunogenicity were specifically associated with disruption of molecular recognition by human DR4, as opposed to the native murine MHC II.

It was of note that although the protein design process was blinded to all but allele DR4, ProPred predictions indicated that neither Opt4 nor Lib5 contained neoepitopes for seven other representative human DRB1 alleles (Supp. FIG. S1). In fact, over and above the 11 putative DR4 epitopes deleted from Opt4, predictions suggested that 12 epitopes associated with alleles DR1, DR3, DR7, DR13, and DR15 had also been deleted. Similarly for Lib5, in addition to deletion of 13 DR4-restricted epitopes, ProPred predicted deletion of 18 additional epitopes associated with the other seven DRB1 alleles.

Lysostaphin Deimmunization Translates into Improved Therapeutic Efficacy

In some embodiments, therapeutic application of LST may require repeated administration to fully eradicate *S. aureus* infections. Therefore, to more closely mimic potential clinical applications, the immunogenicity of LST$^{WT}$ and Lib5 were monitored during weekly dosing in the absence of adjuvant. Seven days after a third immunization, all DR4 mice receiving LST$^{WT}$ had mounted a relatively strong immune response, with anti-LST titers in the 1:40 to 1:160 range. During the same time-frame, only one of three mice immunized with Lib5 developed high antibody titers (1:120), where the other two Lib5 mice exhibited titers only marginally above background.

Using an *S. aureus* recurrent bacteremia model, the extent to which LST immunogenicity impacted in vivo efficacy was subsequently evaluated. Following determination of antibody titers at week three, the above DR4 mice were infected by intraperitoneal administration of $2\times10^8$ colony forming units (CFU) of methicillin-resistant *S. aureus* (MRSA) strain USA400. One hour later, mice were given a 500 µg intravenous bolus of LST$^{WT}$ or Lib5, respectively. Both enzymes rescued their respective groups from this initial infection, whereas a control mouse given a PBS sham treatment had to be sacrificed due to excessive morbidity.

One week later, antibody titers had increased for both the LST$^{WT}$ group (1:300 to 1:650) and the Lib5 group (1 mouse>1:1000, with the remaining two between 1:15 and 1:20), but the latter continued to exhibit a lower overall trend. Mice were now infected with $10^9$ CFU of MRSA and again treated 1 hour later with a 500 µg intravenous bolus of the respective enzyme. In this second infection cycle, where mice had developed higher antibody titers, LST$^{WT}$ failed to rescue any of the three treated mice. Similarly, the single Lib5 mouse exhibiting high antibody titers succumbed to the infection, but the two lower titer Lib5 mice were rescued from the second MRSA challenge.

The following week, antibody titers in the two surviving Lib5 mice were found to have increased yet again (1:70 and 1:120), but notably they remained below the week four LST$^{WT}$ titers. Following a third infection cycle with MRSA, one mouse was treated with Lib5 and survived, whereas the second mouse was given a PBS sham and succumbed to the infection. As a whole, these results showed that humanized DR4 mice mounted a strong immune response to LST$^{WT}$, even in the absence of adjuvant. During repeated administration, the weekly increase in anti-LST$^{WT}$ antibody titers correlated with loss of efficacy. Conversely, immune responses were attenuated in two of three mice receiving the Lib5 deimmunized variant, and once again in vivo efficacy tracked with anti-LST antibody titers. Lib5 exerted potent antibacterial efficacy against as many as three consecutive challenges with MRSA.

Throughout the study, anti-LST antibody titers below 1:256 correlated with enzyme-mediated rescue from *S. aureus* infection, whereas titers above 256 were universally associated with failure of the antibacterial enzyme therapy. Variant Lib5's capacity to mitigate anti-drug antibody responses therefore manifested as enhanced efficacy relative to LST$^{WT}$.

EXAMPLE 3

Figure 6A:
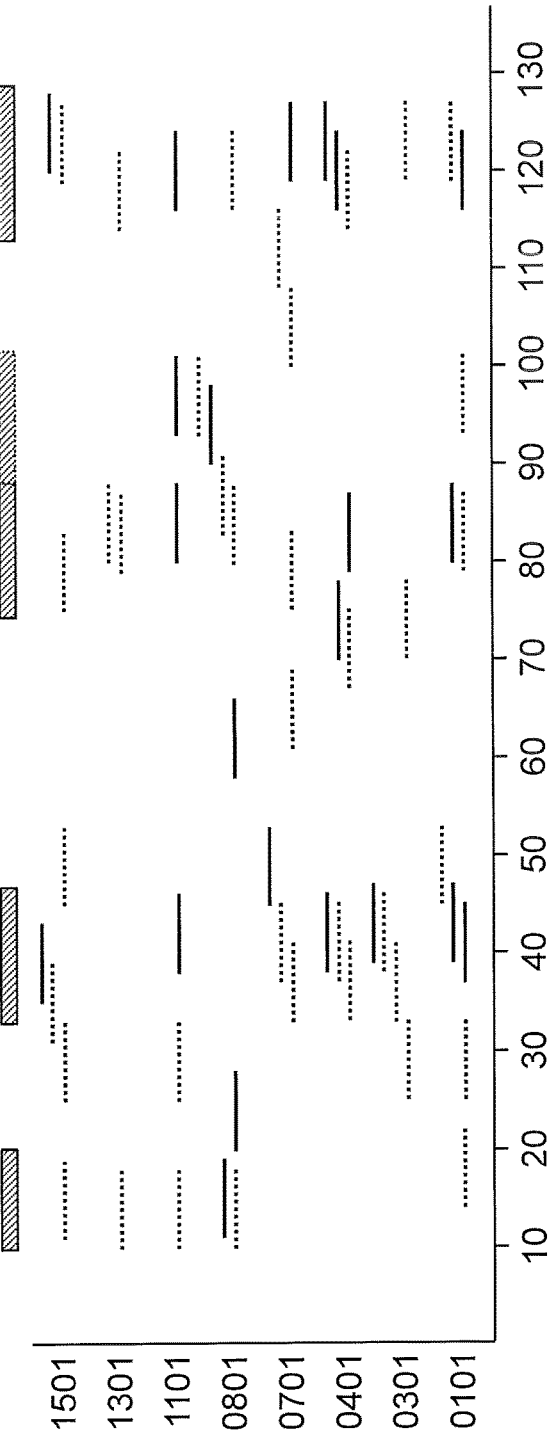
FIGS. 6A and 6B show the global epitope map of the lysostaphin catalytic and cell wall binding domain, respectively. Epitopes were predicted for HLA alleles DRB1*0101, 0301, 0401, 0701, 0801, 1101, 1301, and 1501. Nine residue peptide epitopes are indicated by solid lines (1-2% threshold) and dashed lines (3-5% threshold). The Lysostaphin catalytic domain primary sequence is indicated on the x-axis, and the HLA alleles associated with each peptide epitope are shown on the y-axis. Higher risk regions for designability analysis are marked at top with filled boxes. The box with the broken line represents a moderate risk region that was also redesigned during development of the deimmunized Flex 9 deimmunized catalytic domain.
Figure 6B:
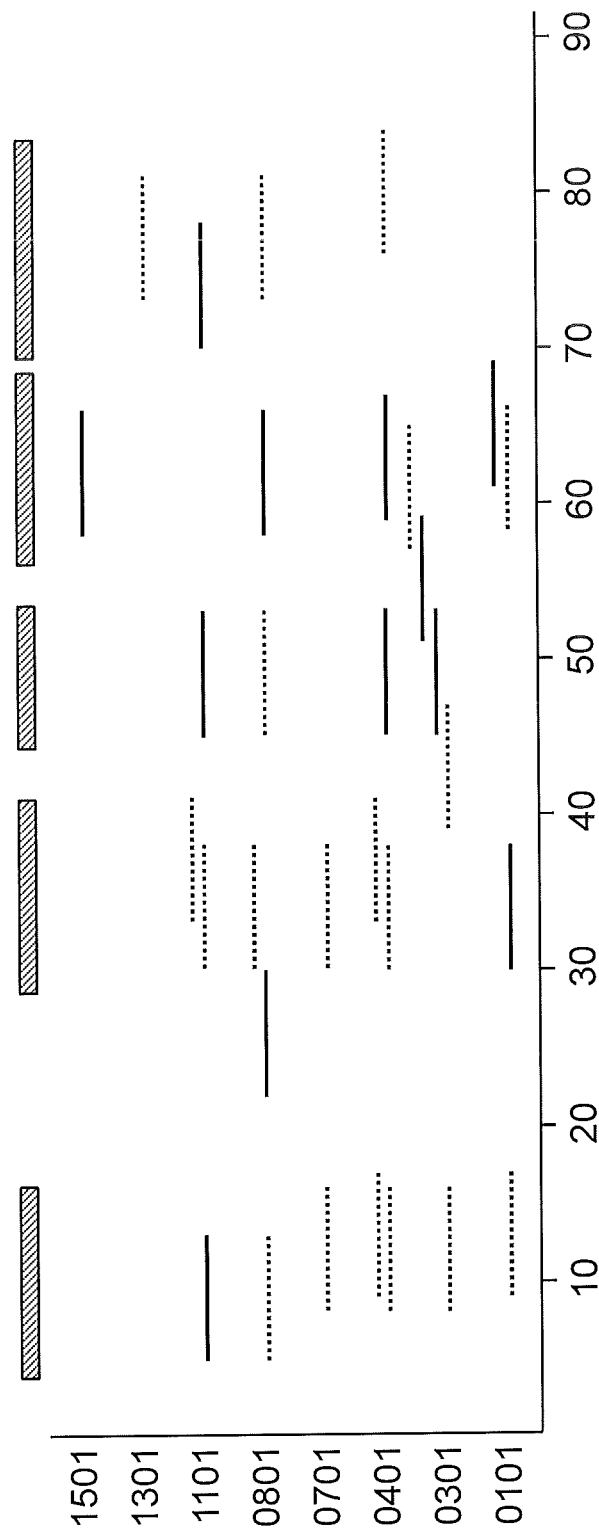

Deimmunization of Lysostaphin Catalytic and Cell Wall Binding Domains Against HLA Alleles Representative of the HLA Binding Specificity in Human Populations To deimmunize LST against human HLA alleles DRB1*0101, 0301, 0401, 0701, 0801, 1101, 1301, and 1501, individual variants and libraries predicted to be enriched in functional, deimmunized variants were generated. Epitope mapping of the catalytic domain (FIG. 6A) and cell wall binding domain (FIG. 6B) was carried out as described in Example 2. Using this information, as well as solvent accessibility and evolutionary conservation, deimmunized LST mutants were generated.

In particular, mutations in the cell wall binding domain (Table 21) were combined with mutations in the catalytic domain of the Flex 9 mutant (Example 1) or a Flex 9 derivative.

TABLE 21

| Residue Position | Wild-type | Single Designs 1 | Single Designs 2 | Library Designs 1 | Library Designs 2 |
|---|---|---|---|---|---|
| 160 | Y | | | N, H, D, Y | |
| 164 | Y | W | | | |
| 166 | S | E | E | | K, N, T, R, S, E, D, A, G |
| 168 | S | K | | | |
| 169 | A | | | E, D, A, G | |
| 186 | R | | | T, R | |
| 193 | V | W | D | E, D, G, V | D, G, V |
| 195 | K | H | H | | |
| 200 | I | T | T | T, I | T, R, I |
| 209 | D | | | | E, D, A, G |
| 214 | V | | | I, M, V, L | |
| 215 | G | | | | E, G |
| 218 | G | | | D, G | D, G |
| 224 | I | | | K, R, I | K, R, I |
| 229 | R | | | R, G | R, G |
| 232 | N | Q | Q | | |
| 236 | N | D | | | N, D |
| 237 | T | K | | | |

Variants were screened and three variants of interest were identified, F11, F12 and F13 (Table 22).

TABLE 22

| Variant | Mutations# | SEQ ID NO: |
|---|---|---|
| F11 | N12G, I41E, L83M, K95E, I99Q, N121G, S122D, S124G, S126P*, Y160H, A169G, R186T, N232Q* | 218 |
| F12 | N12G, I41E, L83M, I99Q, N121G, S122D, S124G, S126P*, Y160H, S166N, A169G, R186T, N232Q*, N236D | 219 |
| F13 | N12G, I41E, L83M, K95E, I99Q, N121G, S122D, S124G, S126P*, Y160H, S166N, A169G, R186T, N232Q*, N236D | 220 |

*aglycosylation mutations for efficient production in eukaryotic host cells. These mutations are not required for expression in bacterial hosts.
Relative to wild-type lysostaphin sequence (SEQ ID NO: 49).

Figure 7:
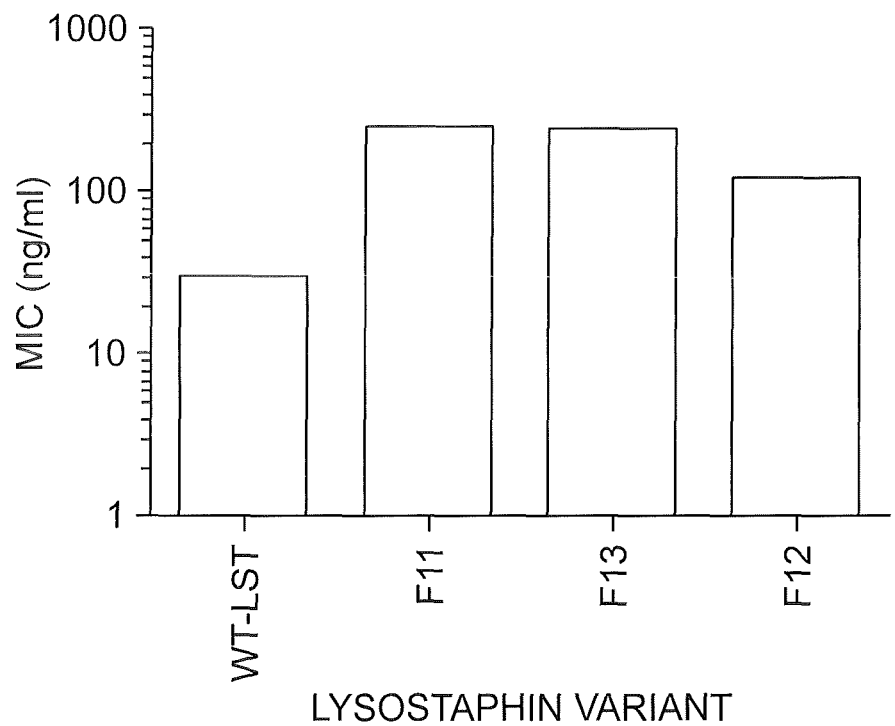
FIG. 7 shows the minimum inhibitory concentration (MIC) for F11, F12 and F13 against MRSA strain USA400.

F11, F12 and F13 were screened for in vitro inhibitory activity against MRSA strain USA400 (FIG. 7). This analysis indicated that variants F11 and F13 retained 12.5% MIC activity relative to wild-type LST, while variant F12 retained 25% MIC activity relative to wild-type LST. Further, upon heating the variants at 50° C. for 1 hour prior to determining activity against MRSA strain USA400, it was found that wild-type LST retained full MIC activity, F13 retained 25% of its original MIC activity, and F12 retained 50% of its original MIC activity.

Figure 8:
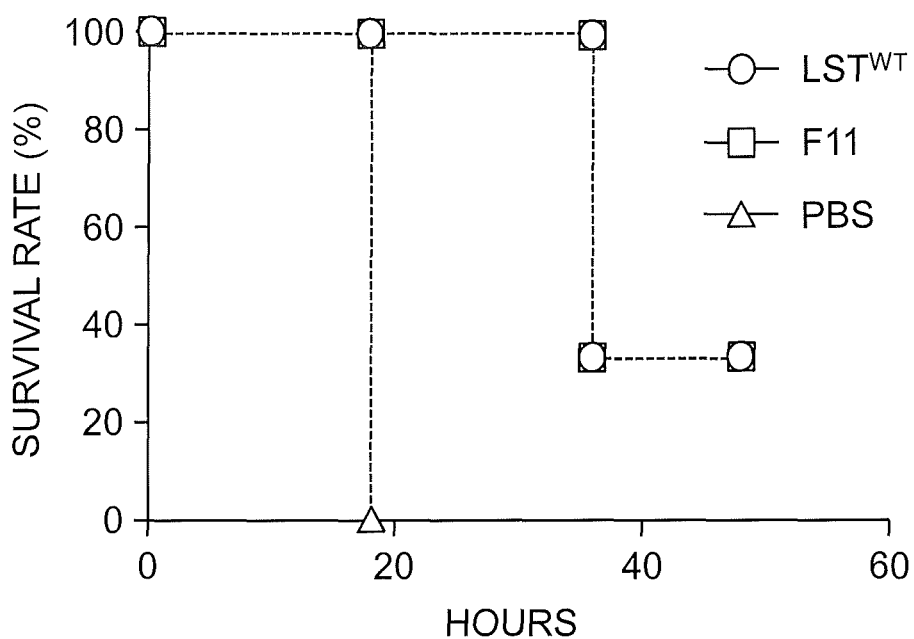
FIG. 8 shows the in vivo efficacy of the F11 variant in C57BL/6 mice. Mice were challenged with an intraperitoneal injection of $2\times10^8$ MRSA strain USA400, and 1 hour later the mice were treated with 100 μg wild-type LST, F11 or PBS. The percent survival is shown.

The in vivo efficacy of the F11 variant was further analyzed in C57BL/6 mice. Mice were challenged with an intraperitoneal injection of $2 \times 10^8$ MRSA strain USA400, and 1 hour later the mice were treated with 100 µg wild-type LST, F11 or PBS, administered as a single bolus intravenous injection. The survival rate for both protein treatments was 1/3. The 100 µg dosage was selected because wild-type LST is known to be only partially efficacious at this dose. By using this dose, clear efficacy equivalence for the F11 variant could be demonstrated. This analysis indicated that both proteins had equivalent efficacy in vivo (FIG. 8).

The immunogenicity of the F13 variant was compared to wild-type LST in DR4 HLA transgenic mice, i.e., mice bearing partially humanized immune systems. 100 µg of wild-type LST or variant F13 were mixed with complete Freund's adjuvant and injected subcutaneously into DR4 mice. Fourteen days later, antibody titers were measured by ELISA. Variant F13 yielded more than 200-fold lower antibody titers compared to wild-type LST. To assess the impact of antibody titers on antibacterial efficacy, the mice were challenged with an intraperitoneal injection of $2 \times 10^8$ MRSA strain USA400, and 1 hour later the mice were treated with 500 µg wild-type LST, variant F13, or PBS, administered as a single bolus intravenous injection. Both mice receiving PBS sham treatments died as did both mice treated with wild-type LST. In contrast, both mice treated with variant F13 survived. Thus, the reduced immunogenicity of F13 conferred enhanced therapeutic efficacy in vivo.

In a similar set of experiments, the immunogenicity and efficacy of variant F12 was compared to wild-type LST in the absence of adjuvant using DR4 HLA transgenic mice. At week 0, mice were challenged with an intraperitoneal injection of $2 \times 10^8$ MRSA strain USA400, and 1 hour later the mice were treated with 500 µg wild-type LST or 500 µg variant F12, given as a single bolus subcutaneous injection. Subsequently, mice were challenged weekly with an intraperitoneal injection of $1 \times 10^9$ MRSA strain USA400, and treated as above. Antibody titers were measured weekly beginning at week 2. Wild-type LST was able to rescue mice from a total of four recurrent, systemic, MRSA infections, but failed to rescue any mice from the fifth infection (Table 23). Variant F12 rescued all mice from four recurrent, systemic, MRSA infections (Table 24). The substantially lower antibody titers elicited by variant F12 indicate that this variant is more efficacious than wild-type LST.

TABLE 23

| Week | # Mice Infected | # Mice Treated with Enzyme | # Treated Mice Surviving | # Mice Treated with PBS | # Sham Treatment Surviving |
|---|---|---|---|---|---|
| 0 | 7 | 7 | 7 | 0 | NA |
| 1 | 7 | 6 | 6 | 1 | 0 |
| 2 | 6 | 5 | 5 | 1 | 0 |
| 3 | 5* | 4 | 4 | 1 | 0 |
| 4 | 4 | 3 | 0 | 1 | 0 |

*ELISA antibody titers measured for only four representative mice out of five total.

TABLE 24

| Week | # Mice Infected | # Mice Treated with Enzyme | # Treated Mice Surviving | # Mice Treated with PBS | # Sham Treatment Surviving |
|---|---|---|---|---|---|
| 0 | 10 | 10 | 10 | 0 | NA |
| 1 | 10 | 9 | 9 | 1 | 0 |
| 2 | 9* | 8 | 8 | 1 | 0 |
| 3 | 8 | 7 | 7 | 1 | 0 |
| 4 | 7 | 6 | 6 | 1 | 0 |
| 5 | pending | pending | pending | pending | pending |

*ELISA antibody titers measured for only eight of nine total.

What is claimed is:

1. A de-immunized lysostaphin or fragment thereof, comprising a mutation at one or more of Thr127, Ser126, Ser124, Ser122, Asn121, Val120, Met119, Arg118, Ile99, Lys95, Tyr93, Ser84, Leu83, Val75, Asn72, Ile70, Lys46, Ile41, Asn40, Phe38, Tyr33, Asn13, or Asn12 of SEQ ID NO: 49, wherein the fragment comprises a catalytically active domain of a lysostaphin,
  wherein the de-immunized lysostaphin or fragment thereof is at least 90% identical to the catalytically active domain of a lysostaphin of SEQ ID NO: 49.

2. The deimmunized lysostaphin of claim 1, wherein said lysostaphin is aglycosylated.

3. The deimmunized lysostaphin of claim 1, wherein the mutation comprises Thr127Ala; Ser126Pro; Ser124Gly; Ser122Asp, Ser122Gly, or Ser122Thr; Asn121Gly; Val120Asp; Met119Arg; Arg118Thr; Ile99Gln; Lys95Glu; Tyr93His; Ser84Tyr or Ser84Gly; Leu83Met; Val75Glu or Val75Gln; Asn72His; Ile70Lys; Lys46His; Ile41Gln; Asn40Thr; Phe38Ser; Tyr33Thr; Asn13His; Asn12Gly; or a combination thereof.

4. The deimmunized lysostaphin of claim 1, further comprising one or more amino acid substitutions in the C-terminal cell wall binding domain.

5. A pharmaceutical composition comprising the deimmunized lysostaphin of claim 1 and a pharmaceutically acceptable carrier.

6. The pharmaceutical composition of claim 5, further comprising an antibiotic.

7. The pharmaceutical composition of claim 6, wherein said antibiotic comprises a β-lactam, cephalosporin, aminoglycoside, sulfonamide, antifolate, macrolide, quinolone, glycopeptide, polypeptide or a combination thereof.

8. A method for preventing or treating a microbial infection comprising administering to a subject in need of treatment the pharmaceutical composition of claim 5, thereby preventing or treating the subject's microbial infection.

9. The method of claim 8, wherein said infection is a bacterial infection.

10. The method of claim 9, wherein said bacterial infection is caused by bacteria from the genus Staphylococcus.

11. The aglycosylated lysostaphin of claim 2, comprising a mutation at Ser126, Thr127, and/or Ser234.

12. The aglycosylated lysostaphin of claim 2, comprising the mutation Ser126Pro, Thr127Ala, and/or Ser234Lys.

13. The deimmunized lysostaphin of claim 4, comprising a mutation at one or more of Asn236, Ser234, Asn232, Asn219, Ile200, Val193, Ser191, Arg186, Ala169, Ser168, Ser166, or Tyr160.

14. The deimmunized lysostaphin of claim 4, wherein the mutation comprises Asn236Asp, Ser234Lys, Asn232Gln, Asn219Tyr, Ile200Thr, Val193Trp, Ser191Ala Arg186Thr, Ala169Gly, Ser168Lys Ser166Asn or Ser166Thr, Tyr160His, or a combination thereof.

15. A deimmunized lysostaphin or fragment thereof, comprising the sequence represented by SEQ ID NO: 218-220.

16. A method for preventing or treating a biofilm comprising administering to a subject in need of treatment the pharmaceutical composition of claim 5.

17. A vector encoding the deimmunized lysostaphin of claim 1.

18. A pharmaceutical composition comprising the deimmunized lysostaphin of claim 17 and a pharmaceutically acceptable carrier.

19. The method of claim 8, wherein the pharmaceutical composition is administered by a route selected from the group consisting of topical, ophthalmic, intranasal, intravenous, intramuscular, subcutaneous, intraperitoneal, intrathecal, and inhalation delivery.

20. The method of claim 8, wherein the pharmaceutical composition is provided on a medical device.

21. The pharmaceutical composition of claim 6, wherein said antibiotic comprises an inhibitor of cell wall synthesis or protein synthesis.

22. A deimmunized lysostaphin or fragment thereof, comprising a mutation at one or more of Asn236, Asn232, Arg186, Ala169, Ser166, Tyr160, Ser126, Ser124, Ser122, Asn121, Ile99, Lys95, Leu83, Ile41, or Asn12 of SEQ ID NO:49, wherein the fragment comprises a catalytically active domain of a lysostaphin or a cell wall binding domain of a lysostaphin.

23. A de-immunized lysostaphin or fragment thereof where the lysostaphin or fragment thereof comprises a cell wall binding domain of lysostaphin where said cell wall binding domain comprises a mutation at one or more of Asn236, Ser234, Asn232, Asn219, Ile200, Val193, Ser191, Arg186, Ala169, Ser168, Ser166, orTyr160.

24. The deimmunized lysostaphin fragment of claim 22, wherein the lysostaphin fragment comprises a catalytically active domain of a lysostaphin.

25. The deimmunized lysostaphin fragment of claim 22, wherein the lysostaphin fragment comprises a cell wall binding domain of a lysostaphin.

26. A deimmunized lysostaphin or fragment thereof, comprising a mutation at
a) Asn232, Arg186, Ala169, Tyr160, Ser126, Ser124, Ser122, Asn121, Ile99, Lys95, Leu83, Ile41, and Asn12 of SEQ ID NO:49;
b) Asn236, Asn232, Arg186, Ala169, Ser166, Tyr160, Ser126, Ser124, Ser122, Asn121, Ile99, Leu83, Ile41, and Asn12 of SEQ ID NO:49;
c) Asn236, Asn232, Arg186, Ala169, Ser166, Tyr160, Ser126, Ser124, Ser122, Asn121, Ile99, Lys95, Leu83, Ile41, and Asn12 of SEQ ID NO:49;
d) Ser234, Asn219, Ile200, Ser122, Asn121, Ser84, Val75, Asn72, Phe38, and Tyr33 of SEQ ID NO:49;
e) Ser122, Val120, Val75, and Ile70 of SEQ ID NO:49;
f) Asn219, Ile200, Ala169, and Ser166 of SEQ ID NO:49;
g) Asn219, Ile200, Ala169, Ser166, Ser122, Val120, Val75, and Ile70 of SEQ ID NO:49;
h) Asn236, Asn219, Ile200, Ala169, Ser166, Ser122, Val120, Ser84, Val75, and Ile70 of SEQ ID NO:49;
i) Asn236, Asn219, Ile200, Ser191, Arg186, Ala169, Ser166, Ser122, Val120, Ser84, Val75, Ile70, and Asn40 of SEQ ID NO:49;
j) Ser122, Ile99, and Ile41 of SEQ ID NO:49;
k) Ser124, Ser122, Lys46, and Ile41 of SEQ ID NO:49;
l) Ser122, Ile99, Lys95, and Ile41 of SEQ ID NO:49;
m) Ser122, Ile99, Lys95, Tyr93, and Ile41 of SEQ ID NO:49;
n) Ser122, Asn121, Ile99, and Lys46 of SEQ ID NO:49;
o) Ser122, Asn121, Ile99, Ile41, and Asn12 of SEQ ID NO:49;
p) Ser124, Ser122, Ile99, Lys95, Ile41, and Asn12 of SEQ ID NO:49;
q) Ser122, Asn121, Ile99, Leu83, Ile41, and Asn12 of SEQ ID NO:49;
r) Ser124, Ser122, Asn121, Ile99, Lys95, Leu83, Ile41, and Asn12 of SEQ ID NO:49;
s) Ser122, Asn121, Ile41, and Asn12 of SEQ ID NO:49;
t) Ser124, Ser122, Asn121, Ile99, Lys95, Tyr93, Ile41, and Asn12 of SEQ ID NO:49;
u) Ser122, Asn121, Ile99, Lys95, Ile41, and Asn13 of SEQ ID NO:49;
v) Ser122, Asn121, Ile99, Lys95, Tyr93, Ile41, and Asn13 of SEQ ID NO:49;
w) Ser122, and Ile41 of SEQ ID NO:49;
x) Ser122, and Lys46 of SEQ ID NO:49;
y) Ser122, Lys95, Tyr93, and Lys46 of SEQ ID NO:49;
z) Ser122, Lys95, Tyr93, Leu83, Lys46, Ile41, and Asn12 of SEQ ID NO:49;
aa) Ser124, Ser122, Ile99, Lys95, Leu83, Ile41, and Asn12 of SEQ ID NO:49;
bb) Ser122, Lys95, Leu83, Ile41, and Asn12 of SEQ ID NO:49;
cc) Ser122, Leu83, Ile41, and Asn12 of SEQ ID NO:49;
dd) Ser122, Lys95, Tyr93, Leu83, Ile41, and Asn12 of SEQ ID NO:49;
ee) Ser122, Ile41, and Asn12 of SEQ ID NO:49;
ff) Ser122, Lys95, Tyr93, Ile41, and Asn12 of SEQ ID NO:49;
gg) Ser122, Leu83, Lys46, and Asn13 of SEQ ID NO:49;
hh) Ser122, Lys95, Tyr93, Leu83, Lys46, and Asn13 of SEQ ID NO:49;
ii) Ser122, Lys46, and Asn13 of SEQ ID NO:49; or
jj) Ser122, Lys95, Tyr93, Lys46, and Asn13 of SEQ ID NO:49;
wherein the fragment comprises a catalytically active domain of a lysostaphin or a cell wall binding domain of a lysostaphin.

27. The deimmunized lysostaphin of claim 26, wherein the mutation comprises
a) Asn232Gln, Arg186Thr, Ala169Gly, Tyr160His, Ser126Pro, Ser124Gly, Ser122Asp, Asn121Gly, Ile99Gln, Lys95Glu, Leu83Met, Ile41Glu, and Asn12Gly of SEQ ID NO:49;
b) Asn236Asp, Asn232Glu, Arg186Thr, Ala169Gly, Ser166Asn, Tyr160His, Ser126Pro, Ser124Gly, Ser122Asp, Asn121Gly, Ile99Gln, Leu83Met, Ile41Glu, and Asn12Gly of SEQ ID NO:49;
c) Asn236Asp, Asn232Glu, Arg186Thr, Ala169Gly, Ser166Asn, Tyr160His, Ser126Pro, Ser124Gly, Ser122Asp, Asn121Gly, Ile99Gln, Lys95Glu, Leu83Met, Ile41Glu, and Asn12Gly of SEQ ID NO:49;
d) Ser234Lys, Asn219Tyr, Ile200Thr, Ser122Gly, Asn121Gly, Ser84Tyr, Val75Gln, Asn72His, Phe38Ser, and Tyr33Thr of SEQ ID NO:49;
e) Ser122Thr, Val120Asp, Val75Glu, and Ile70Lys of SEQ ID NO:49;
f) Asn219Tyr, Ile200Thr, Ala169Gly, and Ser166Thr of SEQ ID NO:49;
g) Asn219Tyr, Ile200Thr, Ala169Gly, Ser166Thr, Ser122Thr, Val120Asp, Val75Glu, and Ile70Lys of SEQ ID NO:49;
h) Asn236Asp, Asn219Tyr, Ile200Thr, Ala169Gly, Ser166Thr, Ser122Thr, Val120Asp, Ser84Gly, Val75Glu, and Ile70Lys of SEQ ID NO:49;
i) Asn236Asp, Asn219Tyr, Ile200Thr, Ser191Ala, Arg186Thr, Ala169Gly, Ser166Thr, Ser122Thr, Val120Asp, Ser84Gly, Val75Glu, Ile70Lys, and Asn40Tyr of SEQ ID NO:49;
j) Ser122Asp, Ile99Gln, and Ile41Glu of SEQ ID NO:49;
k) Ser124Gly, Ser122Asp, Lys46His, and Ile41Glu of SEQ ID NO:49;
l) Ser122Asp, Ile99Gln, Lys95Glu, and Ile41Glu of SEQ ID NO:49;

m) Ser122Asp, Ile99Gln, Lys95Glu, Tyr93His, and Ile41Glu of SEQ ID NO:49;
n) Ser122Asp, Asn121Gly, Ile99Gln, and Lys46His of SEQ ID NO:49;
o) Ser122Asp, Asn121Gly, Ile99Gln, Ile41Glu, and Asn12Gly of SEQ ID NO:49;
p) Ser124Gly, Ser122Asp, Ile99Gln, Lys95Glu, Ile41Glu, and Asn12Gly of SEQ ID NO:49;
q) Ser122Asp, Asn121Gly, Ile99Gln, Leu83Met, Ile41Glu, and Asn12Gly of SEQ ID NO:49;
r) Ser124Gly, Ser122Asp, Asn121Gly, Ile99Gln, Lys95Glu, Leu83Met, Ile41Glu, and Asn12Gly of SEQ ID NO:49;
s) Ser122Asp, Asn121Gly, Ile41Glu, and Asn912Gly of SEQ ID NO:49;
t) Ser124Gly, Ser122Asp, Asn121Gly, Ile99Gln, Lys95Glu, Tyr93His, Ile41Glu, and Asn12Gly of SEQ ID NO:49;
u) Ser122Asp, Asn121Gly, Ile99Gln, Lys95Glu, Ile41Glu, and Asn13His of SEQ ID NO:49;
v) Ser122Asp, Asn121Gly, Ile99Gln, Lys95Glu, Tyr93His, Ile41Glu, and Asn13His of SEQ ID NO:49;
w) Ser122Asp, and Ile41Glu of SEQ ID NO:49;
x) Ser122Asp, and Lys46His of SEQ ID NO:49;
y) Ser122Asp, Lys95Glu, Tyr93His, and Lys46His of SEQ ID NO:49;
z) Ser122Asp, Lys95Glu, Tyr93His, Leu83Met, Lys46His, Ile41Glu, and Asn12Gly of SEQ ID NO:49;
aa) Ser124Gly, Ser122Asp, Ile99Gln, Lys95Glu, Leu83Met, Ile41Glu, and Asn12Gly of SEQ ID NO:49;
bb) Ser122Asp, Lys95Glu, Leu83Met, Ile41Glu, and Asn12Gly of SEQ ID NO:49;
cc) Ser122Asp, Leu83Met, Ile41Glu, and Asn12Gly of SEQ ID NO:49;
dd) Ser122Asp, Lys95Glu, Tyr93His, Leu83Met, Ile41Glu, and Asn12Gly of SEQ ID NO:49;
ee) Ser122Asp, Ile41Glu, and Asn12Gly of SEQ ID NO:49;
ff) Ser122Asp, Lys95Glu, Tyr93His, Ile41Glu, and Asn12Gly of SEQ ID NO:49;
gg) Ser122Asp, Leu83Met, Lys46His, and Asn13His of SEQ ID NO:49;
hh) Ser122Asp, Lys95Glu, Tyr93His, Leu83Met, Lys46His, and Asn13His of SEQ ID NO:49;
ii) Ser122Asp, Lys46His, and Asn13His of SEQ ID NO:49; or jj) Ser122Asp, Lys95Glu, Tyr93His, Lys46His, and Asn13His of SEQ ID NO:49;

wherein the fragment comprises a catalytically active domain of a lysostaphin or a cell wall binding domain of a lysostaphin.

28. The deimmunized lysostaphin of claim 26, wherein said lysostaphin is aglycosylated.

29. The aglycosylated lysostaphin of claim 28, comprising a mutation at Thr127 and/or Ser234.

30. The aglycosylated lysostaphin of claim 28, comprising the mutation Thr127Ala and/or Ser234Lys.

31. The deimmunized lysostaphin of claim 26, further comprising a mutation at Ser126 in any one of d)-jj).

32. The deimmunized lysostaphin of claim 31, comprising the mutation Ser126Pro.

33. A deimmunized lysostaphin or fragment thereof, comprising a mutation at Ser122 of SEQ ID NO:49 and further comprising one or more additional mutations of SEQ ID NO:49.

34. The de-immunized lysostaphin or fragment thereof of claim 23, where the mutation comprises Asn236Asp, Ser234Lys, Asn232Gln, Asn219Tyr, Ile200Thr, Val193Trp, Ser191Ala, Arg186Thr, Ala169Gly, Ser168Lys, Ser166Asn, or Tyr160His or a combination thereof.

* * * * *

SEQUENCE LISTING

<160> NUMBER OF SEQ ID NOS: 226

<210> SEQ ID NO 1
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 1

```
Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Gly Asp Phe Gly Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 2
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 2

```
Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45
```

```
Ser Ser Gly Lys Ile Val Glu Ala Gly Trp Ser Asn Tyr Gly Gly
    50                  55                  60
Asn Gln Ile Gly Leu Ile Glu Asn Asp Gly Val His Arg Gln Trp Tyr
 65                  70                  75                  80
Met His Met Ser Lys Tyr Asn Val Lys Val Gly Asp Tyr Val Glu Ala
                 85                  90                  95
Gly Gln Gln Ile Gly Trp Ser Gly Ser Thr Gly Tyr Ser Thr Ala Pro
                100                 105                 110
His Leu His Phe Gln Arg Met Val Asn Asp Phe Gly Asn Pro Thr Ala
                115                 120                 125
Gln Asp Pro Met Pro Phe Leu Lys Ser Ala Gly Tyr Gly Lys Ala Gly
            130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
                180                 185                 190
Val Leu Lys Ala Gly Gln Thr Ile His Tyr Asp Glu Val Met Lys Gln
            195                 200                 205
Asp Gly His Val Trp Val Gly Tyr Thr Gly Asn Ser Gly Gln Arg Ile
            210                 215                 220
Tyr Leu Pro Val Arg Thr Trp Asn Lys Ser Thr Asn Thr Leu Gly Val
225                 230                 235                 240
Leu Trp Gly Thr Ile Lys
                245

<210> SEQ ID NO 3
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 3

Ala Ala Thr His Glu His Ser Ala Gln Trp Leu Gly Asn Tyr Lys Lys
 1               5                  10                  15
Gly Tyr Gly Tyr Gly Pro Tyr Pro Leu Gly Ile Asn Gly Gly Met His
                20                  25                  30
Tyr Gly Val Asp Phe Phe Met Asn Glu Gly Thr Pro Val Lys Ala Ile
                35                  40                  45
Ser Ser Gly Lys Ile Val Glu Ala Gly Trp Ser Asn Tyr Gly Gly Gly
    50                  55                  60
Asn Gln Ile Gly Leu Ile Glu Asn Asp Gly Val His Arg Gln Trp Tyr
 65                  70                  75                  80
Met His Met Ser Lys Tyr Asn Val Lys Val Gly Asp Tyr Val Glu Ala
                 85                  90                  95
Gly Gln Gln Ile Gly Trp Ser Gly Ser Thr Gly Tyr Ser Thr Ala Pro
                100                 105                 110
His Leu His Phe Gln Thr Met Val Asn Asp Phe Gly Asn Pro Thr Ala
                115                 120                 125
Gln Asp Pro Met Pro Phe Leu Lys Ser Ala Gly Tyr Gly Lys Ala Gly
            130                 135                 140
Gly Thr Val Thr Pro Thr Pro Asn Thr Gly Trp Lys Thr Asn Lys Tyr
145                 150                 155                 160
```

Gly Thr Leu Tyr Lys Ser Glu Ser Ala Ser Phe Thr Pro Asn Thr Asp
            165                 170                 175

Ile Ile Thr Arg Thr Thr Gly Pro Phe Arg Ser Met Pro Gln Ser Gly
        180                 185                 190

Val Leu Lys Ala Gly Gln Thr Ile His Tyr Asp Glu Val Met Lys Gln
    195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 4
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 4

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
            100                 105                 110

His Leu His Phe Gln Thr Met Val Asn Asp Phe Gly Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 5
<211> LENGTH: 246

```
<212> TYPE: PRT
<213> ORGANISM: Artificial Sequence
<220> FEATURE:
<223> OTHER INFORMATION: Synthetic polypeptide

<400> SEQUENCE: 5

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Gly Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
    195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 6
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 6

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80
```

```
Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Thr Met Val Asn Asp Phe Gly Asn Pro Thr Ala
        115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 7
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 7

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Gly Asn Pro Thr Ala
        115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190
```

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
        210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 8
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 8

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 9
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 9

```
Ala Ala Thr His Glu His Ser Ala Gln Trp Leu Gly Asn Tyr Lys Lys
1               5                   10                  15
Gly Tyr Gly Tyr Gly Pro Tyr Pro Leu Gly Ile Asn Gly Gly Met His
            20                  25                  30
Tyr Gly Val Asp Phe Phe Met Asn Glu Gly Thr Pro Val His Ala Ile
        35                  40                  45
Ser Ser Gly Lys Ile Val Glu Ala Gly Trp Ser Asn Tyr Gly Gly Gly
    50                  55                  60
Asn Gln Ile Gly Leu Ile Glu Asn Asp Gly Val His Arg Gln Trp Tyr
65                  70                  75                  80
Met His Met Ser Lys Tyr Asn Val Lys Val Gly Asp His Val Glu Ala
                85                  90                  95
Gly Gln Ile Ile Gly Trp Ser Gly Ser Thr Gly Tyr Ser Thr Ala Pro
            100                 105                 110
His Leu His Phe Gln Arg Met Val Asn Asp Phe Ser Asn Pro Thr Ala
        115                 120                 125
Gln Asp Pro Met Pro Phe Leu Lys Ser Ala Gly Tyr Gly Lys Ala Gly
    130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
            180                 185                 190
Val Leu Lys Ala Gly Gln Thr Ile His Tyr Asp Glu Val Met Lys Gln
        195                 200                 205
Asp Gly His Val Trp Val Gly Tyr Thr Gly Asn Ser Gly Gln Arg Ile
    210                 215                 220
Tyr Leu Pro Val Arg Thr Trp Asn Lys Ser Thr Asn Thr Leu Gly Val
225                 230                 235                 240
Leu Trp Gly Thr Ile Lys
                245
```

<210> SEQ ID NO 10
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 10

```
Ala Ala Thr His Glu His Ser Ala Gln Trp Leu Gly Asn Tyr Lys Lys
1               5                   10                  15
Gly Tyr Gly Tyr Gly Pro Tyr Pro Leu Gly Ile Asn Gly Gly Met His
            20                  25                  30
Tyr Gly Val Asp Phe Phe Met Asn Glu Gly Thr Pro Val Lys Ala Ile
        35                  40                  45
Ser Ser Gly Lys Ile Val Glu Ala Gly Trp Ser Asn Tyr Gly Gly Gly
    50                  55                  60
Asn Gln Ile Gly Leu Ile Glu Asn Asp Gly Val His Arg Gln Trp Tyr
65                  70                  75                  80
Met His Met Ser Lys Tyr Asn Val Lys Val Gly Asp His Val Glu Ala
                85                  90                  95
Gly Gln Ile Ile Gly Trp Ser Gly Ser Thr Gly Tyr Ser Thr Ala Pro
```

```
                    100                 105                 110
His Leu His Phe Gln Thr Met Val Asn Asp Phe Ser Asn Pro Thr Ala
                115                 120                 125
Gln Asp Pro Met Pro Phe Leu Lys Ser Ala Gly Tyr Gly Lys Ala Gly
            130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
                180                 185                 190
Val Leu Lys Ala Gly Gln Thr Ile His Tyr Asp Glu Val Met Lys Gln
                195                 200                 205
Asp Gly His Val Trp Val Gly Tyr Thr Gly Asn Ser Gly Gln Arg Ile
            210                 215                 220
Tyr Leu Pro Val Arg Thr Trp Asn Lys Ser Thr Asn Thr Leu Gly Val
225                 230                 235                 240
Leu Trp Gly Thr Ile Lys
                245

<210> SEQ ID NO 11
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 11

Ala Ala Thr His Glu His Ser Ala Gln Trp Leu Gly Asn Tyr Lys Lys
1               5                   10                  15
Gly Tyr Gly Tyr Gly Pro Tyr Pro Leu Gly Ile Asn Gly Gly Met His
                20                  25                  30
Tyr Gly Val Asp Phe Phe Met Asn Glu Gly Thr Pro Val Lys Ala Ile
            35                  40                  45
Ser Ser Gly Lys Ile Val Glu Ala Gly Trp Ser Asn Tyr Gly Gly Gly
50                  55                  60
Asn Gln Ile Gly Leu Ile Glu Asn Asp Gly Val His Arg Gln Trp Tyr
65                  70                  75                  80
Met His Met Ser Lys Tyr Asn Val Lys Val Gly Asp His Val Glu Ala
                85                  90                  95
Gly Gln Ile Ile Gly Trp Ser Gly Ser Thr Gly Tyr Ser Thr Ala Pro
            100                 105                 110
His Leu His Phe Gln Arg Met Val Asn Asp Phe Ser Asn Pro Thr Ala
                115                 120                 125
Gln Asp Pro Met Pro Phe Leu Lys Ser Ala Gly Tyr Gly Lys Ala Gly
            130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
                180                 185                 190
Val Leu Lys Ala Gly Gln Thr Ile His Tyr Asp Glu Val Met Lys Gln
                195                 200                 205
Asp Gly His Val Trp Val Gly Tyr Thr Gly Asn Ser Gly Gln Arg Ile
```

```
                210             215                 220
Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 12
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 12

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 13
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 13

Ala Ala Thr His Glu His Ser Ala Gln Trp Leu Gly Asn Tyr Lys Lys
1               5                   10                  15
```

Gly Tyr Gly Tyr Gly Pro Tyr Pro Leu Gly Ile Asn Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
            115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 14
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 14

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Glu Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
            115                 120                 125

```
Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
        210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 15
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 15

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Met His
            20                  25                  30

Tyr Gly Val Asp Phe Phe Met Asn Glu Gly Thr Pro Val Lys Ala Ile
                35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Glu Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
        210                 215                 220

Tyr Leu Pro Val Arg Thr Trp Asn Lys Ser Thr Asn Thr Leu Gly Val
225                 230                 235                 240
```

```
Leu Trp Gly Thr Ile Lys
            245

<210> SEQ ID NO 16
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 16

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
            245

<210> SEQ ID NO 17
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 17

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45
```

```
Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
                100                 105                 110

His Leu His Phe Gln Arg Met Val Asn Asp Phe Ser Asn Pro Thr Ala
            115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 18
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 18

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
                100                 105                 110

His Leu His Phe Gln Thr Met Val Asn Asp Phe Ser Asn Pro Thr Ala
            115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys Tyr
145                 150                 155                 160
```

```
Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 19
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 19

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 20
```

```
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 20
```

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Gln Ile Gly Trp Ser Gly Ser Thr Gly Tyr Ser Thr Ala Pro
                100                 105                 110

His Leu His Phe Gln Arg Met Val Gly Asp Phe Ser Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

```
<210> SEQ ID NO 21
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 21
```

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr

```
              65                  70                  75                  80
Met His Met Ser Lys Tyr Asn Val Lys Val Gly Asp Tyr Val Lys Ala
                    85                  90                  95
Gly Gln Gln Ile Gly Trp Ser Gly Ser Thr Gly Tyr Ser Thr Ala Pro
                100                 105                 110
His Leu His Phe Gln Arg Met Val Gly Asp Phe Ser Asn Pro Thr Ala
            115                 120                 125
Gln Asp Pro Met Pro Phe Leu Lys Ser Ala Gly Tyr Gly Lys Ala Gly
        130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
            180                 185                 190
Val Leu Lys Ala Gly Gln Thr Ile His Tyr Asp Glu Val Met Lys Gln
        195                 200                 205
Asp Gly His Val Trp Val Gly Tyr Thr Gly Asn Ser Gly Gln Arg Ile
    210                 215                 220
Tyr Leu Pro Val Arg Thr Trp Asn Lys Ser Thr Asn Thr Leu Gly Val
225                 230                 235                 240
Leu Trp Gly Thr Ile Lys
                245

<210> SEQ ID NO 22
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 22

Ala Ala Thr His Glu His Ser Ala Gln Trp Leu Gly Asn Tyr Lys Lys
1               5                   10                  15
Gly Tyr Gly Tyr Gly Pro Tyr Pro Leu Gly Ile Asn Gly Gly Met His
                20                  25                  30
Tyr Gly Val Asp Phe Phe Met Asn Glu Gly Thr Pro Val Lys Ala Ile
            35                  40                  45
Ser Ser Gly Lys Ile Val Glu Ala Gly Trp Ser Asn Tyr Gly Gly Gly
        50                  55                  60
Asn Gln Ile Gly Leu Ile Glu Asn Asp Gly Val His Arg Gln Trp Tyr
65                  70                  75                  80
Met His Leu Ser Lys Tyr Asn Val Lys Val Gly Asp Tyr Val Lys Ala
                85                  90                  95
Gly Gln Ile Ile Gly Trp Ser Gly Ser Thr Gly Tyr Ser Thr Ala Pro
                100                 105                 110
His Leu His Phe Gln Arg Met Val Gly Asp Phe Ser Asn Pro Thr Ala
            115                 120                 125
Gln Asp Pro Met Pro Phe Leu Lys Ser Ala Gly Tyr Gly Lys Ala Gly
        130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
```

```
              180                 185                 190
Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
        210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 23
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 23

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 24
<211> LENGTH: 246
<212> TYPE: PRT
<213> ORGANISM: Artificial Sequence
<220> FEATURE:
<223> OTHER INFORMATION: Synthetic polypeptide
```

<400> SEQUENCE: 24

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 25
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 25

```
Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Glu Ala
                85                  90                  95
```

```
Gly Gln Gln Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 26
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 26

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205
```

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 27
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 27

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 28
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 28

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
65                   70                  75                  80

Met His Leu Ser Lys Tyr Asn Val Lys Val Gly Asp His Val Glu Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 29
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 29

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
65                   70                  75                  80

Met His Leu Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
            115                 120                 125

```
Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 30
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 30

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
                35                  40                  45

Ser Ser Gly Lys Ile Val Glu Ala Gly Trp Ser Asn Tyr Gly Gly Gly
            50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
                100                 105                 110

His Leu His Phe Gln Arg Met Val Asn Asp Phe Ser Asn Pro Thr Ala
            115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240
```

```
Leu Trp Gly Thr Ile Lys
            245

<210> SEQ ID NO 31
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 31

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Gln Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
            245

<210> SEQ ID NO 32
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 32

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Glu Gly Thr Pro Val His Ala Ile
```

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Gly Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 33
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 33

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val His Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Gly Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr 145                 150                 155                 160
Gly Thr Leu Tyr Lys Ser Glu Ser Ala Ser Phe Thr Pro Asn Thr Asp
                    165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
        210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 34
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 34

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Met His
                20                  25                  30

Tyr Gly Val Asp Phe Phe Met Asn Ile Gly Thr Pro Val His Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

```
<210> SEQ ID NO 35
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 35

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 36
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 36

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60
```

```
Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 37
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 37

Ala Ala Thr His Glu His Ser Ala Gln Trp Leu Asn His Tyr Lys Lys
  1               5                  10                  15

Gly Tyr Gly Tyr Gly Pro Tyr Pro Leu Gly Ile Asn Gly Gly Met His
                 20                  25                  30

Tyr Gly Val Asp Phe Phe Met Asn Ile Gly Thr Pro Val His Ala Ile
             35                  40                  45

Ser Ser Gly Lys Ile Val Glu Ala Gly Trp Ser Asn Tyr Gly Gly Gly
         50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
            115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175
```

```
Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 38
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 38

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Thr Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 39
<211> LENGTH: 246
<212> TYPE: PRT
<213> ORGANISM: Artificial Sequence
<220> FEATURE:
```

<223> OTHER INFORMATION: Synthetic polypeptide

<400> SEQUENCE: 39

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 40
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 40

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95
```

Gly Gln Gln Ile Gly Trp Ser Gly Ser Thr Gly Tyr Ser Thr Ala Pro
                100                 105                 110

His Leu His Phe Gln Arg Met Val Gly Asp Phe Ser Asn Pro Thr Ala
            115                 120                 125

Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 41
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 41

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val His Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
                100                 105                 110

His Leu His Phe Gln Thr Met Val Asn Asp Phe Ser Asn Pro Thr Ala
            115                 120                 125

Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
            245

<210> SEQ ID NO 42
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 42

Ala Ala Thr His Glu His Ser Ala Gln Trp Leu Asn His Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
            245

<210> SEQ ID NO 43
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 43

Ala Ala Thr His Glu His Ser Ala Gln Trp Leu Asn His Tyr Lys Lys

```
            1               5                  10                 15
Gly Tyr Gly Tyr Gly Pro Tyr Pro Leu Gly Ile Asn Gly Gly Met His
                20                 25                 30
Tyr Gly Val Asp Phe Phe Met Asn Ile Gly Thr Pro Val His Ala Ile
                35                 40                 45
Ser Ser Gly Lys Ile Val Glu Ala Gly Trp Ser Asn Tyr Gly Gly Gly
                50                 55                 60
Asn Gln Ile Gly Leu Ile Glu Asn Asp Gly Val His Arg Gln Trp Tyr
 65                 70                 75                 80
Met His Leu Ser Lys Tyr Asn Val Lys Val Gly Asp His Val Glu Ala
                85                 90                 95
Gly Gln Ile Ile Gly Trp Ser Gly Ser Thr Gly Tyr Ser Thr Ala Pro
                100                105                110
His Leu His Phe Gln Thr Met Val Asn Asp Phe Ser Asn Pro Thr Ala
                115                120                125
Gln Asp Pro Met Pro Phe Leu Lys Ser Ala Gly Tyr Gly Lys Ala Gly
                130                135                140
Gly Thr Val Thr Pro Thr Pro Asn Thr Gly Trp Lys Thr Asn Lys Tyr
145                150                155                160
Gly Thr Leu Tyr Lys Ser Glu Ser Ala Ser Phe Thr Pro Asn Thr Asp
                165                170                175
Ile Ile Thr Arg Thr Thr Gly Pro Phe Arg Ser Met Pro Gln Ser Gly
                180                185                190
Val Leu Lys Ala Gly Gln Thr Ile His Tyr Asp Glu Val Met Lys Gln
                195                200                205
Asp Gly His Val Trp Val Gly Tyr Thr Gly Asn Ser Gly Gln Arg Ile
                210                215                220
Tyr Leu Pro Val Arg Thr Trp Asn Lys Ser Thr Asn Thr Leu Gly Val
225                230                235                240
Leu Trp Gly Thr Ile Lys
                245

<210> SEQ ID NO 44
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 44

Ala Ala Thr His Glu His Ser Ala Gln Trp Leu Asn His Tyr Lys Lys
 1               5                  10                 15
Gly Tyr Gly Tyr Gly Pro Tyr Pro Leu Gly Ile Asn Gly Gly Met His
                20                 25                 30
Tyr Gly Val Asp Phe Phe Met Asn Ile Gly Thr Pro Val His Ala Ile
                35                 40                 45
Ser Ser Gly Lys Ile Val Glu Ala Gly Trp Ser Asn Tyr Gly Gly Gly
                50                 55                 60
Asn Gln Ile Gly Leu Ile Glu Asn Asp Gly Val His Arg Gln Trp Tyr
 65                 70                 75                 80
Met His Leu Ser Lys Tyr Asn Val Lys Val Gly Asp His Val Glu Ala
                85                 90                 95
Gly Gln Ile Ile Gly Trp Ser Gly Ser Thr Gly Tyr Ser Thr Ala Pro
                100                105                110
His Leu His Phe Gln Arg Met Val Asn Asp Phe Ser Asn Pro Thr Ala
```

```
            115                 120                 125
Gln Asp Pro Met Pro Phe Leu Lys Ser Ala Gly Tyr Gly Lys Ala Gly
        130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
            180                 185                 190
Val Leu Lys Ala Gly Gln Thr Ile His Tyr Asp Glu Val Met Lys Gln
        195                 200                 205
Asp Gly His Val Trp Val Gly Tyr Thr Gly Asn Ser Gly Gln Arg Ile
    210                 215                 220
Tyr Leu Pro Val Arg Thr Trp Asn Lys Ser Thr Asn Thr Leu Gly Val
225                 230                 235                 240
Leu Trp Gly Thr Ile Lys
                245

<210> SEQ ID NO 45
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 45

Ala Ala Thr His Glu His Ser Ala Gln Trp Leu Asn Asn Tyr Lys Lys
1               5                   10                  15
Gly Tyr Gly Tyr Gly Pro Tyr Pro Leu Gly Ile Asn Gly Gly Met His
            20                  25                  30
Tyr Gly Val Asp Phe Phe Met Asn Ile Gly Thr Pro Val His Ala Ile
        35                  40                  45
Ser Ser Gly Lys Ile Val Glu Ala Gly Trp Ser Asn Tyr Gly Gly Gly
    50                  55                  60
Asn Gln Ile Gly Leu Ile Glu Asn Asp Gly Val His Arg Gln Trp Tyr
65                  70                  75                  80
Met His Leu Ser Lys Tyr Asn Val Lys Val Gly Asp His Val Glu Ala
                85                  90                  95
Gly Gln Ile Ile Gly Trp Ser Gly Ser Thr Gly Tyr Ser Thr Ala Pro
            100                 105                 110
His Leu His Phe Gln Thr Met Val Asn Asp Phe Ser Asn Pro Thr Ala
        115                 120                 125
Gln Asp Pro Met Pro Phe Leu Lys Ser Ala Gly Tyr Gly Lys Ala Gly
    130                 135                 140
Gly Thr Val Thr Pro Thr Pro Asn Thr Gly Trp Lys Thr Asn Lys Tyr
145                 150                 155                 160
Gly Thr Leu Tyr Lys Ser Glu Ser Ala Ser Phe Thr Pro Asn Thr Asp
                165                 170                 175
Ile Ile Thr Arg Thr Thr Gly Pro Phe Arg Ser Met Pro Gln Ser Gly
            180                 185                 190
Val Leu Lys Ala Gly Gln Thr Ile His Tyr Asp Glu Val Met Lys Gln
        195                 200                 205
Asp Gly His Val Trp Val Gly Tyr Thr Gly Asn Ser Gly Gln Arg Ile
    210                 215                 220
Tyr Leu Pro Val Arg Thr Trp Asn Lys Ser Thr Asn Thr Leu Gly Val
```

```
                   225                 230                 235                 240

Leu Trp Gly Thr Ile Lys
                245

<210> SEQ ID NO 46
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 46

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val His Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp His Val Glu Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Asp Phe Ser Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 47
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 47

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30
```

Tyr Gly Val Asp Phe Phe Met Asn Glu Gly Thr Pro Val Lys Ala Ile
                35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
                100                 105                 110

His Leu His Phe Gln Arg Met Val Asn Asp Phe Ser Asn Pro Thr Ala
                115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
                195                 200                 205

Asp Gly His Val Trp Val Gly Tyr Thr Gly Asn Ser Gly Gln Arg Ile
                210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 48
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 48

Ala Ala Thr His Glu His Ser Ala Gln Trp Leu Asn Asn Tyr Lys Lys
 1               5                  10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
                35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
                100                 105                 110

His Leu His Phe Gln Arg Met Val Asn Asp Phe Ser Asn Pro Thr Ala
                115                 120                 125

Gln Asp Pro Met Pro Phe Leu Lys Ser Ala Gly Tyr Gly Lys Ala Gly
130                 135                 140

```
Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 49
<211> LENGTH: 246
<212> TYPE: PRT
<213> ORGANISM: Staphylococcus simulans

<400> SEQUENCE: 49

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val Lys Ala Ile
                35                  40                  45

Ser Ser Gly Lys Ile Val Glu Ala Gly Trp Ser Asn Tyr Gly Gly Gly
            50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
                100                 105                 110

His Leu His Phe Gln Arg Met Val Asn Ser Phe Ser Asn Ser Thr Ala
            115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
                180                 185                 190

Val Leu Lys Ala Gly Gln Thr Ile His Tyr Asp Glu Val Met Lys Gln
            195                 200                 205

Asp Gly His Val Trp Val Gly Tyr Thr Gly Asn Ser Gly Gln Arg Ile
            210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 50
```

```
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 50
acccttcttg tagttaccca accattgagc gga                              33

<210> SEQ ID NO 51
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 51
tccgctcaat ggttgggtaa ctacaagaag ggt                              33

<210> SEQ ID NO 52
<211> LENGTH: 28
<212> TYPE: DNA
<213> ORGANISM: Artificial Sequence
<220> FEATURE:
<223> OTHER INFORMATION: Sythetic oligonucleotide

<400> SEQUENCE: 52
cgatgaattc ttacttgatg gtacccca                                    28

<210> SEQ ID NO 53
<211> LENGTH: 58
<212> TYPE: DNA
<213> ORGANISM: Artificial Sequence
<220> FEATURE:
<223> OTHER INFORMATION: Sythetic oligonucleotide

<400> SEQUENCE: 53
atcgctcgag aaaagagctg ctacccacga gcactccgct caatggttga accactac   58

<210> SEQ ID NO 54
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 54
ggtaccgatg ttcataccga agtcaacacc gta                              33

<210> SEQ ID NO 55
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 55
tacggtgttg acttcggtat gaacatcggt acc                              33

<210> SEQ ID NO 56
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 56
```
agccttgact ggggtaccct cgttcatgaa gaa              33

<210> SEQ ID NO 57
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 57
ttcttcatga acgagggtac cccagtcaag gct              33

<210> SEQ ID NO 58
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 58
accggaggag atagcgtgga ctggggtacc gat              33

<210> SEQ ID NO 59
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 59
atcggtaccc cagtccacgc tatctcctcc ggt              33

<210> SEQ ID NO 60
<211> LENGTH: 26
<212> TYPE: DNA
<213> ORGANISM: Artificial Sequence
<220> FEATURE:
<223> OTHER INFORMATION: Sythetic oligonucleotide

<400> SEQUENCE: 60
tacttggaca tgtgcatgta ccattg              26

<210> SEQ ID NO 61
<211> LENGTH: 26
<212> TYPE: DNA
<213> ORGANISM: Artificial Sequence
<220> FEATURE:
<223> OTHER INFORMATION: Sythetic oligonucleotide

<400> SEQUENCE: 61
caatggtaca tgcacatgtc caagta              26

<210> SEQ ID NO 62
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 62
ttgaccagcc ttgacgtggt caccgacctt gac              33

<210> SEQ ID NO 63
<211> LENGTH: 33
<212> TYPE: DNA

<213> ORGANISM: Artificial Sequence
<220> FEATURE:
<223> OTHER INFORMATION: Sythetic oligonucleotide

<400> SEQUENCE: 63
gatgatttga ccagcctcga cgtagtcacc gac                              33

<210> SEQ ID NO 64
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 64
gtcggtgact acgtcgaggc tggtcaaatc atc                              33

<210> SEQ ID NO 65
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 65
gtcaaggtcg gtgaccacgt caaggctggt caa                              33

<210> SEQ ID NO 66
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 66
accggaccaa ccgatttgtt gaccagcctt gac                              33

<210> SEQ ID NO 67
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 67
gtcaaggctg gtcaacaaat cggttggtcc ggt                              33

<210> SEQ ID NO 68
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 68
gaaggagttg accatggttt ggaagtgcaa gtg                              33

<210> SEQ ID NO 69
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 69
cacttgcact tccaaaccat ggtcaactcc ttc                              33

<210> SEQ ID NO 70
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 70
tgggttggag aaggaaccga ccattctttg gaa                                    33

<210> SEQ ID NO 71
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 71
ttccaaagaa tggtcggttc cttctccaac cca                                    33

<210> SEQ ID NO 72
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 72
ggttgggttg gagaagtcgt tgaccattct ttg                                    33

<210> SEQ ID NO 73
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 73
caaagaatgg tcaacgactt ctccaaccca acc                                    33

<210> SEQ ID NO 74
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 74
ggttgggttg gagaaaccgt tgaccattct ttg                                    33

<210> SEQ ID NO 75
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 75
caaagaatgg tcaacggttt ctccaaccca acc                                    33

<210> SEQ ID NO 76
<211> LENGTH: 33
<212> TYPE: DNA
<213> ORGANISM: Artificial Sequence
<220> FEATURE:

<223> OTHER INFORMATION: Sythetic oligonucleotide

<400> SEQUENCE: 76
ttgagcggtt gggttaccga aggagttgac cat                       33

<210> SEQ ID NO 77
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 77
atggtcaact ccttcggtaa cccaaccgct caa                       33

<210> SEQ ID NO 78
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 78
ttgagcggtt gggttgtaga aggagttgac cat                       33

<210> SEQ ID NO 79
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 79
atggtcaact ccttctacaa cccaaccgct caa                       33

<210> SEQ ID NO 80
<211> LENGTH: 28
<212> TYPE: DNA
<213> ORGANISM: Artificial Sequence
<220> FEATURE:
<223> OTHER INFORMATION: Sythetic oligonucleotide

<400> SEQUENCE: 80
cgatgaattc ttacttgatg gtacccca                             28

<210> SEQ ID NO 81
<211> LENGTH: 28
<212> TYPE: DNA
<213> ORGANISM: Artificial Sequence
<220> FEATURE:
<223> OTHER INFORMATION: Sythetic oligonucleotide

<400> SEQUENCE: 81
atcgctcgag aaaagagctg ctacccac                             28

<210> SEQ ID NO 82
<211> LENGTH: 21
<212> TYPE: DNA
<213> ORGANISM: Artificial Sequence
<220> FEATURE:
<223> OTHER INFORMATION: Sythetic oligonucleotide

<400> SEQUENCE: 82
gcaaatggca ttctgacatc c                                    21

```
<210> SEQ ID NO 83
<211> LENGTH: 21
<212> TYPE: DNA
<213> ORGANISM: Artificial Sequence
<220> FEATURE:
<223> OTHER INFORMATION: Sythetic oligonucleotide

<400> SEQUENCE: 83
gactggttcc aattgacaag c                                             21

<210> SEQ ID NO 84
<211> LENGTH: 36
<212> TYPE: DNA
<213> ORGANISM: Artificial Sequence
<220> FEATURE:
<223> OTHER INFORMATION: Sythetic oligonucleotide

<400> SEQUENCE: 84
aacgtaacca gcggacttaa ggaatggcat tgggtc                             36

<210> SEQ ID NO 85
<211> LENGTH: 36
<212> TYPE: DNA
<213> ORGANISM: Artificial Sequence
<220> FEATURE:
<223> OTHER INFORMATION: Sythetic oligonucleotide

<400> SEQUENCE: 85
gacccaatgc cattccttaa gtccgctggt tacggt                             36

<210> SEQ ID NO 86
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 86
gaagtcgttg accattcttt ggaagtgcaa gtg                                33

<210> SEQ ID NO 87
<211> LENGTH: 33
<212> TYPE: DNA
<213> ORGANISM: Artificial Sequence
<220> FEATURE:
<223> OTHER INFORMATION: Sythetic oligonucleotide

<400> SEQUENCE: 87
cacttgcact tccaaagaat ggtcaacgac ttc                                33

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Phe Gln Arg Met Val Asn Ser Phe Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 89

Trp Leu Asn Asn Tyr Lys Lys Gly Tyr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide

<400> SEQUENCE: 90

Leu Asn Asn Tyr Lys Lys Gly Tyr Gly
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide

<400> SEQUENCE: 91

Ile Asn Gly Gly Met His Tyr Gly Val
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide

<400> SEQUENCE: 92

Val Asp Phe Phe Met Asn Ile Gly Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Phe Phe Met Asn Ile Gly Thr Pro Val
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Phe Met Asn Ile Gly Thr Pro Val Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 95

Met Asn Ile Gly Thr Pro Val Lys Ala
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Ile Gly Thr Pro Val Lys Ala Ile Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

Val Lys Ala Ile Ser Ser Gly Lys Ile
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Ile Glu Asn Asp Gly Val His Arg Gln
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic peptide

<400> SEQUENCE: 99

Val His Arg Gln Trp Tyr Met His Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide

<400> SEQUENCE: 100

Trp Tyr Met His Leu Ser Lys Tyr Asn
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide

<400> SEQUENCE: 101
```

```
Tyr Met His Leu Ser Lys Tyr Asn Val
1               5
```

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide

<400> SEQUENCE: 102

```
Leu Ser Lys Tyr Asn Val Lys Val Gly
1               5
```

<210> SEQ ID NO 103
<211> LENGTH: 9
<212> TYPE: PRT
<213> ORGANISM: Artificial Sequence
<220> FEATURE:
<223> OTHER INFORMATION: Synthetic peptide

<400> SEQUENCE: 103

```
Tyr Val Lys Ala Gly Gln Ile Ile Gly
1               5
```

<210> SEQ ID NO 104
<211> LENGTH: 9
<212> TYPE: PRT
<213> ORGANISM: Artificial Sequence
<220> FEATURE:
<223> OTHER INFORMATION: Synthetic peptide

<400> SEQUENCE: 104

```
Ile Ile Gly Trp Ser Gly Ser Thr Gly
1               5
```

<210> SEQ ID NO 105
<211> LENGTH: 9
<212> TYPE: PRT
<213> ORGANISM: Artificial Sequence
<220> FEATURE:
<223> OTHER INFORMATION: Synthetic peptide

<400> SEQUENCE: 105

```
Trp Ser Gly Ser Thr Gly Tyr Ser Thr
1               5
```

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide

<400> SEQUENCE: 106

```
Leu His Phe Gln Arg Met Val Asn Ser
1               5
```

<210> SEQ ID NO 107
<211> LENGTH: 9
<212> TYPE: PRT
<213> ORGANISM: Artificial Sequence
<220> FEATURE:
<223> OTHER INFORMATION: Synthetic peptide

<400> SEQUENCE: 107

Gln Arg Met Val Asn Ser Phe Ser Gln
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Met Val Asn Ser Phe Ser Gln Ser Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic peptide

<400> SEQUENCE: 109

Gln Thr Met Val Asn Ser Phe Ser Gln
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic peptide

<400> SEQUENCE: 110

Gln Arg Met Val Asn Ser Phe Gly Gln
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic peptide

<400> SEQUENCE: 111

Met Val Asn Ser Phe Gly Gln Ser Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic peptide

<400> SEQUENCE: 112

Phe Gln Arg Met Val Asn Gly Phe Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic peptide

<400> SEQUENCE: 113

Gln Arg Met Val Asn Gly Phe Ser Gln 1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide

<400> SEQUENCE: 114

Met Val Asn Gly Phe Ser Gln Ser Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide

<400> SEQUENCE: 115

Tyr Val Glu Ala Gly Gln Ile Ile Gly
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide

<400> SEQUENCE: 116

Val Asp Phe Gly Met Asn Ile Gly Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide

<400> SEQUENCE: 117

Phe Gly Met Asn Ile Gly Thr Pro Val
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic peptide

<400> SEQUENCE: 118

Gly Met Asn Ile Gly Thr Pro Val Lys
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Trp Leu Gly Asn Tyr Lys Lys Gly Tyr
1               5

```
<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Leu Gly Asn Tyr Lys Lys Gly Tyr Gly
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide

<400> SEQUENCE: 121

Met Asn Ile Gly Thr Pro Val His Ala
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic peptide

<400> SEQUENCE: 122

Ile Gly Thr Pro Val His Ala Ile Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic peptide

<400> SEQUENCE: 123

Val His Ala Ile Ser Ser Gly Lys Ile
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide

<400> SEQUENCE: 124

His Val Lys Ala Gly Gln Ile Ile Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

Leu His Phe Gln Arg Met Val Asn Asp
1               5
```

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

Phe Gln Arg Met Val Asn Asp Phe Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide

<400> SEQUENCE: 127

Gln Arg Met Val Asn Asp Phe Ser Gln
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide

<400> SEQUENCE: 128

Met Val Asn Asp Phe Ser Gln Ser Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide

<400> SEQUENCE: 129

Val His Arg Gln Trp Tyr Met His Met
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Met Ser Lys Tyr Asn Val Lys Val Gly
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide

<400> SEQUENCE: 131

Gln Arg Met Val Gly Ser Phe Ser Gln
1               5

```
<210> SEQ ID NO 132
<211> LENGTH: 9
<212> TYPE: PRT
<213> ORGANISM: Artificial Sequence
<220> FEATURE:
<223> OTHER INFORMATION: Synthetic peptide

<400> SEQUENCE: 132

Phe Gln Arg Met Val Asn Ser Phe Tyr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic peptide

<400> SEQUENCE: 133

Gln Arg Met Val Asn Ser Phe Tyr Gln
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide

<400> SEQUENCE: 134

Met Val Asn Ser Phe Tyr Gln Ser Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic peptide

<400> SEQUENCE: 135

Trp Leu Asn His Tyr Lys Lys Gly Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic peptide

<400> SEQUENCE: 136

Val Asp Phe Phe Met Asn Glu Gly Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic peptide

<400> SEQUENCE: 137

Phe Met Asn Glu Gly Thr Pro Val Lys
1               5

<210> SEQ ID NO 138
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 138

Met Asn Glu Gly Thr Pro Val Lys Ala
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic peptide

<400> SEQUENCE: 139

Glu Gly Thr Pro Val Lys Ala Ile Ser
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic peptide

<400> SEQUENCE: 140

Tyr Val Lys Ala Gly Gln Gln Ile Gly
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic peptide

<400> SEQUENCE: 141

Gln Ile Gly Trp Ser Gly Ser Thr Gly
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic peptide

<400> SEQUENCE: 142

Met Val Asn Ser Phe Ser Asn Pro Thr
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic peptide

<400> SEQUENCE: 143

Val Asn Ser Phe Ser Asn Pro Thr Ala
1               5

<210> SEQ ID NO 144
<211> LENGTH: 9
```

<212> TYPE: PRT
<213> ORGANISM: Artificial Sequence
<220> FEATURE:
<223> OTHER INFORMATION: Synthetic peptide

<400> SEQUENCE: 144

Met Val Asn Asp Phe Ser Asn Pro Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic peptide

<400> SEQUENCE: 145

Val Asn Asp Phe Ser Asn Pro Thr Ala
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic peptide

<400> SEQUENCE: 146

Val Gly Ser Phe Ser Asn Pro Thr Ala
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic peptide

<400> SEQUENCE: 147

Trp Met His Leu Ser Lys Tyr Asn Val
1               5

<210> SEQ ID NO 148
<211> LENGTH: 15
<212> TYPE: PRT
<213> ORGANISM: Artificial Sequence
<220> FEATURE:
<223> OTHER INFORMATION: Synthetic peptide

<400> SEQUENCE: 148

Ser Ala Gln Trp Leu Asn Asn Tyr Lys Lys Gly Tyr Gly Tyr Gly
1               5                   10                  15

<210> SEQ ID NO 149
<211> LENGTH: 19
<212> TYPE: PRT
<213> ORGANISM: Artificial Sequence
<220> FEATURE:
<223> OTHER INFORMATION: Synthetic peptide

<400> SEQUENCE: 149

Gly Val His Arg Gln Trp Tyr Met His Leu Ser Lys Tyr Asn Val Lys
1               5                   10                  15

Val Gly Asp

<210> SEQ ID NO 150

```
<211> LENGTH: 19
<212> TYPE: PRT
<213> ORGANISM: Artificial Sequence
<220> FEATURE:
<223> OTHER INFORMATION: Synthetic peptide

<400> SEQUENCE: 150

Gly Val His Arg Gln Trp Tyr Met His Met Ser Lys Tyr Asn Val Lys
1               5                   10                  15

Val Gly Asp

<210> SEQ ID NO 151
<211> LENGTH: 17
<212> TYPE: PRT
<213> ORGANISM: Artificial Sequence
<220> FEATURE:
<223> OTHER INFORMATION: Synthetic peptide

<400> SEQUENCE: 151

Asp Tyr Val Lys Ala Gly Gln Ile Ile Gly Trp Ser Gly Ser Thr Gly
1               5                   10                  15

Tyr

<210> SEQ ID NO 152
<211> LENGTH: 17
<212> TYPE: PRT
<213> ORGANISM: Artificial Sequence
<220> FEATURE:
<223> OTHER INFORMATION: Synthetic peptide

<400> SEQUENCE: 152

Asp His Val Lys Ala Gly Gln Ile Ile Gly Trp Ser Gly Ser Thr Gly
1               5                   10                  15

Tyr

<210> SEQ ID NO 153
<211> LENGTH: 17
<212> TYPE: PRT
<213> ORGANISM: Artificial Sequence
<220> FEATURE:
<223> OTHER INFORMATION: Synthetic peptide

<400> SEQUENCE: 153

Asp Tyr Val Glu Ala Gly Gln Ile Ile Gly Trp Ser Gly Ser Thr Gly
1               5                   10                  15

Tyr

<210> SEQ ID NO 154
<211> LENGTH: 17
<212> TYPE: PRT
<213> ORGANISM: Artificial Sequence
<220> FEATURE:
<223> OTHER INFORMATION: Synthetic peptide

<400> SEQUENCE: 154

Asp Tyr Val Lys Ala Gly Gln Gln Ile Gly Trp Ser Gly Ser Thr Gly
1               5                   10                  15

Tyr

<210> SEQ ID NO 155
<211> LENGTH: 17
<212> TYPE: PRT
<213> ORGANISM: Artificial Sequence
<220> FEATURE:
```

<223> OTHER INFORMATION: Synthetic peptide

<400> SEQUENCE: 155

Asp His Val Lys Ala Gly Gln Gln Ile Gly Trp Ser Gly Ser Thr Gly
1               5                   10                  15
Tyr

<210> SEQ ID NO 156
<211> LENGTH: 17
<212> TYPE: PRT
<213> ORGANISM: Artificial Sequence
<220> FEATURE:
<223> OTHER INFORMATION: Synthetic peptide

<400> SEQUENCE: 156

Asp His Val Glu Ala Gly Gln Ile Ile Gly Trp Ser Gly Ser Thr Gly
1               5                   10                  15
Tyr

<210> SEQ ID NO 157
<211> LENGTH: 17
<212> TYPE: PRT
<213> ORGANISM: Artificial Sequence
<220> FEATURE:
<223> OTHER INFORMATION: Synthetic peptide

<400> SEQUENCE: 157

Asp Tyr Val Glu Ala Gly Gln Gln Ile Gly Trp Ser Gly Ser Thr Gly
1               5                   10                  15
Tyr

<210> SEQ ID NO 158
<211> LENGTH: 17
<212> TYPE: PRT
<213> ORGANISM: Artificial Sequence
<220> FEATURE:
<223> OTHER INFORMATION: Synthetic peptide

<400> SEQUENCE: 158

Asp His Val Glu Ala Gly Gln Gln Ile Gly Trp Ser Gly Ser Thr Gly
1               5                   10                  15
Tyr

<210> SEQ ID NO 159
<211> LENGTH: 17
<212> TYPE: PRT
<213> ORGANISM: Artificial Sequence
<220> FEATURE:
<223> OTHER INFORMATION: Synthetic peptide

<400> SEQUENCE: 159

His Leu His Phe Gln Arg Met Val Asn Ser Phe Ser Asn Pro Thr Ala
1               5                   10                  15
Gln

<210> SEQ ID NO 160
<211> LENGTH: 17
<212> TYPE: PRT
<213> ORGANISM: Artificial Sequence
<220> FEATURE:
<223> OTHER INFORMATION: Synthetic peptide

<400> SEQUENCE: 160

His Leu His Phe Gln Thr Met Val Asn Ser Phe Ser Asn Pro Thr Ala
1               5                   10                  15

Gln

<210> SEQ ID NO 161
<211> LENGTH: 17
<212> TYPE: PRT
<213> ORGANISM: Artificial Sequence
<220> FEATURE:
<223> OTHER INFORMATION: Synthetic peptide

<400> SEQUENCE: 161

His Leu His Phe Gln Arg Met Val Gly Ser Phe Ser Asn Pro Thr Ala
1               5                   10                  15

Gln

<210> SEQ ID NO 162
<211> LENGTH: 17
<212> TYPE: PRT
<213> ORGANISM: Artificial Sequence
<220> FEATURE:
<223> OTHER INFORMATION: Synthetic peptide

<400> SEQUENCE: 162

His Leu His Phe Gln Arg Met Val Asn Asp Phe Ser Asn Pro Thr Ala
1               5                   10                  15

Gln

<210> SEQ ID NO 163
<211> LENGTH: 17
<212> TYPE: PRT
<213> ORGANISM: Artificial Sequence
<220> FEATURE:
<223> OTHER INFORMATION: Synthetic peptide

<400> SEQUENCE: 163

His Leu His Phe Gln Arg Met Val Asn Ser Phe Gly Asn Pro Thr Ala
1               5                   10                  15

Gln

<210> SEQ ID NO 164
<211> LENGTH: 17
<212> TYPE: PRT
<213> ORGANISM: Artificial Sequence
<220> FEATURE:
<223> OTHER INFORMATION: Synthetic peptide

<400> SEQUENCE: 164

His Leu His Phe Gln Thr Met Val Asn Asp Phe Ser Asn Pro Thr Ala
1               5                   10                  15

Gln

<210> SEQ ID NO 165
<211> LENGTH: 17
<212> TYPE: PRT
<213> ORGANISM: Artificial Sequence
<220> FEATURE:
<223> OTHER INFORMATION: Synthetic peptide

<400> SEQUENCE: 165

His Leu His Phe Gln Thr Met Val Asn Asp Phe Gly Asn Pro Thr Ala
1               5                   10                  15

Gln

<210> SEQ ID NO 166
<211> LENGTH: 17
<212> TYPE: PRT
<213> ORGANISM: Artificial Sequence
<220> FEATURE:
<223> OTHER INFORMATION: Synthetic peptide

<400> SEQUENCE: 166

His Leu His Phe Gln Arg Met Val Gly Asp Phe Ser Asn Pro Thr Ala
1               5                   10                  15

Gln

<210> SEQ ID NO 167
<211> LENGTH: 17
<212> TYPE: PRT
<213> ORGANISM: Artificial Sequence
<220> FEATURE:
<223> OTHER INFORMATION: Synthetic peptide

<400> SEQUENCE: 167

His Leu His Phe Gln Arg Met Val Gly Asp Phe Gly Asn Pro Thr Ala
1               5                   10                  15

Gln

<210> SEQ ID NO 168
<211> LENGTH: 7
<212> TYPE: PRT
<213> ORGANISM: Artificial Sequence
<220> FEATURE:
<223> OTHER INFORMATION: Synthetic peptide

<400> SEQUENCE: 168

Pro Leu Gly Ile Asn Gly Gly
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic peptide

<400> SEQUENCE: 169

Pro Arg Gly Glu Glu Gly Gly
1               5

<210> SEQ ID NO 170
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 170
ggtatgcacd atggtgttga cttctytatg aacatcggta mgccagtcaa g        51

<210> SEQ ID NO 171
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 171
cttgactggc ktaccgatgt tcataragaa gtcaacacca thgtgcatac c          51

<210> SEQ ID NO 172
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 172
ggtttgadag agaacgacgg tgwscacaga caawsgtaca tgcacttgvg taagtac    57

<210> SEQ ID NO 173
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 173
gtacttacbc aagtgcatgt acswttgtct gtgswcaccg tcgttctcth tcaaacc    57

<210> SEQ ID NO 174
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 174
cacttccaaa gaatggwtaa cdskttctcc aactccgct                        39

<210> SEQ ID NO 175
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 175
agcggagttg gagaamshgt tawccattct ttggaagtg                        39

<210> SEQ ID NO 176
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 176
ggtaccttgt acaagasmga gtccgsctcc ttcaccccaa ac                    42

<210> SEQ ID NO 177
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 177
gtttggggtg aaggagscgg actckstctt gtacaaggta cc                    42

<210> SEQ ID NO 178
<211> LENGTH: 54
<212> TYPE: DNA
<213> ORGANISM: Artificial Sequence

```
<220> FEATURE:
<223> OTHER INFORMATION: Synthetic oligonucleotide

<400> SEQUENCE: 178
tccatgccac aargcggtgd mttgaaggct ggtcaaacca ytcactacga cgag        54

<210> SEQ ID NO 179
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 179
ctcgtcgtag tgartggttt gaccagcctt caakhcaccg cyttgtggca tgga        54

<210> SEQ ID NO 180
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 180
gtdattccgg tsagagaatc tacttgccag tcagaacctg aacaagtcc accvawac    58

<210> SEQ ID NO 181
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 181
gtwtbggtgg acttgttcca ggttctgact ggcaagtaga ttctctsacc ggaathac    58

<210> SEQ ID NO 182
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 182
ggtggtatgc acdatggtgt tgacttctttt vkgaacatcg gtamgccagt caaggct    57

<210> SEQ ID NO 183
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 183
agccttgact ggcktaccga tgttcmbaaa gaagtcaaca ccathgtgca taccacc    57

<210> SEQ ID NO 184
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 184
ggtgagcaca gacaawsgta catgcacttg vgtaagtaca acgtcaag              48
```

<210> SEQ ID NO 185
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 185
cttgacgttg tacttacbca agtgcatgta cswttgtctg tgctcacc                48

<210> SEQ ID NO 186
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 186
agatccatgc cacaargcgg tgdcttgaag gctggtcaa                39

<210> SEQ ID NO 187
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 187
ttgaccagcc ttcaaghcac cgcyttgtgg catggatct                39

<210> SEQ ID NO 188
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 188
atcggaattc ttacttgatg gtacccacaa agacacccaa ggtwtbggtg gacttgttc                59

<210> SEQ ID NO 189
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 189
ggtatgcacw atgrcgttga cttctttatg aacatcggta mgccaktaaa ggctatc                57

<210> SEQ ID NO 190
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 190
gatagccttt amtggcktac cgatgttcat aaagaagtca acgycatwgt gcatacc                57

<210> SEQ ID NO 191
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 191
ggtatgcacd atggtgttga cttctttatg amwatcggta vaccagtcaa g    51

<210> SEQ ID NO 192
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 192
cttgactggt btaccgatwk tcataaagaa gtcaacacca thgtgcatac c    51

<210> SEQ ID NO 193
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 193
cactatggtg wsgacttctt tatgaacatc ggtavaccag dmaaggctat c    51

<210> SEQ ID NO 194
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 194
gatagccttk hctggtbtac cgatgttcat aaagaagtcs wcaccatagt g    51

<210> SEQ ID NO 195
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 195
ccacacttgc actbccaaag aatggat    27

<210> SEQ ID NO 196
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 196
atccattctt tggvagtgca agtgtgg    27

<210> SEQ ID NO 197
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 197
ggtccattca sgtccatgcc acaakctggt gtcttg    36

<210> SEQ ID NO 198

```
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 198
caagacacca gmttgtggca tggacstgaa tggacc                              36

<210> SEQ ID NO 199
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 199
tccatgccac aargcggtgd cttgaaggct ggt                                 33

<210> SEQ ID NO 200
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 200
accagccttc aaghcaccgc yttgtggcat gga                                 33

<210> SEQ ID NO 201
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t

<400> SEQUENCE: 201
ggtccattcn sstccatgcc acaaagcggt vdrttgaagg ct                       42

<210> SEQ ID NO 202
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (33)..(33)
<223> OTHER INFORMATION: n is a, c, g, or t

<400> SEQUENCE: 202
agccttcaay hbaccgcttt gtggcatgga ssngaatgga cc                       42

<210> SEQ ID NO 203
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 203
gtatcarcgg tggtatgcac tatggcgttg acttctttat gaccawcggt amgccagt     58
```

```
<210> SEQ ID NO 204
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 204
actggcktac cgwtggtcat aaagaagtca acgccatagt gcataccacc gytgatac        58

<210> SEQ ID NO 205
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 205
cactatgrcg ttgacttctt tatgaccawm ggtamgccag ta                          42

<210> SEQ ID NO 206
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 206
tactggckta cckwtggtca taaagaagtc aacgycatag tg                          42

<210> SEQ ID NO 207
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 207
cactatgrkg ttgacttctt tatgaccrdr ggtavaccag ta                          42

<210> SEQ ID NO 208
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 208
tactggtbta ccyhyggtca taaagaagtc aacmycatag tg                          42

<210> SEQ ID NO 209
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 209
gtatcaasgg tgraatgcac tatggcgttg acttctttat gaccawcggt avaccagt        58

<210> SEQ ID NO 210
<211> LENGTH: 58
<212> TYPE: DNA
<213> ORGANISM: Artificial Sequence
<220> FEATURE:
<223> OTHER INFORMATION: Synthetic oligonucleotide
```

```
<400> SEQUENCE: 210
actggtbtac cgwtggtcat aaagaagtca acgccatagt gcattycacc sttgatac        58

<210> SEQ ID NO 211
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 211
agaatggata asactttcts saactccgct                                       30

<210> SEQ ID NO 212
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 212
agcggagtts sagaaagtst tatccattct                                       30

<210> SEQ ID NO 213
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 213
agaatggata acayrttcts saactccgct gct                                   33

<210> SEQ ID NO 214
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 214
agcagcggag ttssagaayr tgttatccat tct                                   33

<210> SEQ ID NO 215
<211> LENGTH: 9
<212> TYPE: PRT
<213> ORGANISM: Artificial Sequence
<220> FEATURE:
<223> OTHER INFORMATION: Synthetic peptide

<400> SEQUENCE: 215

Tyr Gly Val Asp Phe Phe Met Thr Ile
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic peptide

<400> SEQUENCE: 216

Phe Met Thr Ile Gly Thr Pro Val Lys
1               5
```

```
<210> SEQ ID NO 217
<211> LENGTH: 9
<212> TYPE: PRT
<213> ORGANISM: Artificial Sequence
<220> FEATURE:
<223> OTHER INFORMATION: Synthetic peptide

<400> SEQUENCE: 217

Phe Gln Arg Met Asp Asn Thr Phe Ser
1               5

<210> SEQ ID NO 218
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 218

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
                100                 105                 110

His Leu His Phe Gln Arg Met Val Gly Asp Phe Gly Asn Pro Thr Ala
            115                 120                 125

Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys His
145                 150                 155                 160

Gly Thr Leu Tyr Lys Ser Glu Ser Gly Ser Phe Thr Pro Asn Thr Asp
                165                 170                 175

Ile Ile Thr Arg Thr Thr Gly Pro Phe Thr Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Gln Lys Ser Thr Asn Thr Leu Gly Val
225                 230                 235                 240

Leu Trp Gly Thr Ile Lys
                245

<210> SEQ ID NO 219
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 219
```

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Lys Ala
                85                  90                  95

Gly Gln Gln Ile Gly Trp Ser Gly Ser Thr Gly Tyr Ser Thr Ala Pro
                100                 105                 110

His Leu His Phe Gln Arg Met Val Gly Asp Phe Gly Asn Pro Thr Ala
                115                 120                 125

Gln Asp Pro Met Pro Phe Leu Lys Ser Ala Gly Tyr Gly Lys Ala Gly
            130                 135                 140

Gly Thr Val Thr Pro Thr Pro Asn Thr Gly Trp Lys Thr Asn Lys His
145                 150                 155                 160

Gly Thr Leu Tyr Lys Asn Glu Ser Gly Ser Phe Thr Pro Asn Thr Asp
                165                 170                 175

Ile Ile Thr Arg Thr Thr Gly Pro Phe Thr Ser Met Pro Gln Ser Gly
                180                 185                 190

Val Leu Lys Ala Gly Gln Thr Ile His Tyr Asp Glu Val Met Lys Gln
                195                 200                 205

Asp Gly His Val Trp Val Gly Tyr Thr Gly Asn Ser Gly Gln Arg Ile
            210                 215                 220

Tyr Leu Pro Val Arg Thr Trp Gln Lys Ser Thr Asp Thr Leu Gly Val
225                 230                 235                 240

Leu Trp Gly Thr Ile Lys
                245

<210> SEQ ID NO 220
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 220

Ala Ala Thr His Glu His Ser Ala Gln Trp Leu Gly Asn Tyr Lys Lys
1               5                   10                  15

Gly Tyr Gly Tyr Gly Pro Tyr Pro Leu Gly Ile Asn Gly Met His
            20                  25                  30

Tyr Gly Val Asp Phe Phe Met Asn Glu Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Met Ser Lys Tyr Asn Val Lys Val Gly Asp Tyr Val Glu Ala
                85                  90                  95

Gly Gln Gln Ile Gly Trp Ser Gly Ser Thr Gly Tyr Ser Thr Ala Pro
                100                 105                 110

His Leu His Phe Gln Arg Met Val Gly Asp Phe Gly Asn Pro Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys His
145                 150                 155                 160

Gly Thr Leu Tyr Lys Asn Glu Ser Gly Ser Phe Thr Pro Asn Thr Asp
                165                 170                 175

Ile Ile Thr Arg Thr Thr Gly Pro Phe Thr Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Gln Lys Ser Thr Asp Thr Leu Gly Val
225                 230                 235                 240

Leu Trp Gly Thr Ile Lys
                245

<210> SEQ ID NO 221
<211> LENGTH: 15
<212> TYPE: PRT
<213> ORGANISM: Artificial Sequence
<220> FEATURE:
<223> OTHER INFORMATION: Synthetic peptide

<400> SEQUENCE: 221

Ser Ala Gln Trp Leu Gly Asn Tyr Lys Lys Gly Tyr Gly Tyr Gly
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Synthetic peptide

<400> SEQUENCE: 222

Ser Ala Gln Trp Leu Asn His Tyr Lys Lys Gly Tyr Gly Tyr Gly
1               5                   10                  15

<210> SEQ ID NO 223
<211> LENGTH: 21
<212> TYPE: PRT
<213> ORGANISM: Artificial Sequence
<220> FEATURE:
<223> OTHER INFORMATION: Synthetic peptide

<400> SEQUENCE: 223

Gly Val Asp Phe Phe Met Asn Ile Gly Thr Pro Val Lys Ala Ile Ser
1               5                   10                  15

Ser Gly Lys Ile Val
            20

<210> SEQ ID NO 224
<211> LENGTH: 21
<212> TYPE: PRT
<213> ORGANISM: Artificial sequence
<220> FEATURE:
<223> OTHER INFORMATION: Synthetic peptide

<400> SEQUENCE: 224

```
Gly Val Asp Phe Phe Met Asn Glu Gly Thr Pro Val Lys Ala Ile Ser
1               5                   10                  15

Ser Gly Lys Ile Val
            20

<210> SEQ ID NO 225
<211> LENGTH: 21
<212> TYPE: PRT
<213> ORGANISM: Artificial Sequence
<220> FEATURE:
<223> OTHER INFORMATION: Synthetic peptide

<400> SEQUENCE: 225

Gly Val Asp Phe Phe Met Asn Ile Gly Thr Pro Val His Ala Ile Ser
1               5                   10                  15

Ser Gly Lys Ile Val
            20

<210> SEQ ID NO 226
<211> LENGTH: 21
<212> TYPE: PRT
<213> ORGANISM: Artificial Sequence
<220> FEATURE:
<223> OTHER INFORMATION: Synthetic peptide

<400> SEQUENCE: 226

Gly Val Asp Phe Phe Met Asn Glu Gly Thr Pro Val His Ala Ile Ser
1               5                   10                  15

Ser Gly Lys Ile Val
            20
```

UNITED STATES PATENT AND TRADEMARK OFFICE
CERTIFICATE OF CORRECTION

PATENT NO. : 10,358,636 B2  Page 1 of 1
APPLICATION NO. : 15/310917
DATED : July 23, 2019
INVENTOR(S) : Karl E. Griswold It is certified that error appears in the above-identified patent and that said Letters Patent is hereby corrected as shown below:

In the Claims

Column 193, Line 39 – change "Argi18" to "Arg118" in Claim 1
Column 195, Line 23 – change "orTyr160" to "or Tyr160" in Claim 23
Column 197, Line 14 – change "Asn912Gly" to "Asn12Gly" in Claim 27, part s)
Column 198, Line 10 – change "or jj)" to "or" "jj)" with "jj)" on a new line in Claim 27, part jj)
Column 198, Line 34 – change "orTyr160His or a combination thereof" to "Tyr160His, or a combination thereof." in Claim 34

Signed and Sealed this
Eighth Day of December, 2020

Andrei Iancu
*Director of the United States Patent and Trademark Office*